United States Patent
Oshiyama et al.

(10) Patent No.: US 8,795,853 B2
(45) Date of Patent: *Aug. 5, 2014

(54) ORGANIC ELECTROLUMINESCENT ELEMENT USING IRIDIUM COMPLEX, DISPLAY DEVICE AND LIGHTING DEVICE USING IRIDIUM COMPLEX

(71) Applicant: Konica Minolta, Inc., Tokyo (JP)

(72) Inventors: Tomohiro Oshiyama, Tokyo (JP); Masato Nishizeki, Tokyo (JP); Noboru Sekine, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/739,858

(22) Filed: Jan. 11, 2013

(65) Prior Publication Data

US 2013/0146813 A1  Jun. 13, 2013

Related U.S. Application Data

(63) Continuation of application No. 11/814,652, filed as application No. PCT/JP2006/301180 on Jan. 26, 2006, now Pat. No. 8,377,571.

(30) Foreign Application Priority Data

Feb. 4, 2005  (JP) ................................ 2005-028668

(51) Int. Cl.
  *H01L 51/54*  (2006.01)
  *C09K 11/06*  (2006.01)
  *H01L 51/00*  (2006.01)
  *C07F 15/00*  (2006.01)
  *H01L 51/50*  (2006.01)

(52) U.S. Cl.
  CPC ............ *H01L 51/0087* (2013.01); *C09K 11/06* (2013.01); *H01L 51/5096* (2013.01); *H01L 51/0086* (2013.01); *H01L 51/0085* (2013.01); *C09K 2211/1011* (2013.01); *C09K 2211/1029* (2013.01); *C09K 2211/1425* (2013.01); *C09K 2211/1007* (2013.01); *C07F 15/0033* (2013.01); *C09K 2211/1044* (2013.01); *C09K 2211/1466* (2013.01); *H01L 51/5016* (2013.01); *H01L 51/004* (2013.01); *H01L 51/0072* (2013.01); *H01L 51/0071* (2013.01); *C09K 2211/1092* (2013.01); *C09K 2211/1416* (2013.01); *C09K 2211/1059* (2013.01); *H01L 51/0081* (2013.01); *H01L 51/009* (2013.01); *C07F 15/0086* (2013.01); *H01L 51/0084* (2013.01); *H01L 51/006* (2013.01); *Y10S 428/917* (2013.01)
  USPC ............ 428/690; 428/917; 257/40; 313/540; 252/301.16; 252/506

(58) Field of Classification Search
  None
  See application file for complete search history.

(56) References Cited

U.S. PATENT DOCUMENTS 8,377,571 B2 *  2/2013  Oshiyama et al. ............ 428/690
2003/0017361 A1 *  1/2003  Thompson et al. ........... 428/690
2005/0249970 A1 *  11/2005  Suzuri et al. .................. 428/690

FOREIGN PATENT DOCUMENTS

WO   WO 2004095889 A1 *  11/2004
WO   WO 2004108857 A1 *  12/2004

* cited by examiner

*Primary Examiner* — Andrew K Bohaty
(74) *Attorney, Agent, or Firm* — Lucas & Mercanti, LLP

(57) ABSTRACT

A material for an organic EL element showing high light emission efficiency and high color purity of the emission light, an organic EL element, a lighting device and a displaying device each using the material.

6 Claims, 3 Drawing Sheets

LIGHT

ORGANIC ELECTROLUMINESCENT ELEMENT USING IRIDIUM COMPLEX, DISPLAY DEVICE AND LIGHTING DEVICE USING IRIDIUM COMPLEX

This Application is a Continuation of U.S. patent application Ser. No. 11/814,652 filed Jul. 24, 2007, now U.S. Pat. No. 8,377,571 issued Feb. 19, 2013, which was a 371 of PCT/JP2006/301180 filed Jan. 26, 2006 which claimed priority to Japanese Application JP 2005-028668 filed Feb. 4, 2005, the priority of each application is claimed and the contents of each application is incorporated herein by reference.

TECHNICAL FIELD

The present invention relates to a material for an organic electroluminescence element, an organic electroluminescence element, a display device and a lighting device.

BACKGROUND

As an emission type electronic displaying device, an electroluminescence device (hereinafter, referred to as ELD) is known. Elements constituting the ELD include an inorganic electroluminescence element and an organic electroluminescence element (hereinafter referred to also as an organic EL element). Inorganic electroluminescence element has been used for a plane light source, however, a high voltage alternating current has been required to drive the element. An organic EL element has a structure in which an emission layer containing a light emitting compound is arranged between a cathode and an anode, and an electron and a hole were injected into the emission layer and recombined to form an exciton. The element emits light, utilizing light (fluorescent light or phosphorescent light) generated by inactivation of the exciton, and the element can emit light by applying a relatively low voltage of several volts to several tens of volts. The element has a wide viewing angle and a high visuality since the element is of self light emission type. Further, the element is a thin, complete solid element, and therefore, the element is noted from the viewpoint of space saving and portability.

A practical organic EL element to be used in the future is required to emit light of high luminance with a high efficiency at a lower power.

For example, in Japanese Patent No. 3093796, disclosed is an organic EL element exhibiting higher luminance of emitting light with a longer life in which a stilbene derivative, a distyrylarylene derivative or a tristyrylarylene derivative doped with a slight amount of a fluorescent compound is employed.

In Japanese Patent Pubilcation Open to Public Inspection (hereafter referred to as JP-A) No. 63-264692, disclosed is an element which has an organic emission layer containing 8-hydroxyquinoline aluminum complex as a host compound doped with a slight amount of a fluorescent compound. In JP-A No. 3-255190, disclosed is an element which has an organic emission layer containing 8-hydroxyquinoline aluminum complex as a host compound doped with a quinacridone type dye.

When light emitted through excited singlet state is used in the element disclosed in the above Patent documents, the upper limit of the external quantum efficiency ($\eta$ext) is considered to be at most 5%, because the generation probability of excited species capable of emitting light is 25%, since the generation ratio of singlet excited species to triplet excited species is 1:3, and further, external light emission efficiency is 20%.

Since an organic EL element, employing phosphorescence through the excited triplet, was reported by Princeton University (see M. A. Baldo et al., Nature, 395, 151-154(1998)), studies on materials emitting phosphorescence at room temperature have been actively carried. Such an examples include those reported in M. A. Baldo et al., Nature, 403(17), 750-753(2000) and disclosed in U.S. Pat. No. 6,097,147.

As the upper limit of the internal quantum efficiency of the excited triplet is 100%, the light emission efficiency of the exited triplet is theoretically four times that of the excited singlet. Accordingly, light emission employing the excited triplet exhibits almost the same performance as a cold cathode tube, and can be applied to a lighting device. For example, many kinds of heavy metal complexes such as iridium complexes have been synthesized and studied, for example reported in S. Lamansky et al., J. Am. Chem. Soc., 123, 4304 (2001).

An example employing tris(2-phenylpyridine)iridium as a dopant has been studied in the abovementioned M. A. Baldo et al., Nature, 403(17), 750-753(2000).

As other examples, M. E. Tompson et al. have reported, in The 10th International Workshop on Inorganic and Organic Electroluminescence (EL '00, Hamamatsu), a dopant $L_2Ir$ (acac) such as $(ppy)_2Ir(acac)$, and Moon-Jae Youn. Og, Tetsuo Tsutsui et al., have reported results of an examination using, for example, tris(2-(p-tolyl)pyridine)iridium $(Ir(ptpy)_3)$ or tris(benzo[h]quinoline)iridium $(Ir(bzq)_3)$ as a dopant, also in The 10th International Workshop on Inorganic and Organic Electroluminescence (EL '00, Hamamatsu). An example of preparing an element using varieties of iridium complexes has also been reported in abovementioned S. Lamansky et al., J. Am. Chem. Soc., 123, 4304 (2001).

A hole transport material has been used as a host of a phosphorescent compound in order to increase emission efficiency as has been reported by Ikai et al. in The 10th International Workshop on Inorganic and Organic Electroluminescence (EL '00, Hamamatsu). M. E. Thompson et al. have used varieties of electron transport materials as a host material of a phosphorescent compound and have doped a novel iridium complex into the host materials.

An ortho-metalated complex having platinum as a center metal instead of iridium has also attracted attention. Many examples of such complexes having a characteristic ligand have been known.

In any cases, luminance of the emitted light and light emission efficiency of the light emission element are largely improved compared with usual element because the emitted light is originated in phosphorescent light. It has been known that shifting the emitting light wave length to shorter side can be attained by introducing an electron-attractive group such as a fluorine atom, a trifluoromethyl group and a cyano group to the phenylpyridine and introducing a ligand such as picolinic acid and a pyrazabole type ligand; (cf. Non Patent Documents 1 to 3). However, the cut off of on the long wavelength side of the spectrum of the light emitted from such the element is broad so that the purity of color of the light is considerably lowered. Consequently, improvement of the color purity of blue light is particularly demanded. In the high efficiency phosphorescent light emitting element, the emitting light is difficultly shifted to shorter side and difficultly improved in the color purity. Therefore, properties sufficiently acceptable for practical use are not obtained yet.

A platinum complex having a tricyclic ligand which is constituted by aromatic rings each directly bonded at meta-position thereof has been know; cf. Patent Documents 1 and 2 and Non-patent Document 4 for example. The sharpness of cutting off at the long wavelength end of the spectrum is improved in the element using such the compound so that improvement in the color purity is observed depending on the kind of the substituent. In the present condition, the shifting of the emitted light to the shorter wavelength side is difficultly realized as long as the compound has the structure constituting directly bonded three aromatic rings.

Patent Document 1: International Publication 04/039781 Pamphlet

Patent Document 2: JP A 2003-73355

Non-patent Document 1: Inorganic Chemdstry, 41, 12, pp. 3055-3066

Non-patent Document 2: Applied Physics Letters, 79, P. 2082

Non-patent Document 3: Applied Physics Letters, 83, P. 3813

Non-patent Document 4: Inorganic Chemistry, 43, 6, pp. 1950-1956

DISCLOSURE OF THE INVENTION

Problems to be Solved by the Invention

The present invention is accomplished on the above background, and the object of the invention is to provide an organic EL element having high light emission efficiency and high color purity, and a lighting device and a displaying device using the organic EL element.

Means for Solving the Problems

The above objects of the invention can be attained by the following constitution.

1. An electroluminescence element material having a metal complex represented by the following Formula 1 or an isomer thereof as a part of the structure thereof.

Formula 1

In the above formula, $Z_{01}$, $Z_{02}$ and $Z_{03}$ are each a group of atoms necessary for forming an aromatic hydrocarbon ring or an aromatic heterocyclic ring together with the $N_{01}$-$B_{01}$ bond, the $B_{02}$-$B_{03}$ bond and the $C_{01}$-$A_{01}$-$C_{02}$ bond, respectively. $A_{01}$, $B_{01}$, $B_{02}$ and $B_{03}$ are each a carbon atom or a nitrogen atom. $N_{01}$ is a nitrogen atom. $L_{01}$ and $L_{02}$ are each a di-valent bonding group. $M_{01}$ is a metal of Groups 8 to 10 in the periodic table. The bonding between $A_{01}$ and $M_{01}$, $B_{01}$ and $M_{01}$ and $B_{02}$, and $M_{01}$ are each a covalent bond or a coordinate bond.

2. An electroluminescence element material having a metal complex represented by the following Formula 2 or an isomer thereof as a part of the structure thereof.

Formula 2

In the above formula, $Z_{11}$, $Z_{12}$ and $Z_{13}$ are each a group of atoms necessary for forming an aromatic hydrocarbon ring or an aromatic heterocyclic ring together with the $N_1$-$B_1$ bond, the $N_2$-$B_2$ bond and the $C_1$-$A_{11}$-$C_2$ bond, respectively. $A_{11}$, $B_1$, and $B_2$ are each a carbon atom or a nitrogen atom. $N_1$ and $N_2$ are each a nitrogen atom. $L_1$ and $L_2$ are each a di-valent bonding group. $M_{11}$ is a metal of Groups 8 to 10 in the periodic table. The bonding between $A_{11}$ and $M_{11}$, $B_1$ and $M_{11}$, and $B_2$ and $M_{11}$ are each a covalent bond or a coordinate bond.

3. An electroluminescence element material having a metal complex represented by the following Formula 3 or an isomer thereof as a part of the structure thereof.

Formula 3

In the above formula, $Z_{21}$ and $Z_{22}$ are each a group of atoms necessary for forming an aromatic hydrocarbon ring or an aromatic heterocyclic ring together with the $N_3$—$B_3$ bond and the $N_4$—$B_4$ bond, respectively. $A_{21}$, $A_{22}$, $A_{23}$, $A_{24}$, $B_3$ and $B_4$ are each a carbon atom or a nitrogen atom. $N_3$ and $N_4$ are each a nitrogen atom. $L_3$ and $L_4$ are each a di-valent bonding group. $M_{12}$ is a metal of Groups 8 to 10 in the periodic table. The bonding between $A_{24}$ and $M_{12}$, $B_3$ and $M_{12}$, and $B_4$ and $M_{12}$ are each a covalent bond or a coordinate bond.

4. An electroluminescence element material having a metal complex represented by the following Formula 4 or an isomer thereof as a part of the structure thereof.

Formula 4

In the above formula, $A_{31}$, $A_{32}$, $A_{33}$, $Y_{31}$, $Y_{32}$, $Y_{33}$, $Y_{34}$, $Y_{35}$ and $Y_{36}$ are each a carbon atom or a nitrogen atom, $M_{13}$ is a metal of Groups 8 to 10 in the periodic table. $L_5$ and $L_6$ are each a divalent bonding group.

5. An electroluminescence element material having a metal complex represented by the following Formula 5 or an isomer thereof as a part of the structure thereof.

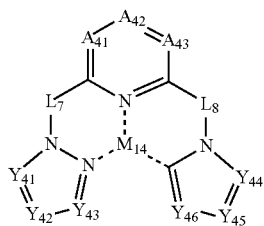

Formula 5

In the above formula, $A_{41}$, $A_{42}$, $A_{43}$, $Y_{41}$, $Y_{42}$, $Y_{43}$, $Y_{44}$, $Y_{45}$ and $Y_{46}$ are each a carbon atom or a nitrogen atom. $M_{14}$ is a metal of Groups 8 to 10 in the periodic table. $L_7$ and $L_8$ are each a divalent bonding group.

6. An electroluminescence element material having a metal complex represented by the following Formula 6 or an isomer thereof as a part or the structure thereof.

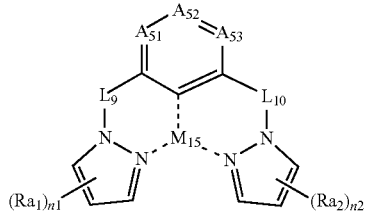

Formula 6

In the above formula, $A_{51}$, $A_{52}$ and $A_{53}$ are each a carbon atom or a nitrogen atom. $M_{15}$ is a metal of Groups 8 to 10 in the periodic table. $L_9$ and $L_{10}$ are each a divalent bonding group. $Ra_1$ and $Ra_2$ are each a hydrogen atom or a substituent, and $n_1$ and $n_2$ are each an integer of from 0 to 3.

7. An electroluminescence element material having a metal complex represented by the following Formula 7 or an isomer thereof as a part of the structure thereof.

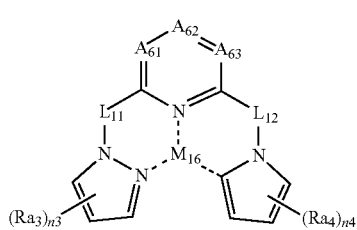

Formula 7

In the above formula, $A_{61}$, $A_{62}$ and $A_{63}$ are each a carbon atom or a nitrogen atom. $M_{16}$ is a metal of Groups 8 to 10 in the periodic table. $L_{11}$ and $L_{12}$ are each a divalent bonding group. $Ra_3$ and $Ra_4$ are each a hydrogen atom or a substituent, and $n_3$ and $n_4$ are each an integer of from 0 to 3.

8. An electroluminescence element material described in any one of the above 1 to 7, wherein the metal of Groups 8 to 10 of the periodic table is platinum or iridium.

9. An electroluminescence element material described in any one of the above 1 to 7, wherein the metal of Groups 8 to 10 of the periodic table is platinum.

10. An electroluminescence element material described in any one of the above 1 to 7, wherein the metal of Groups 8 to 10 of the periodic table is iridium.

11. An organic electroluminescence element, wherein a layer constituting the organic electroluminescence element contains the electroluminescence element material described in any one of the above 1 to 7.

12. The organic electroluminescence element described in the above 11, wherein the element has a light emission layer as the element constituting layer and the light emission layer contains the organic electroluminescence element material described in any one of the above 1 to 10.

13. The organic electroluminescence element described in the above 11 or 12, wherein at least one of the layers constituting the organic electroluminescence element contains a carbazole compound or a compound represented by the following Formula I.

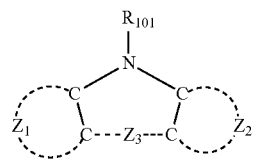

Formula I

In the above formula, $Z_1$ is a group of atoms for forming an aromatic heterocyclic ring, $Z_2$ is a group of atoms for forming an aromatic heterocyclic ring or an aromatic hydrocarbon ring, and $Z_3$ is a divalent bonding group or a single bond. $R_{101}$ is a hydrogen atom or a substituent.

14. A displaying device having the organic electroluminescence element described in any one of the above 11 to 13.

15. A lighting device having the organic electroluminescence element described in any one of the above 11 to 13.

Effects of the Invention

A material for an organic EL element material useful for an organic EL element can be obtained by the invention, and an organic EL element having high light emission efficiency and improved in the color purity, a lighting device and a displaying device can be provided by the invention.

DESCRIPTION OF SYMBOLS

Figure 1:
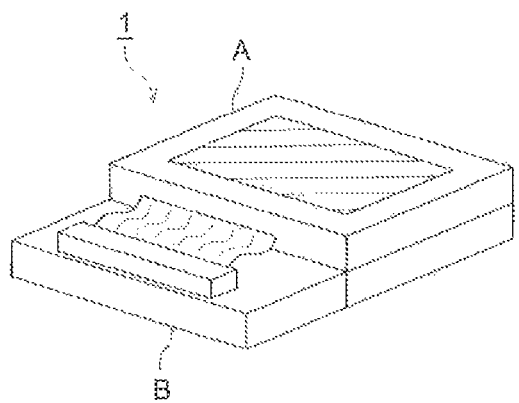
FIG. 1 is schematic drawing of an example of displaying device constituted by an Organic EL element.

1: Display
3: Pixel
5: Scanning line
6: Data line
7: Power source line
10: Organic EL element
11: Switching transistor
12: Driving transistor
13: Condenser
A: Displaying means
B: Controlling means 102: Glass cover
105: Cathode
106: Organic EL layer
107: Glass substrate with a transparent electrode
103: Nitrogen gas
109: Moisture collector

THE BEST EMBODIMENT FOR EMBODYING THE INVENTION

In the organic EL element of the invention, the molecular of the material for an organic EL element constituted according to the definition described in any one of the above 1 to 10 can be designed. The organic EL element having high light emission efficiency and improved color parity defined by any one of the above 11 to 13, the lighting device defined by any one of the above 14 and 15 and the displaying device can be provided by the use of the material for an organic EL element.

As a result on investigation on the above problems by the inventors, it is found that the control of the wavelength of the emitted light and the light emission efficiency can be made compatible by using a metal complex having a specified ligand. As to control of the wavelength of the emitting light, the emitting light becomes green to red when the aromatic rings are directly bonded at the meta-position by the aromatic ring. Contrary to that, the wavelength can be controlled so as to be blue having shorter wavelength by bonding the aromatic rings through the bonding group as shown in Formulas 1 to 7. Formulas 1 to 7 are characterized in that at least one of the aromatic rings substituted through the bonding group is bonded at the nitrogen atom.

It is found that the problem of color purity of usual blue light emitting organic EL elements produced by an organic EL element material in which the wavelength of emitting light is controlled to be short only by an electron attractive group can be considerably improved by the organic EL element containing the metal complex having the specified partial structure as the material for an organic EL element.

For designing a molecule for making the emitting light of the metal complex to longer wavelength region by introducing a substituent emitting longer wavelength light, a suitable partial structured can be selected from the fundamental skeleton of the compounds represented by Formulas 1 to 7 or isomer of them of the invention.

Each of the constituting elements of the invention is described in detail below.

<<Metal Complex>>

Metal complex relating to the material for an organic EL element of the invention is described below.

The layer containing the material for an organic EL element which contains a metal complex represented by each of Formulas 1 to 7 or the isomer of the complex represented by Formula 1 to 7 of the invention as the partial structure thereof is preferably the light emission layer. When the material for an organic EL element is contained in the light emission layer, the external quantum efficiency (rising in the luminance) and the color purity of the organic EL element of the invention can be improved by the use of the compound as a dopant.

In Formula 1, $Z_{01}$, $Z_{02}$ and $Z_{03}$ are each a group of atoms necessary for forming an aromatic hydrocarbon ring or an aromatic heterocyclic ring together with the $N_{01}$—$B_{01}$ bond, the $B_{02}$—$B_{03}$ bond and the $C_{01}$—$A_{01}$—$C_{02}$ bond, respectively. The above aromatic hydrocarbon ring and the aromatic heterocyclic ring may have a substituent. Examples of the aromatic hydrocarbon ring include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthene ring, a naphthacene ring, a pentacene ring, a perylene ring, a pentaphene ring, a picene a pyrene ring, a pyranthrene ring and an anthanthrene ring, and examples of the aromatic heterocyclic ring include a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, at thiazole ring, an indole ring, a benzimidazole ring, a benxothiazole ring, a benxoxazole ring, a quinoxaline ring, a quinazoline ring, a phthalazine ring, a carbazole ring, a carboline ring and a diazacarbazole ring, namely a ring formed by further substituting a carbon atom of the hydrocarbon group constituting a carboline ring by a nitrogen atom.

Examples of the substituent capable of substituting to the aromatic hydrocarbon ring or the aromatic heterocyclic ring include an alkyl group such as a methyl group, an ethyl group, a propyl group, a tert-butyl group, a pentyl group, a hexyl group, an octyl group, at dodecyl group, a tridecyl group, a tetradecyl group and a pentadecyl group; a cycloalkyl group such as a cyclopentyl group and a cyclohexyl group: an alkenyl group such as a vinyl group and an allyl group, an alkynyl group such as an ethynyl group and a propargyl group; an aryl group such as a phenyl group and a naphthyl group; an aromatic heterocyclic group such as a furyl group, a thienyl group, a pyridyl group, a pyridazinyl group, a pyrimidinyl group, at pyrazinyl group, a triazinyl group, an imidazolyl group, a pyrazolyl group, a thiazolyl group, a quinazolinyl group and a phthalazinyl group; a heterocyclic group such as a pyrrolidinyl group, an imidazolidyl group, a morpholyl group and a oxazolidyl group; an alkoxyl group such as a methoxy group, an ethoxy group, a propyloxy group, a pentyloxy group, an octyloxy group and a dodecyloxy group; a cycloalkoxyl group such as a cyclopentyloxy group and a cyclohexyloxy group; an aryloxy group such as a phenoxy group and a naphthyloxy group; an alkylthio group such as a methylthio group, an ethylthio group, a propylthio group, a pentylthio group, a hezylthio group, an octylthio group and a dodecylthio group; a cycloalkylthio group such as a cyclopentylthio group and a cyclohexylthio group; an arylthio group such as a phenylthio group and a naphthylthio group; an alkoxycarbonyl group such as a methyloxycarbonyl group, an ethyloxycarbonyl group, a butyloxycarbonyl group, an octyloxycarbonyl group and a dodecyloxycarbonyl group; an aryloxycarbonyl group such as a phenylozycarbonyl group and a naphthyloxycarbonyl group; a sulfamoyl group such as an aminosalfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group and a 2-pyridylaminosulfonyl group; an acyl group such as an acetyl group, an ethylcarbonyl group, a propylcarbonyl group, a pentylcarbonyl group, a cyclohexylcarbonyl group, an octylcarbonyl group, a 2-ethylhexyl group, a dodecylcarbonyl group, a phenylcarbonyl group, a naphthylcarbonyl group and a pyridylcarbonyl group; an acyloxy group such as an acetyloxy group, an ethylcarbonyloxy group, a butylcarbonyloxy group, an octylcarbonyloxy group, a dodecylcarbonyloxy group and a phenylcarbonyloxy group; an amino group such as a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group and a naphthylcarbonylamino group; a carbamoyl group such as an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group and a 2-pyridylaminocarbonyl group; a ureido group such as a methylureido group, an ethylureido group, a pentylureido group, a cyclohexylureido group, an octylureido group, a dodecylureido group, a phenylureido group, a naphthylureido group and a 2-pyridylaminoureido group; a sulfinyl group such as a methylsulfinyl group, an ethylsulfinyl group, a butylsulfinyl group, a cyclohexyl group, a 2-ethylhexyl group, a dodecylsulfinyl group, a phenylsulfinyl group, a naphthylsulfinyl group; and a 2-pyridylsulfinyl group; an alkylsulfonyl group such as a methylsulfonyl group, an ethylsulfonyl group, a butylsulfonyl group, a cyclohexylsulfonyl group, a 2-ethylhexylsulfonyl group and a dodecyl-sulfonyl group; an arylsulfonyl group such as a phenylsulfonyl group, a naphthylsulfonyl group and a 2-pyridylsulfonyl group; an amino group; such as an amino group, an ethylamino group, a dimethylamino group, a butylamino group, a cyclopentylamino group, a 2-ethylhexylamino group, a dodecylamino group, an anilino group, a naphthylamino group and a 2-pyridylamino group; a halogen atom such as a fluorine atom, a chlorine atom and a bromine atom; a fluorohydrocarbon group such aa a fluoromethyl group, a trifluoromethyl group, a pentafluoroethyl group and a pentafluorophenyl group; a cyano group; a nitro group; a hydroxyl group; a mercapto group; and a silyl group such as a trimethylsilyl group, a triisopropylsilyl group, a triphenylsilyl group and a phenyldiethylsilyl group. These substituents may be further substituted by the above substituents. A plurality of these substituents may be bonded with together to form a ring.

The divalent bonding group represented by $L_{01}$ or $L_{02}$ is a hydrocarbon group such as an alkylene group, an alkenylene group, alkynylene group and arylene group, and may be one containing a halogen atom or a divalent group derived from a compound having an aromatic heterocyclic ring (also called as a heteroaromatic compound) such as a thiophene-2,5-diyl group and a pyrazine-2,3-diyl group, or a chalcogen atom such as an oxygen atom and a sulfur atom. Moreover, the bonding group may be a group bonding through a hetero atom such as an alkylimino group, a dialkylsilane-diyl group and a diarylgermane-diyl group.

$A_{01}, A_{02}, B_{01}$ and $B_{02}$ are each a carbon atom or a nitrogen atom and $N_{01}$ is a nitrogen atom.

In Formula 2, $Z_{11}, Z_{12}$ and $Z_{13}$ are each synonymous with $Z_{01}, Z_{02}$ and $Z_{03}$ in Formula 1. $A_{11}, B_1$ and $B_2$ are each a carbon atom or a nitrogen atom and $N_1$ and $N_2$ are each a nitrogen atom.

In Formula 3, $Z_{21}, Z_{22}$ and $Z_{13}$ are each synonymous with $Z_{01}, Z_{02}$ and $Z_{03}$ in Formula 1. $A_{21}, A_{22}, A_{23}, A_{24}, B_3$ and $B_4$ are each a carbon atom or a nitrogen atom and $N_3$ and $N_4$ are each a nitrogen atom.

In Formula 4, $A_{31}, A_{32}, A_{33}, Y_{31}, Y_{32}, Y_{33}, Y_{34}, Y_{35}$ and $Y_{36}$ are each a carbon atom or a nitrogen atom.

In Formula 5, $A_{41}, A_{42}, A_{43}, Y_{41}, Y_{42}, Y_{43}, Y_{44}, Y_{45}$ and $Y_{46}$ are each a carbon atom or a nitrogen atom.

In Formula 6, $A_{51}, A_{52}$ and $A_{53}$ are each a carbon atom or a nitrogen atom. $Ra_1$ and $Ra_2$ are each a hydrogen atom or a substituent which is synonymous with the substituent cited as to $Z_{01}, Z_{02}$ and $Z_{03}$ in Formula 1. n1 and n2 are each an integer of from 0 to 3.

In Formula 7, $A_{61}, A_{62}$ and $A_{63}$ are each a carbon atom or a nitrogen atom. $Ra_3$ and $Ra_4$ are each a hydrogen atom or a substituent which is synonymous with the substituent cited as to $Z_{01}, Z_{02}$ and $Z_{03}$ in Formula 1. n3 and n4 are each an integer of from 0 to 3.

In Formula 2, 3, 4, 5, 6 and 7, the divalent bonding group represented by $L_1, L_2, L_3, L_4, L_5, L_6, L_7, L_8, L_9, L_{10}, L_{11}$ or $L_{12}$, is synonymous with $L_{01}$ and $L_{02}$ in Formula 1.

In Formula 2, 3, 4, 5, 6 and 7, $M_{01}, M_{11}, M_{12}, M_{13}, M_{14}, M_{15}$ or $M_{16}$ are each a metal of Groups 8 to 10 of the periodic table and preferably Pt, Ir, Pd or Rh, and more preferably Pt or Ir.

The structures Formulas 1 to 7 are each a partial structure and a ligand corresponding to the valent number of the central metal is necessary for forming the complete structure of the material organic EL element. Concrete examples of the ligand include a halogen atom such as a fluorine atom, a chlorine atom, a bromine atom and an iodine atom, an aryl group such as a phenyl group, a p-chlorophenyl group, a mesityl group, a tolyl group, a xylyl group, a biphenyl group, a naphthyl group, an anthryl group and a phenanthryl group; an alkyl group such as a methyl an ethyl group, an isopropyl group, a hydroxyethyl group, a methoxymethyl group, a trifluoromethyl group and a t-butyl group, a an alkyloxy group, an aryloxy group, an alkylthio group, an arylthio group, an aromatic heterocyclic group such as a furyl group, a thienyl group, a pyridyl group, a pyridazinyl group, a pyrimidyl group, a pyrazinyl group, a triazinyl group, a imidazolyl group, a pyrazolyl group, a thiazolyl group, a quinazolyl group, a carbazolyl group, a carbolinyl group, a phthalazinyl group, and a partial structure formed by removing the metal atom from each of the structures represented by Formula 1 to 7.

Concrete exemplified compounds of the material for an organic electroluminescence element each having the metal complex represented by Formula 1 to 6 or 7, or isomers thereof are shown below.

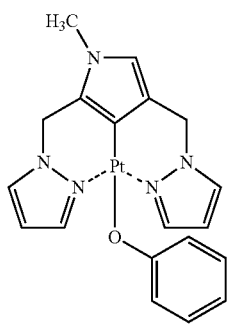

1-1

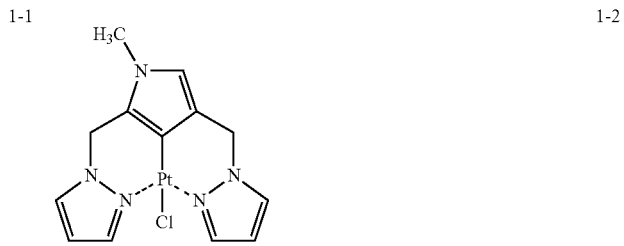

1-2

-continued
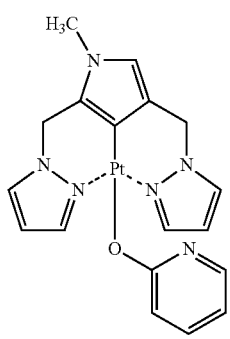
1-3
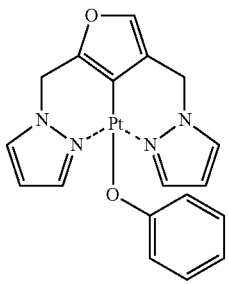
1-4
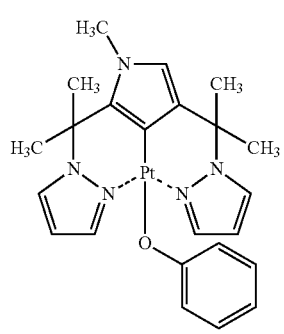
1-5
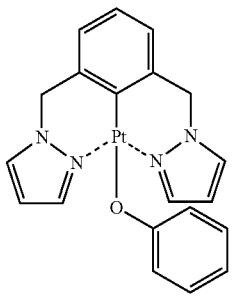
1-6
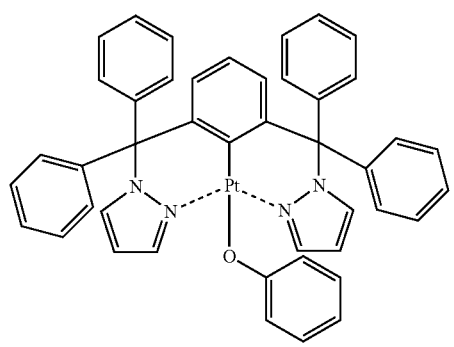
1-7
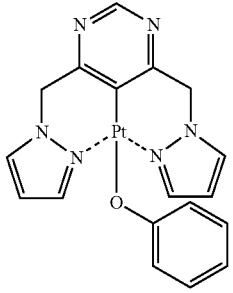
1-8
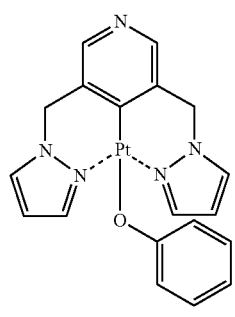
1-9
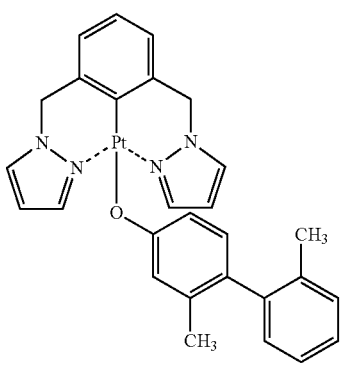
1-10

-continued
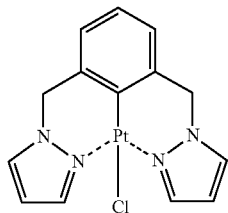
1-11
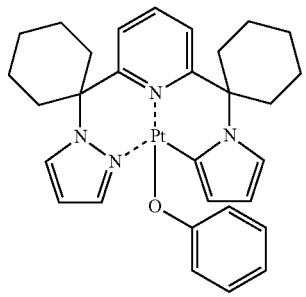
1-12
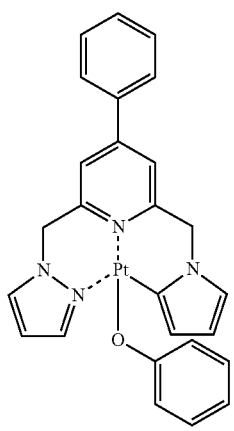
1-13
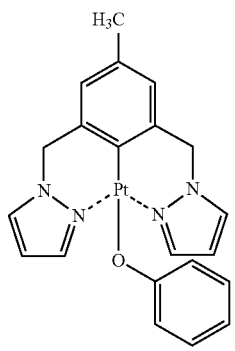
1-14
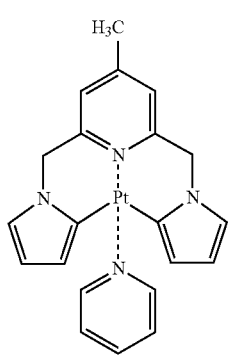
1-15
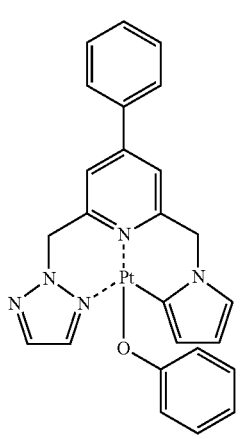
1-16
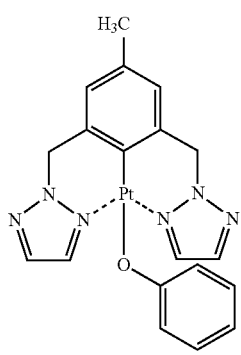
1-17
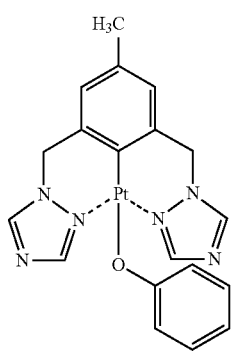
1-18

-continued
| | |
|---|---|
| 1-19 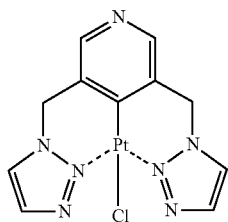 | 1-20 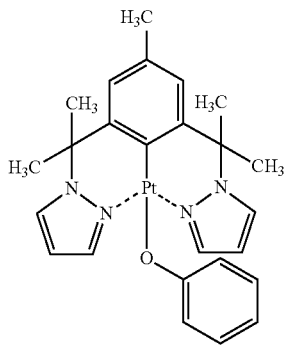 |
| 1-21 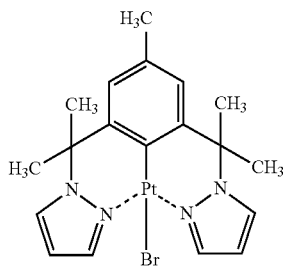 | 1-22 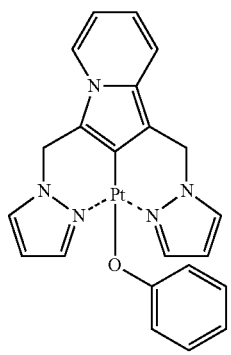 |
| 1-23 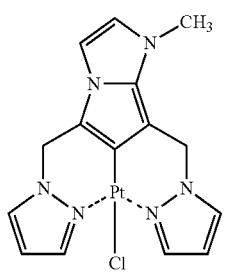 | 1-24 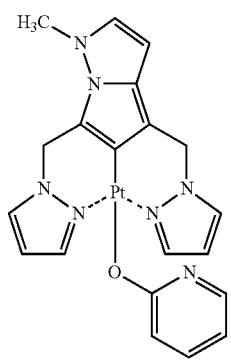 |
| 1-25 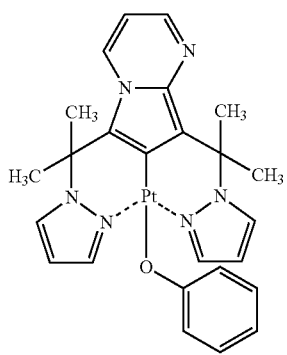 | 1-26 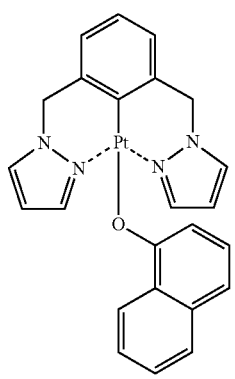 |

-continued
1-27
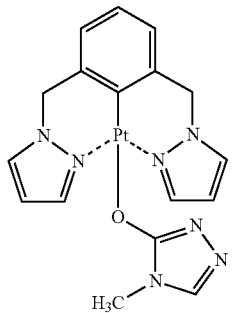
1-28
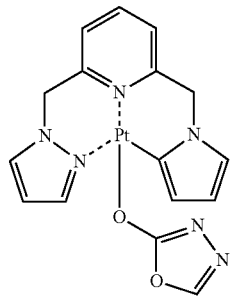
1-29
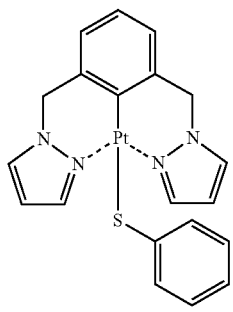
1-30
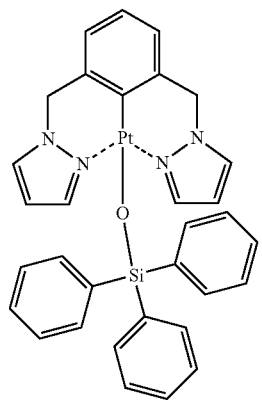
1-31
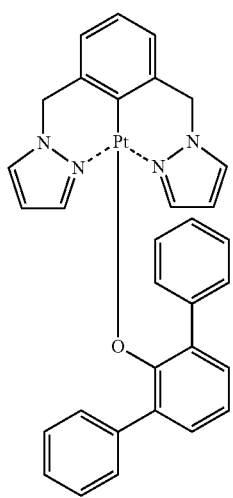
1-32
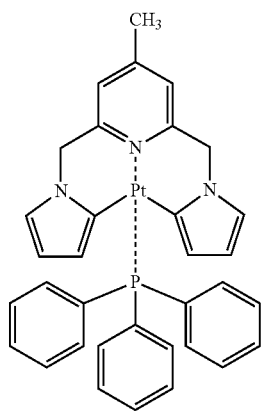

-continued
1-33
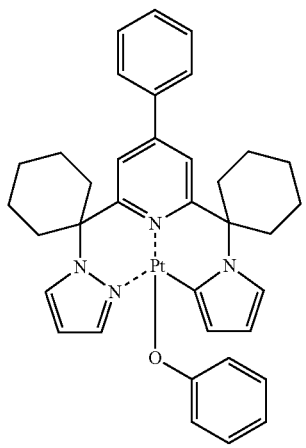
1-34
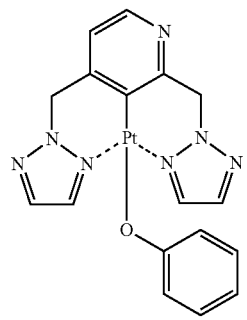
1-35
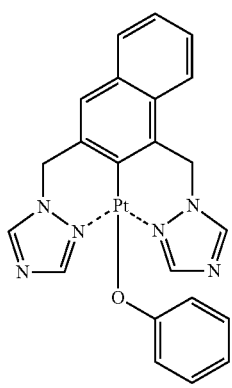
1-36
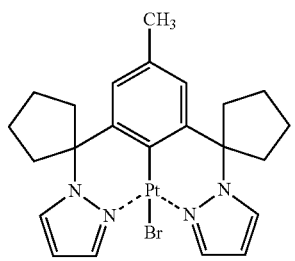
1-37
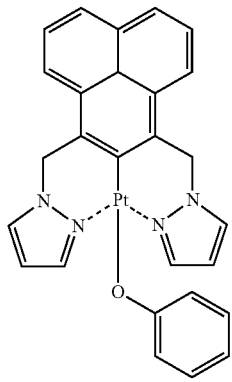
1-38
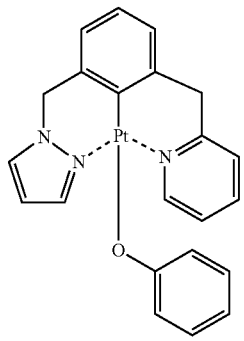
1-39
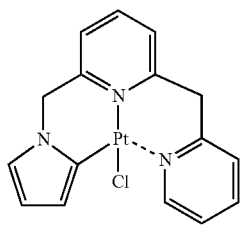
1-40
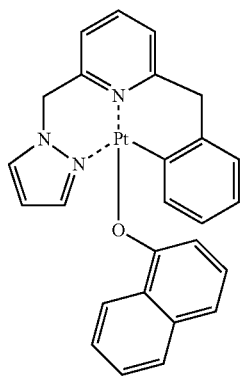

-continued
1-41
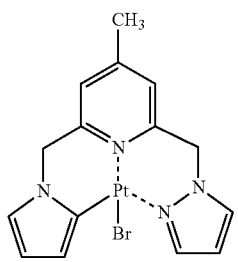
1-42
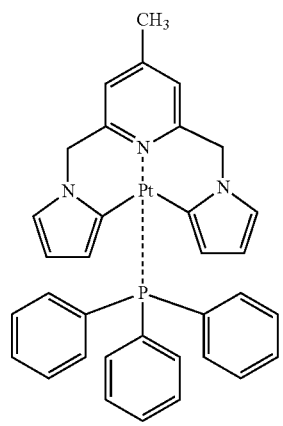
1-43
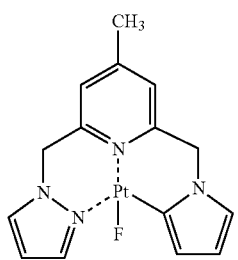
1-44
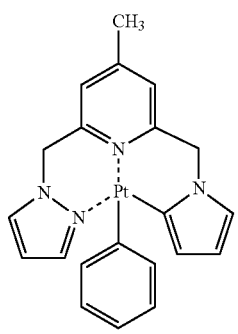
1-45
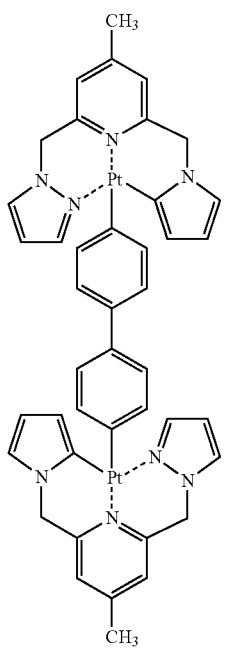
1-46
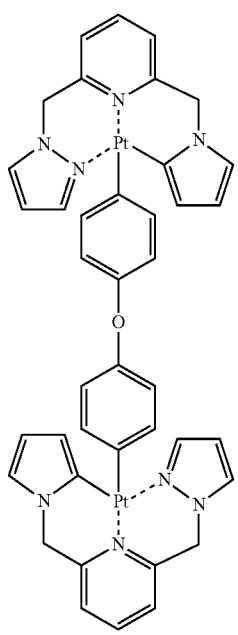

-continued
1-47
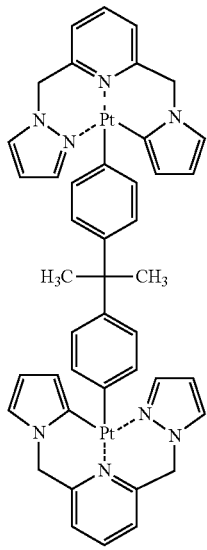
1-48
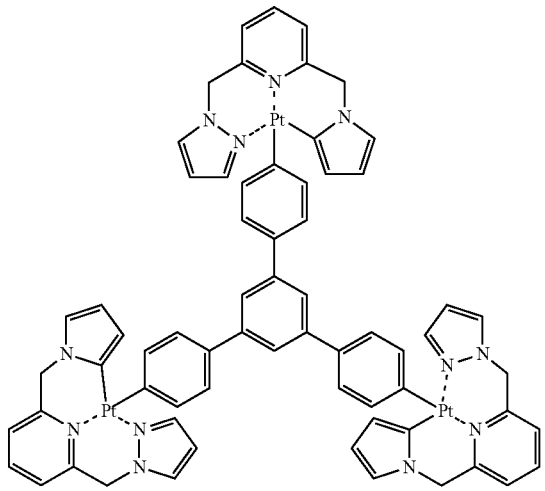
1-49
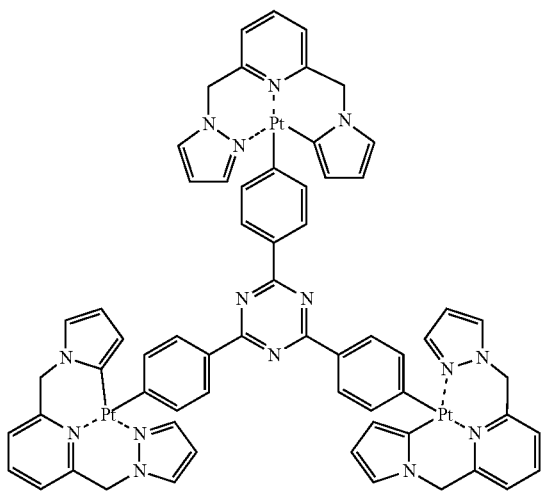
2-1
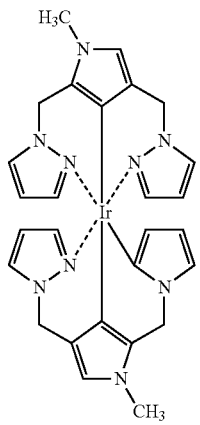
2-2
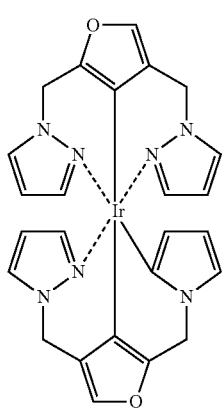
2-3
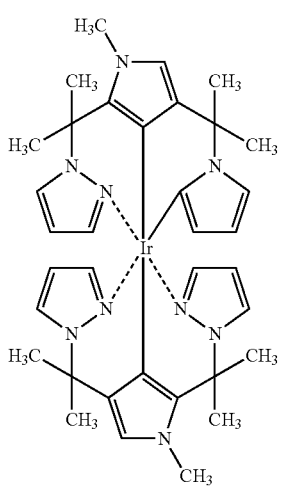

-continued
2-4
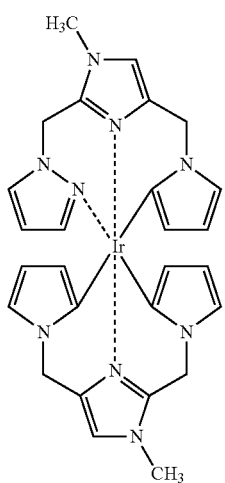
2-5
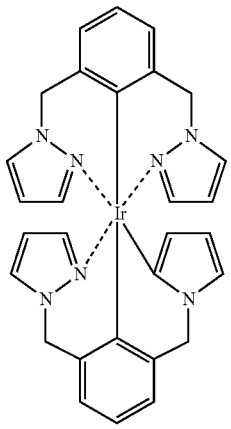
2-6
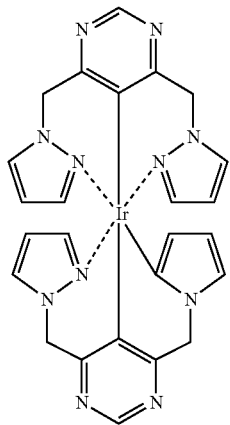
2-7
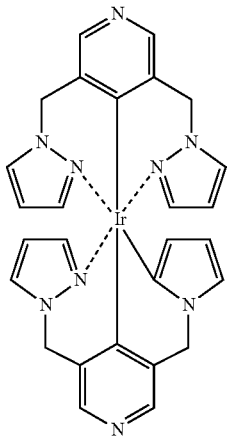
2-8
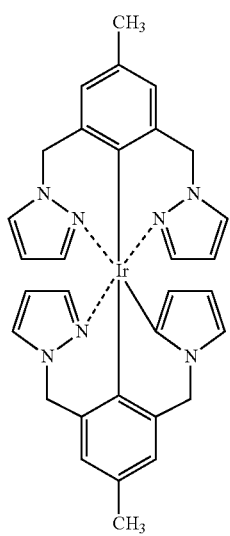
2-9
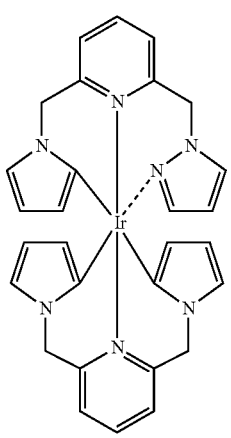

-continued
2-10
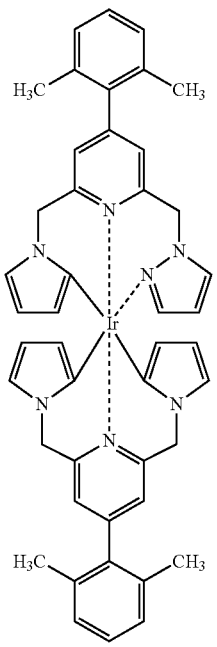
2-11
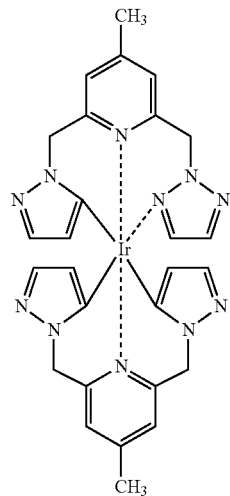
2-12
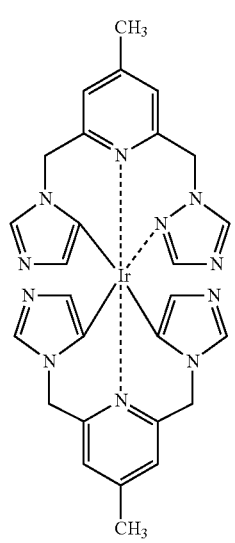
2-13
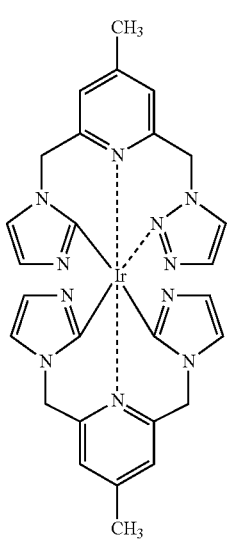

-continued
| | |
|---|---|
| 2-14 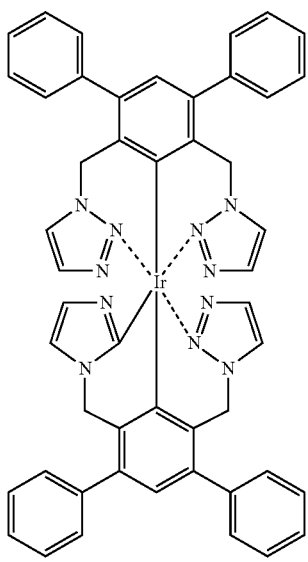 | 2-15 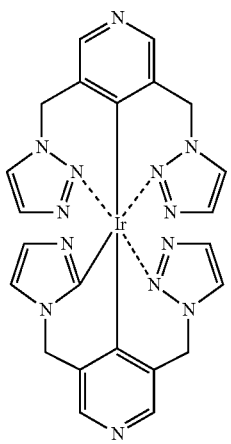 |
| 2-16 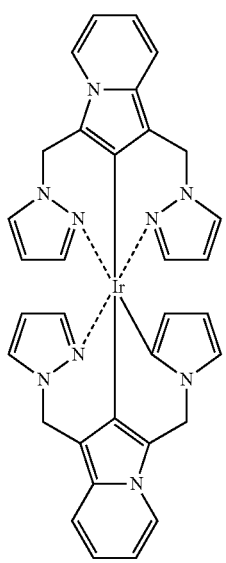 | 2-17 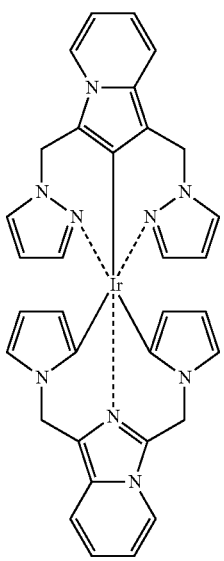 |
| 2-18 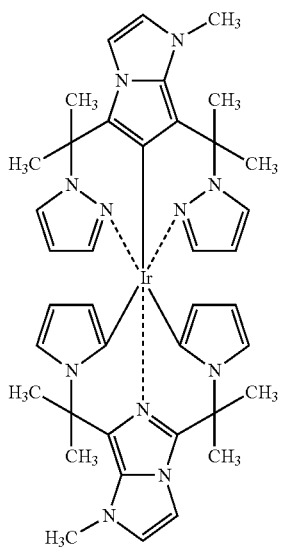 | 2-19 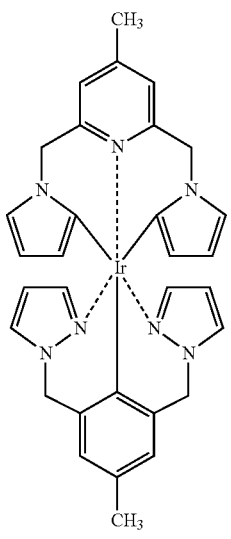 |

2-20
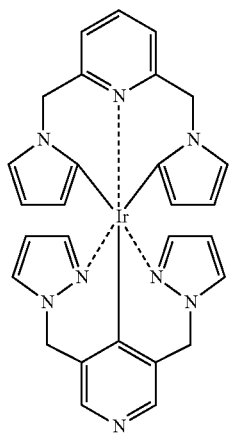
2-21
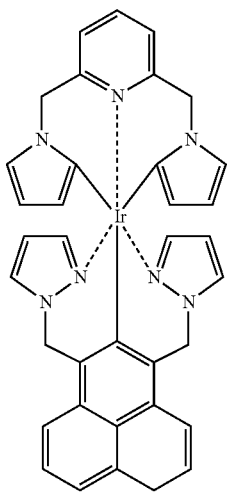
2-22
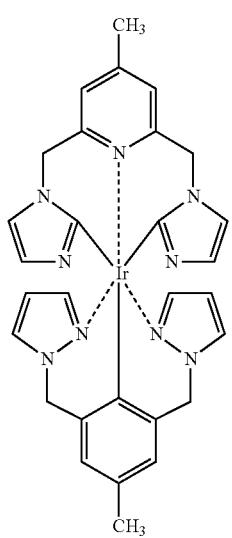
2-23
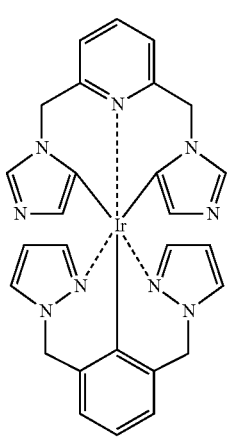
2-24
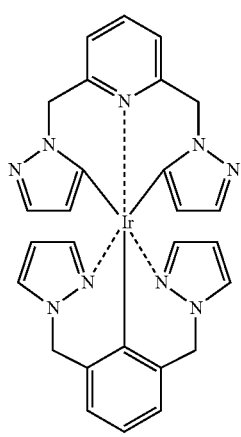
2-25
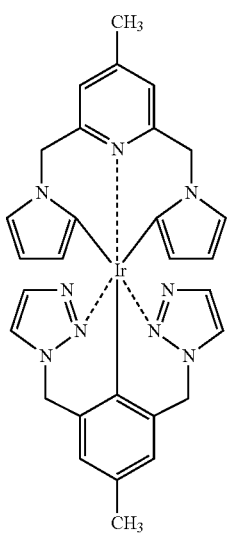

-continued
2-26
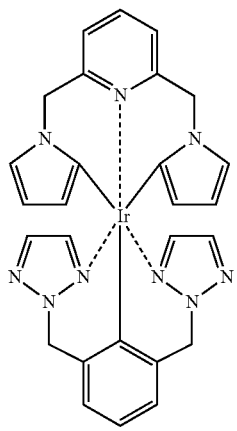
2-27
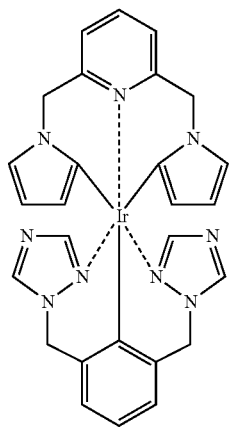
2-28
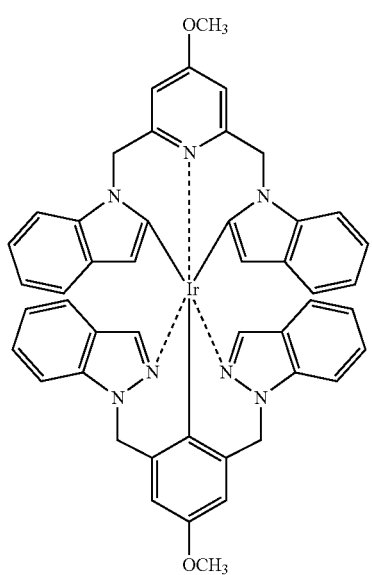
2-29
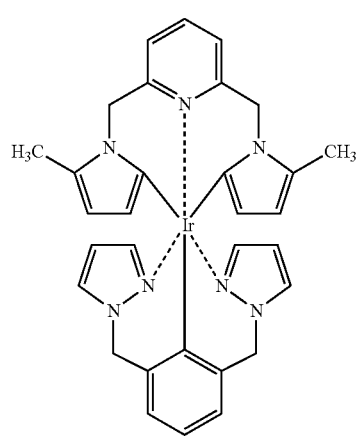
2-30
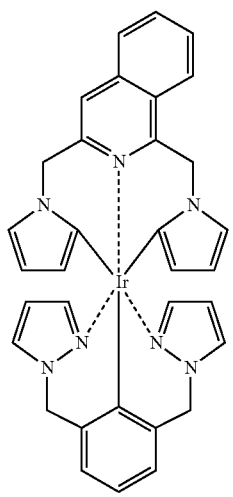
2-31
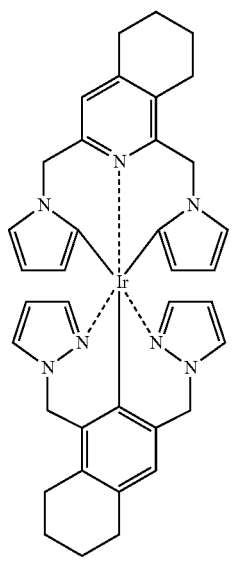

-continued
2-32
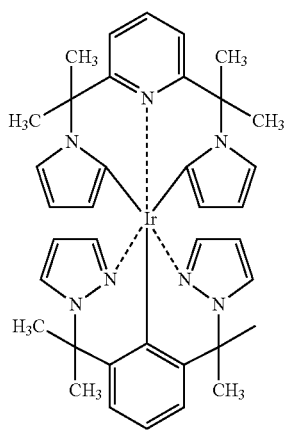
2-33
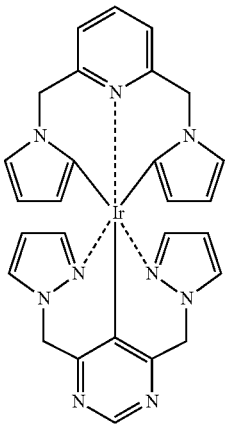
2-34
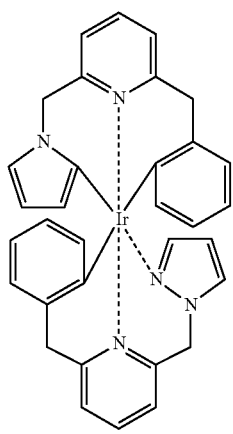
2-35
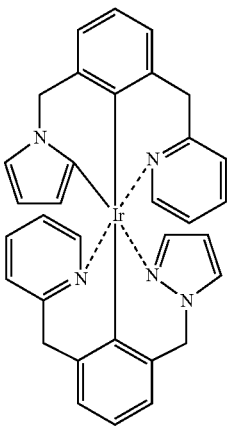
2-36
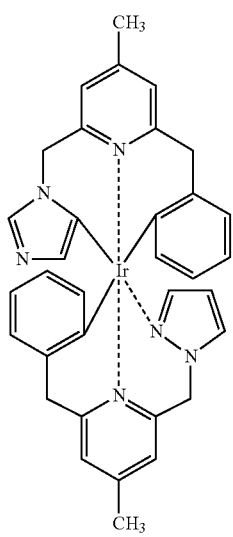
2-37
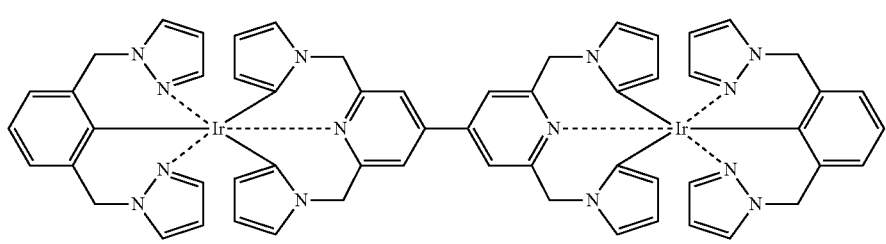

-continued 2-38

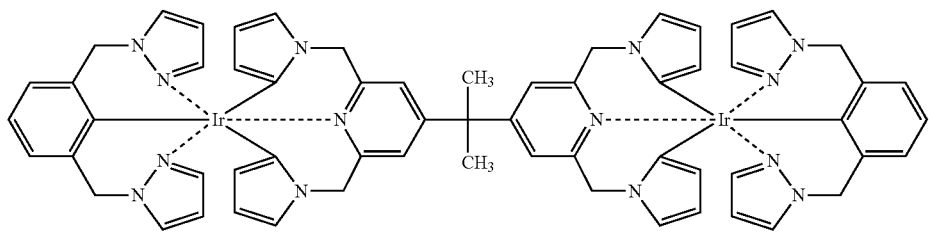

3-1

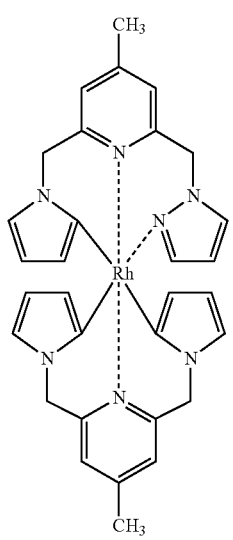

3-2

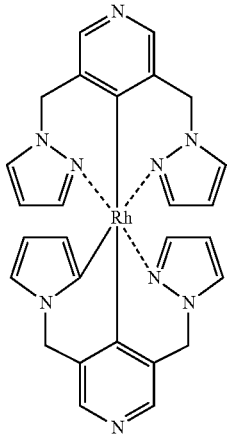

3-3

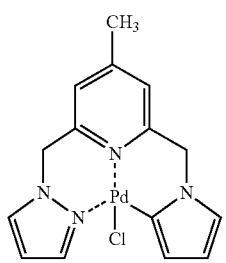

3-4

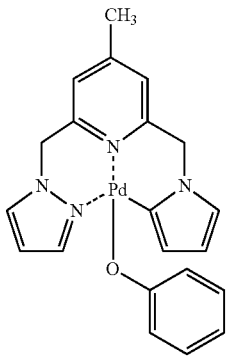

Synthesizing example of the exemplified compound is described bellow.

Synthesizing Example

Synthesis of Exemplified Compound 1-6

In 150 ml of dimethylformamide, 10.0 g of dibromometaxylene and 5.0 g of pyrazole were dissolved and then 9.0 g of tert-butoxy potassium was added. An acetone solution of 6.0 g of potassium iodide was further added and heated and stirred for 4 hours at 100° C. After cooling by room temperature, water and ethyl acetate was added to the reacting liquid for separating an organic liquid layer. The organic layer was dried by addition or magnesium sulfate and filtered. The filtrate was condensed under reduced pressure and thus obtained crude crystals were purified by column chromatography. Thus 5.2 g of Compound A was obtained.

To 100 ml of acetic acid, 6.0 g of potassium tetraplatinumacetate and 3.5 g of Compound A and heating and stirring for 5 hours at 80° C. The reacting liquid was cooled and thus formed reddish orange crystals were separated by filtration and washed by water and methanol, and then dried to obtain 1.5 g of Compound B. One point five grams of Compound B and 0.7 g of phenol were dissolved in dimethylformamide and heated and stirred for 5 hours. After cooled by room temperature, water and ethyl acetate was added to the reacting liquid for separating organic liquid layer. The organic layer was dried by addition of magnesium sulfate and filtered. The filtrate was condensed under reduced pressure and thus obtained crude crystals were purified by column chromatography. Thus 0.7 g of objective substance was obtained.

Compound A
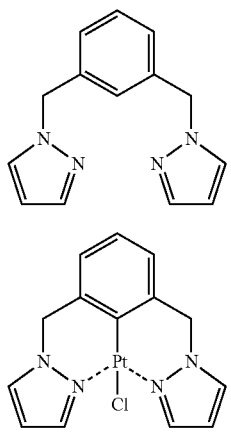
Compound B

Other than the above, the metal complexes relating to the material for an organic EL element of the invention can be synthesized by applying a method similar to the above ana the methods described in Patent Documents 1 and 2, Non-patent Documents 1 to 4 and the documents referred in such the documents.

<<Application of Organic EL Element Material to Organic EL Element>>

When producing an organic EL element using the organic EL element material of this invention, the organic EL element material is preferably used in the emission layer or in the hole blocking layer among the constituting layers (details will be described later). In the light emission layer, it is preferably used as an emission dopant as mentioned above.

(Emission Host and Emission Dopant)

The mixing ratio content of an emission dopant is preferably not less than 0.1% by weight but less than 30% by weight based on the weight of an emission host, the emission host being a host compound which is a main component of the emission layer.

The emission dopant may be a mixture of plural compounds which may be other metal complexes having different structures or may be a phosphorescent dopant or a fluorescence dopant having other structure.

A dopant (a phosphorescent dopant or a fluorescent dopant) which may be used together with a platinum complex used as an emission dopant will now be explained. The emission dopant is classified into a fluorescent dopant emitting a fluorescent light and a phosphorescent dopant emitting a phosphorescent light in general.

Typical examples of the former (a fluorescent dopant) include: a coumarin dye, a pyran dye, a cyanine dye, a croconium dye, a squarylium dye, an oxobenzanthracene dye, a fluoresceine dye, a rhodamine dye, a pyrylium dye, a perylene dye, a stilbene dye, a polythiophene dye, and a rare earth complex fluorescent material.

As typical examples of the latter (a phosphorescent dopant), preferable is a complex containing a metal of group 8, 9 or 10 in the periodic table of elements, and more preferable is an iridium compound, an osmium compound or an iridium compound. Of these, most preferable is an iridium compound. Specifically, preferable are the compounds disclosed in the following Patent Documents.

WO00/70655, JP-A Nos. 2002-280178, 2001-181616, 2002-280179, 2001-181617, 2002-280180, 2001-247859, 2002-299060, 2001-313178, 2002-302671, 2001-345183, 2002-324679, WO02/15645 JP-A Nos. 2002-332291, 2002-50484, 2002-332292, 2002-83684, Published Japanese Translation of PCT International Application Publication No. 2002-540572, JP-A Nos. 2002-117978, 2002-338588, 2002-170684, 2002-352960, WO 01/93642, JP-A Nos. 2002-50483, 2002-100476, 2002-173674, 2002-359082, 2002-175884, 2002-353552, 2002-184582, 2003-7469, Published Japanese Translation of PCT International Publication No. 2002-525808, JP-A No. 2003-7471, Published Japanese Translation of PCT International Publication No. 2002-525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678.

A part of the examples will be shown below.

Pt-1
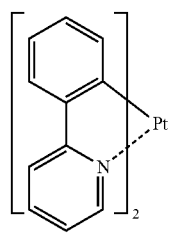

Pt-2
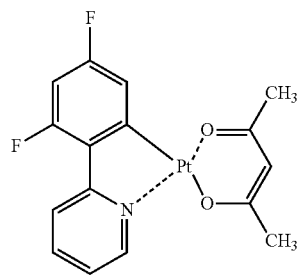

Pt-3
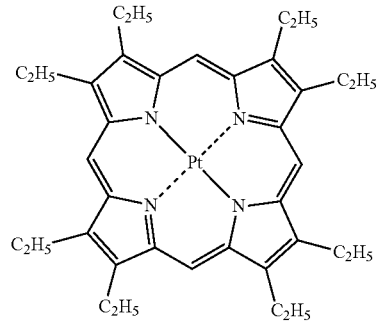

A-1
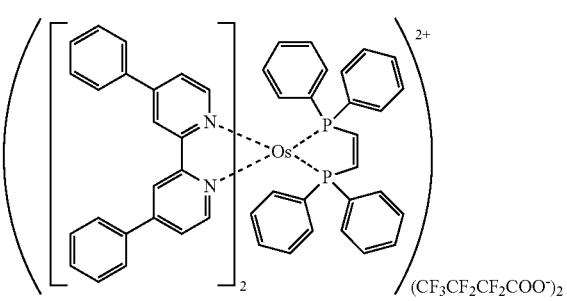

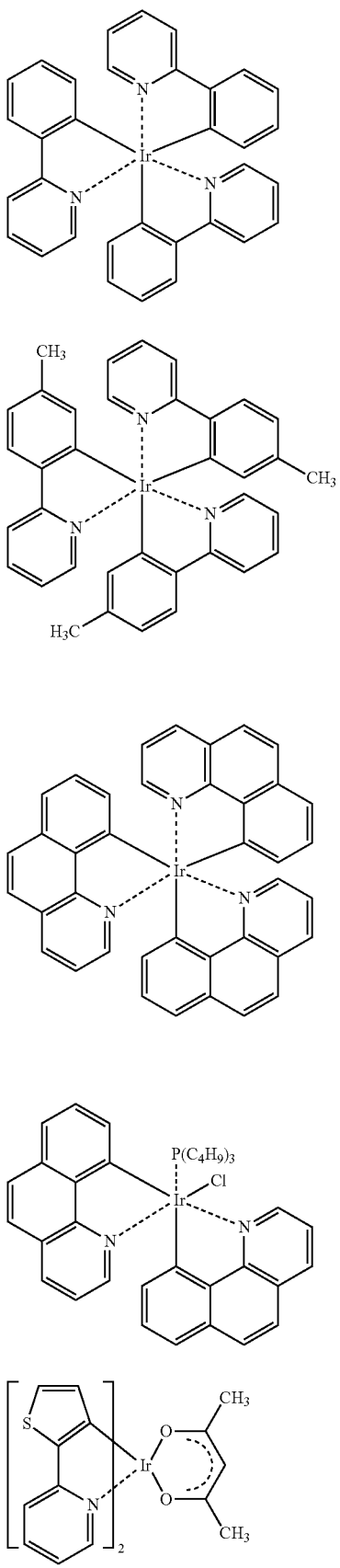
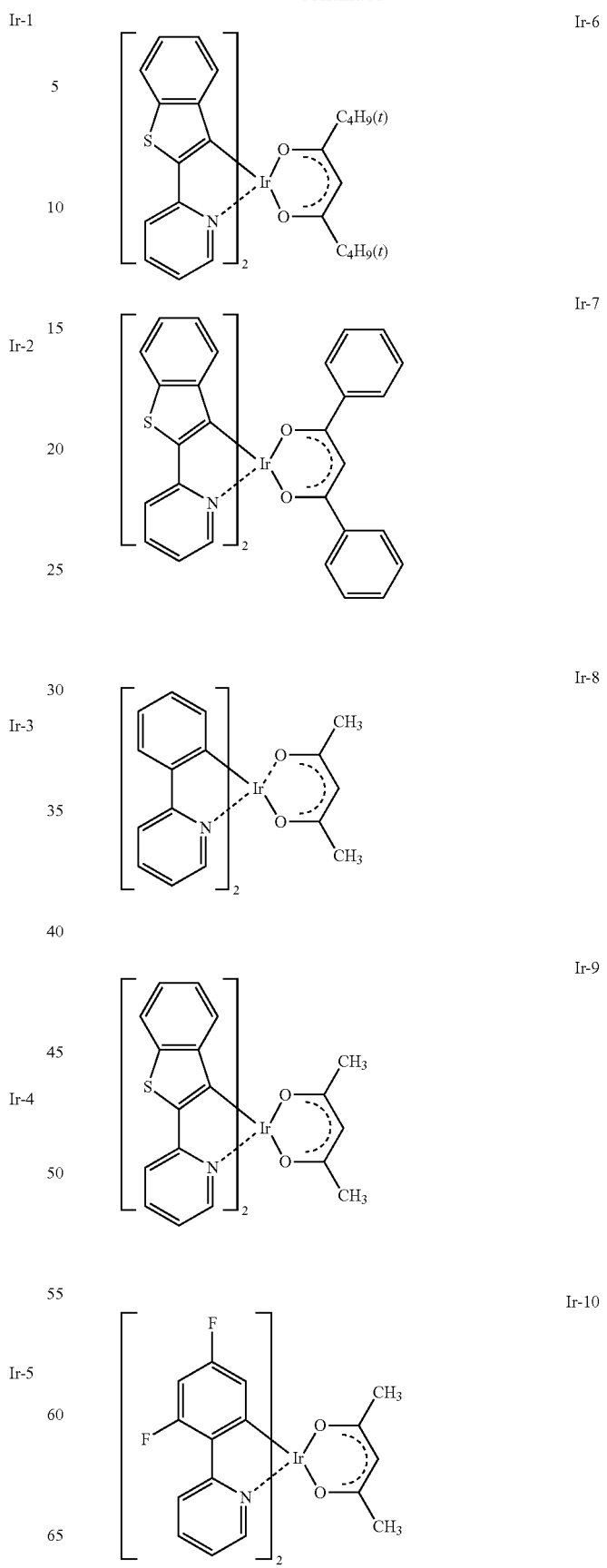

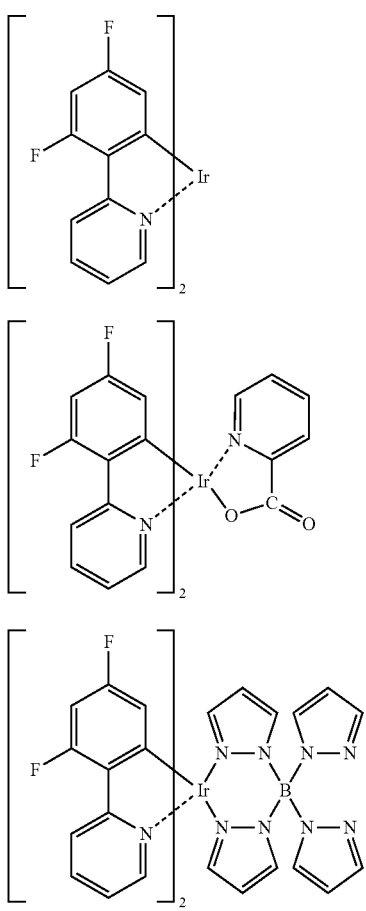

(Emission Host)

An emission host (also referred to as a host) means the compound of which the mixing ratio (in weight) is largest in the emission layer containing two or more compounds, and other compound is called as a dopant compound (also referred to as a dopant). For example, when an emission layer is constituted from two kinds of compound, namely, Compound A and Compound B, and the mixing ratio is A:B=10: 90, then, Compound A is the dopant compound and Compound B is the host compound. Furthermore, when an emission layer is constituted from three kinds of compounds, namely, Compound A, Compound B, and Compound C, and rhe mixing ratio is A:B:C=5:10:85, then, compound A and a compound B are dopant compounds, and Compound C is the host compound.

The emission host of the present invention is preferably a compound having a shorter wavelength O—O band of phosphorescence than that of the emission dopant used together with the emission host. When the emission dopant exhibits a wavelength of the O—O band of 480 nm or less, the emission host preferably exhibits a wavelength of the O—O band of phosphorescence of 450 nm or less.

The structure of the emission host of the present invention is not specifically limited, however, preferable is a compound having a structure of, for example, a carbazole derivative, a triarylamine derivative, an aromatic borane derivative, a nitrogen-containing heterocyclic compound, a thiophene derivative, a furan derivative, or an oligoarylene compound, as well as exhibiting a wavelength of the O—O band of phosphorescence of 450 nm or less. The emission host of the present invention may be a low molecular weight compound, a polymer compound having a repeat unit, or a low molecular weight compound having a polymerizable group like a vinyl group or an epoxy group (vapor-deposition-polymerizable emission host).

The emission host is preferably a compound having a hole transport ability, an electronic transport ability and a higher Tg (glass transition temperature), while preventing a shift of emission wavelength toward a long wavelength region.

As specific examples of an emission host, preferable is the compounds described in the following Patent Documents: for example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334709, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-805084 and 2002-308837.

Next, the constitution of a typical organic EL element will be described.

<<Composition Layer of Organic EL Element>>

The constituting layers of the organic EL element of the present invention will be described.

Preferable examples of a specific layer constitution of the organic EL of the present invention will be shown below, however, the present invention is not limited thereto.

(i) Anode/Emission layer/Electron transport layer/Cathode (ii) Anode/Hole transport layer/Emission layer/Electron transport layer/Cathode (iii) Anode/Hole transport layer/Emission layer/Hole blocking layer/Electron transport layer/Cathode (iv) Anode/Hole transport layer/Emission layer/hole blocking layer/Electron transport layer/Cathode buffer layer/Cathode (v) Anode/Anode buffer layer/Hole transport layer/Emission layer/Hole blocking layer/Electron transport layer/Cathode buffer layer/Cathode <<Emission Layer>>

In the present invention, it is preferable that the material of this invention for the organic EL element is used, however, besides those, above known emission host and emission dopant may be used together with those.

It is preferable for enhancing the effects of the invention (rising of luminance and prolongation of light emission life time) that the light emission layer contains a compound represented by Formula I. The compound is preferably used in the light emission layer as a light emission host.

In Formula I, $Z_1$ is a group of atoms for forming an aromatic ring which may have a substituent and $Z_2$ is a group of atoms for forming an aromatic heterocyclic ring or an aromatic hydrocarbon ring each of which may have a substituent, and $Z_3$ is a divalent bonding group or a single bond. $R_{101}$ is a hydrogen atom or a substituent.

Examples of the aromatic heterocyclic ring formed by the group of atoms represented by $Z_1$ or $Z_2$ include a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring, a diazacarbazole ring (a ring formed by further substituting a carbon atom of the hydrocarbon group constituting a carboline ring by a nitrogen atom). The aromatic heterocyclic ring may have a substituent represented by the later-mentioned $R_{101}$.

As the aromatic hydrocarbon ring formed by the group of atoms represented by $Z_2$, a benzene ring, a biphenyl ring, an azulene ring, an anthracene ring, a phenanthrene ring, a pyrene ring, a chrysene ring, a naphthacene ring, a triphenyline ring, o-terphenyl ring, a m-terphenyl ring, a p-terphenyl ring, an acenaphthene ring, a coronene ring, a fluorene ring, a fluoranthene ring, a naphthacene ring, a pentacene ring, a perylene ring, a pentaphene ring, a picene ring, a pyrene ring, a pyranthrene ring and a anthanthrene ring are cited.

These aromatic heterocyclic rings and aromatic hydrocarbon rinds each may have a substituent. The substituents are synonymous with those represented by $Z_{01}$, $Z_{01}$ or $Z_{02}$ in Formula 1.

The substituents represented by $P_{101}$ are also synonymous with those represented by $Z_{01}$, $Z_{01}$ or $Z_{02}$ in Formula 1. Preferably substituents are an alkyl group, a cycloalkyl group, a fluorohydrocarbon group, an aryl group and an aromatic heterocyclic ring.

The divalent bonding group represented by $Z_3$ is synonymous with $L_{01}$ and $L_{02}$ in Formula 1. The simple bonding is a bonding hand directly bonding substituents with together.

In the invention, the ring formed by $Z_1$ is preferably a 6-memebered ring. The light emission efficiency can be raised and the durability can be further prolonged by such the ring. In the invention the ring formed by $Z_2$ is preferably a 6-memebered ring. The light emission efficiency can be raised and the durability can be further prolonged by such the ring. It is preferable that both of the rings represented by $Z_1$ and $Z_2$ are each simultaneously a 6-membered ring. By that, the light emission efficiency can be further raised and the life time can be further prolonged.

Concrete examples of the compound represented by Formula I are listed below, but the invention is not limited to them.

| Compound | Central skeleton | A |
|---|---|---|
| 1 | | |
| 2 | | |
| 3 | | |
| 4 | | |
| 5 | | |

-continued
| Compound | Central skeleton | A |
|---|---|---|
| 6 | 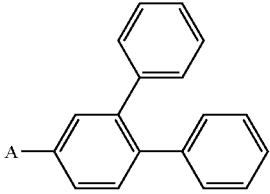 | 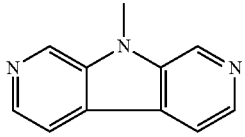 |
| 7 | 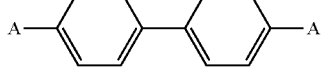 | 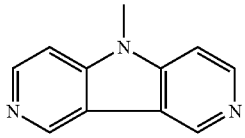 |
| 8 | 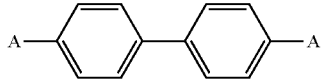 | 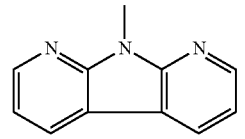 |
| 9 | 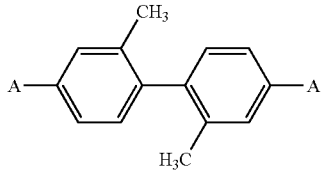 | 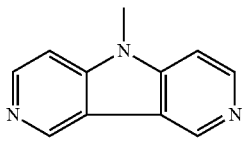 |
| 10 | 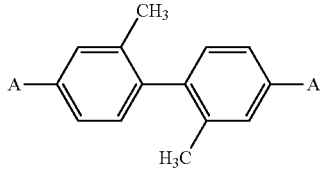 | 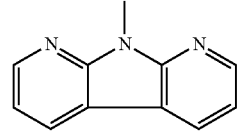 |
| 11 | 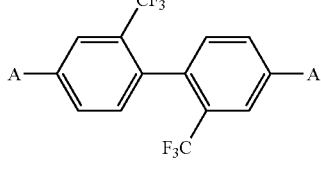 | 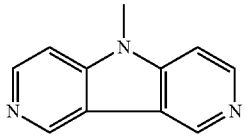 |
| 12 | 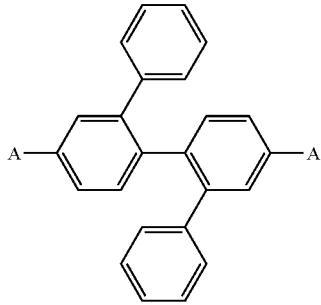 | 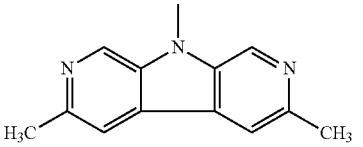 |
| 13 | 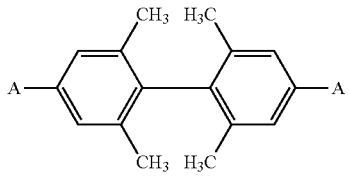 | 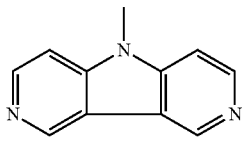 |

-continued
| Compound | Central skeleton | A |
|---|---|---|
| 14 | 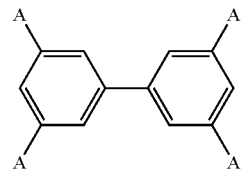 | 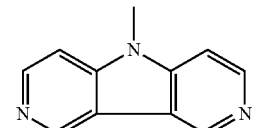 |
| 15 | 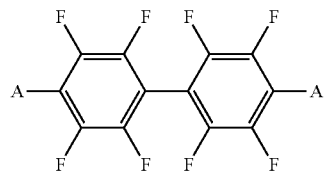 | 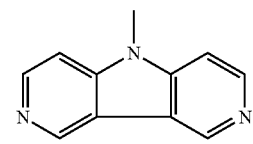 |
| 16 | 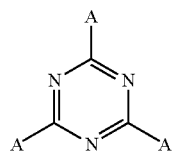 | 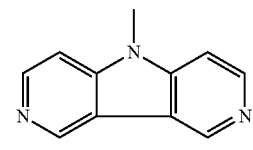 |
| 17 | 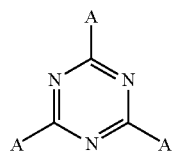 | 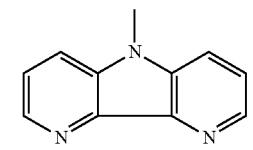 |
| 18 | 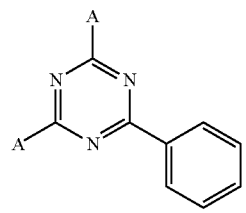 | 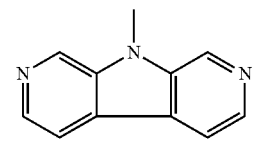 |
| 19 | 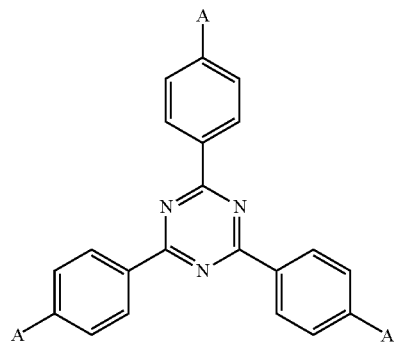 | 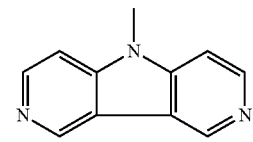 |

-continued
| Compound | Central skeleton | A |
|---|---|---|
| 20 | 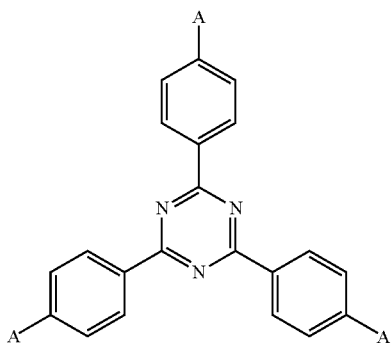 | 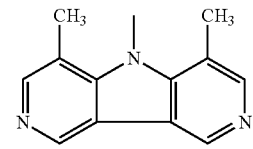 |
| 21 | 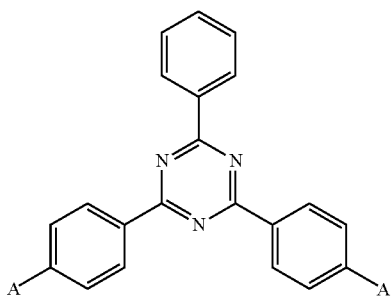 | 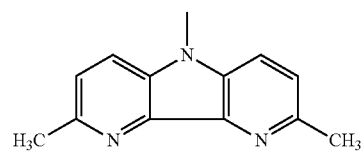 |
| 22 | 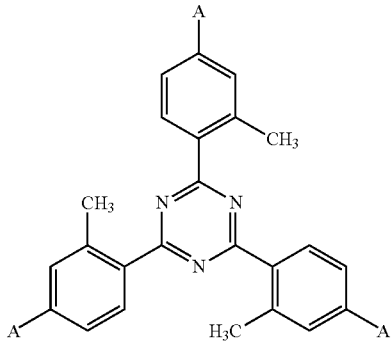 | 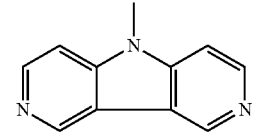 |
| 23 | 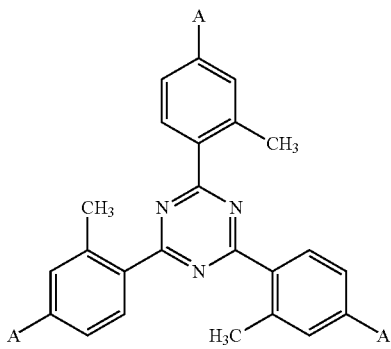 | 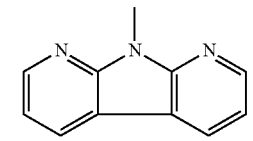 |
| 24 |  | 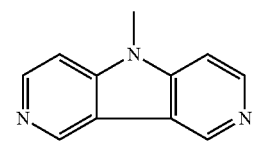 |

-continued
| Compound | Central skeleton | A |
|---|---|---|
| 25 | 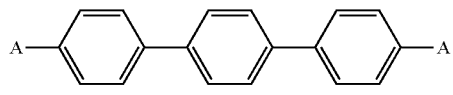 | 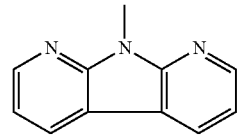 |
| 26 | 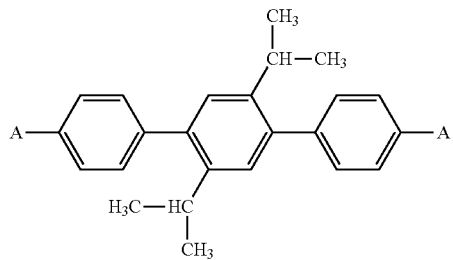 | 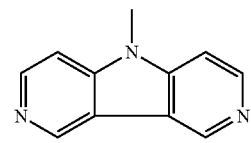 |
| 27 | 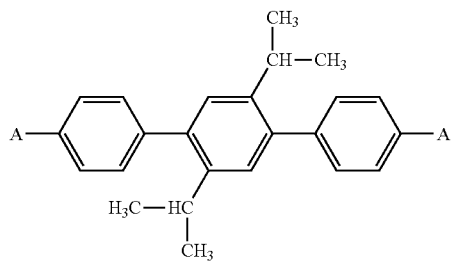 | 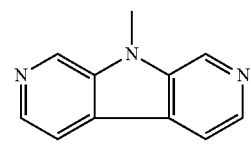 |
| 28 | 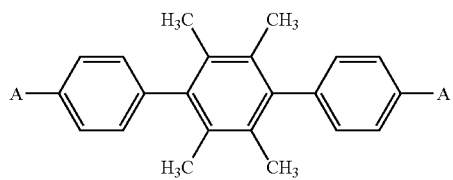 | 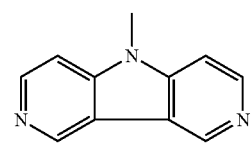 |
| 29 | 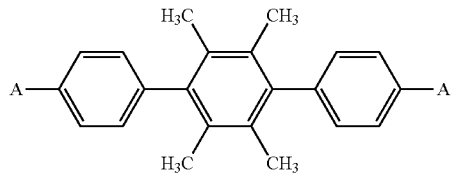 | 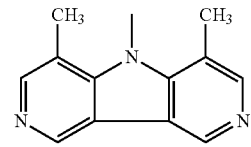 |
| 30 | 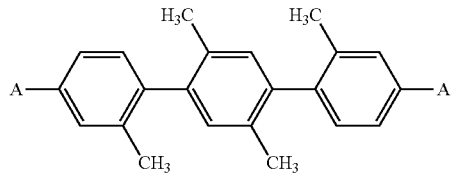 | 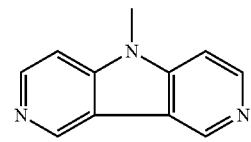 |
| 31 | 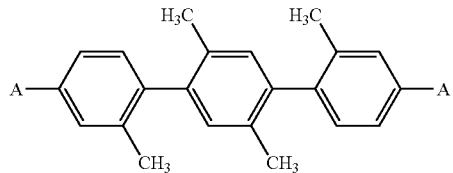 | 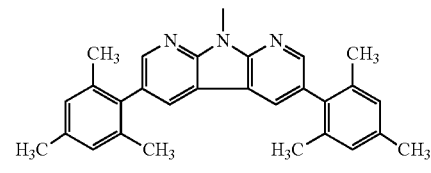 |

US 8,795,853 B2
-continued
| Compound | Central skeleton | A |
|---|---|---|
| 32 | 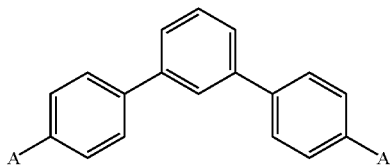 | 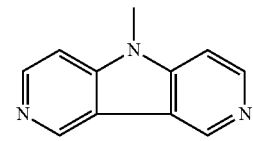 |
| 33 | 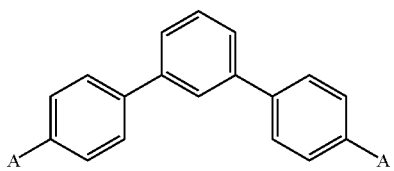 | 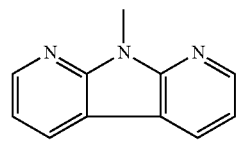 |
| 34 | 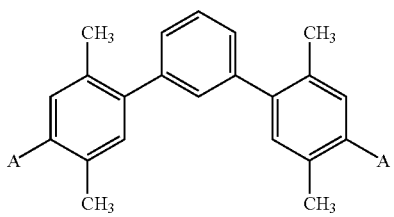 | 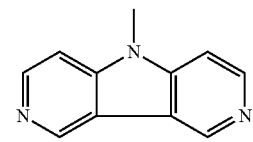 |
| 35 | 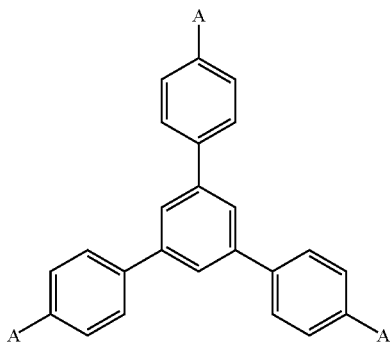 | 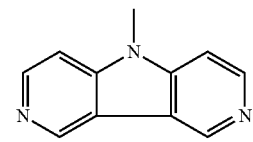 |
| 36 | 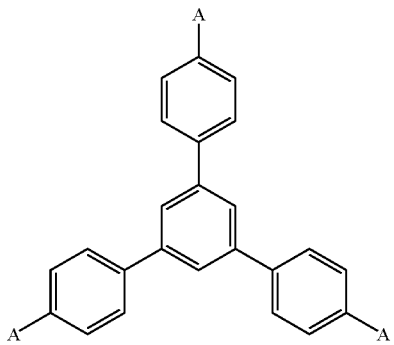 | 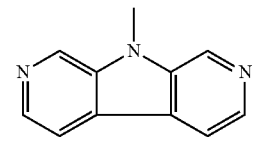 |

-continued
| Compound | Central skeleton | A |
|---|---|---|
| 37 | 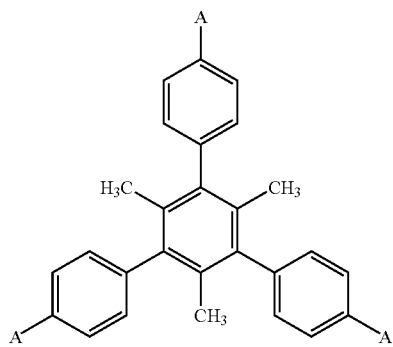 | 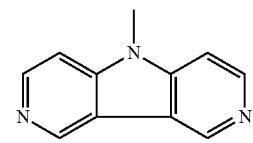 |
| 38 | 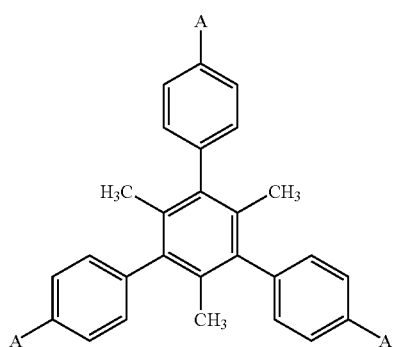 | 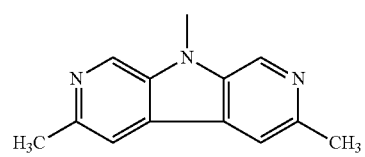 |
| 39 | 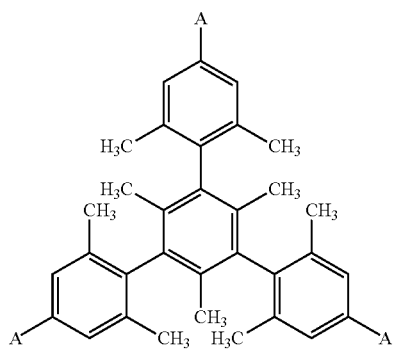 | 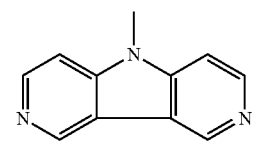 |
| 40 | 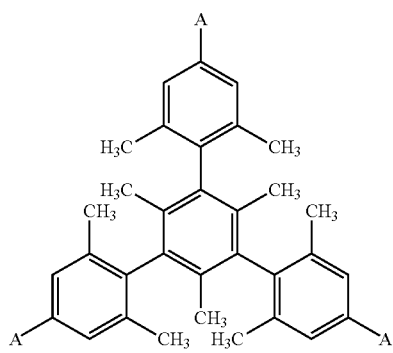 | 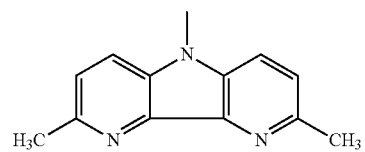 |

-continued
| Compound | Central skeleton | A |
|---|---|---|
| 41 | 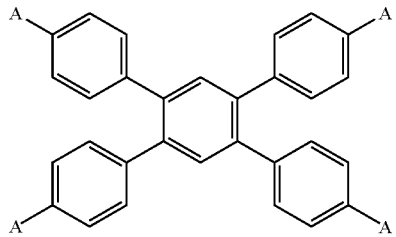 | 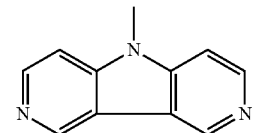 |
| 42 | 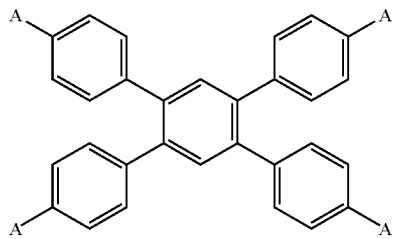 | 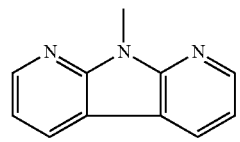 |
| 43 | 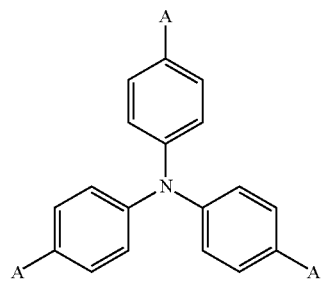 | 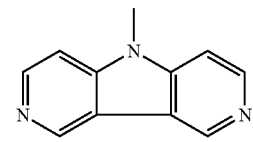 |
| 44 | 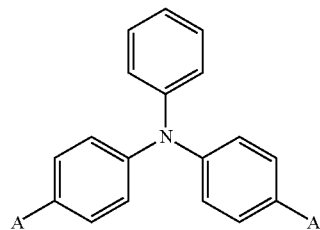 | 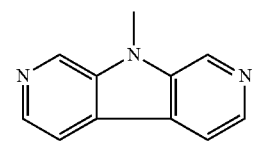 |
| 45 | 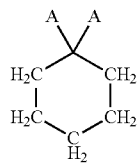 | 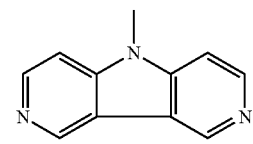 |
| 46 | 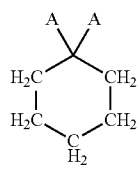 | 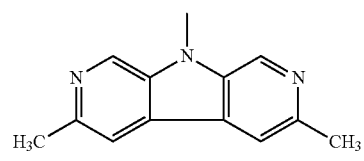 |

-continued

| Compound | Central skeleton | A |
|---|---|---|
| 47 | (bis-phenyl with CH₂ linkers, A substituents) | 5H-pyrrolo[3,2-c:4,5-c']dipyridine, N-methyl |
| 48 | A–C₆H₄–C(CH₃)₂–C₆H₄–A | 5H-pyrrolo[3,2-c:4,5-c']dipyridine, N-methyl |
| 49 | A–C₆H₄–C(CH₃)₂–C₆H₄–A | 9H-pyrrolo[2,3-b:5,4-b']dipyridine, N-methyl |
| 50 | A–C₆H₄–C(CF₃)₂–C₆H₄–A | 5H-pyrrolo[3,2-b:4,5-b']dipyridine, N-methyl |
| 51 | A–C₆H₄–C(CF₃)₂–C₆H₄–A | 5H-pyrrolo[3,2-c:4,5-c']dipyridine, N-methyl |
| 52 | A–C₆H₄–C(CF₃)₂–C₆H₄–A | 9H-pyrrolo[2,3-b:5,4-b']dipyridine, N-methyl |
| 53 | A–C₆H₄–C(CH₃)₂–C₆H₄–C(CH₃)₂–C₆H₄–A | 5H-pyrrolo[3,2-c:4,5-c']dipyridine, N-methyl |
| 54 | A–C₆H₄–C(CH₃)₂–C₆H₄–C(CH₃)₂–C₆H₄–A | 9H-pyrrolo[2,3-b:5,4-b']dipyridine, N-methyl |
| 55 | A–C₆H₄–C(CH₃)₂–C₆H₄–C(CH₃)₂–C₆H₄–A | 5H-pyrrolo[3,2-c:4,5-c']dipyridine, N-methyl |

-continued
| Compound | Central skeleton | A |
|---|---|---|
| 56 | 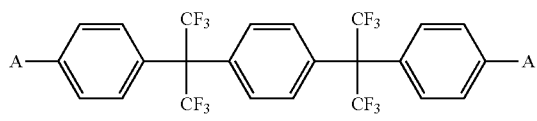 | 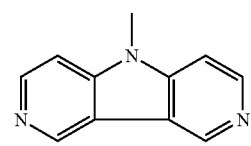 |
| 57 | 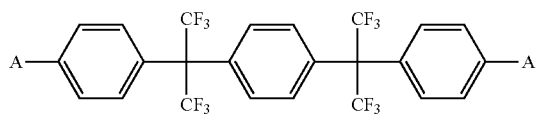 | 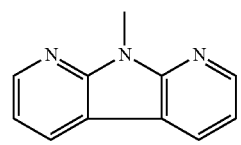 |
| 58 | 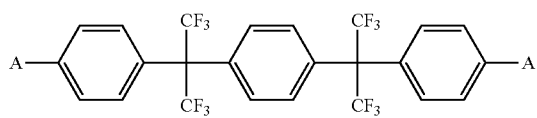 | 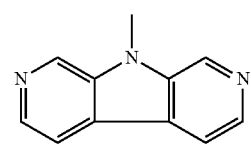 |
| 59 | 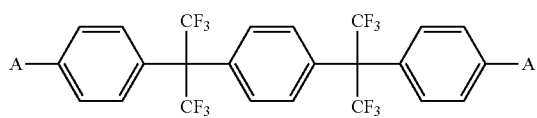 | 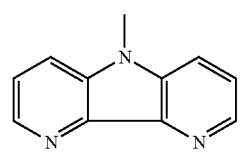 |
| 60 | 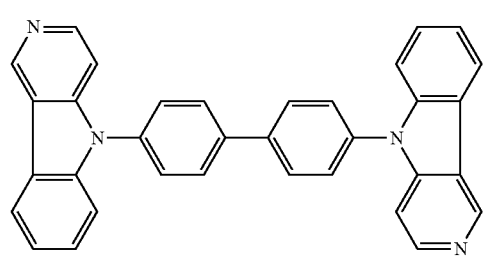 [SMILES: c1ccc2c(c1)c1cnccc1n2-c1ccc(-c2ccc(-n3c4ccccc4c4cnccc43)cc2)cc1] | |
| 61 | 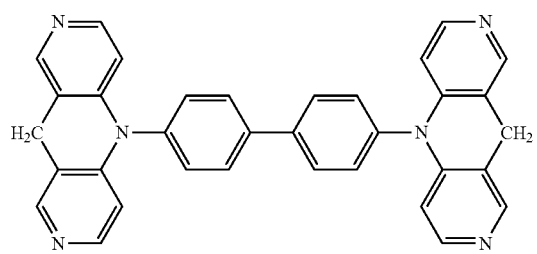 [SMILES: c1cc2c(cn1)Cc1cnccc1N2c1ccc(-c2ccc(N3c4ccncc4Cc4cnccc43)cc2)cc1] | |
| 62 | 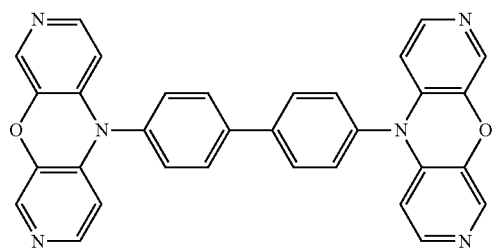 [SMILES: c1cc2c(cn1)Oc1cnccc1N2c1ccc(-c2ccc(N3c4ccncc4Oc4cnccc43)cc2)cc1] | |

-continued
| Compound | Central skeleton | A |
|---|---|---|
| 63 | 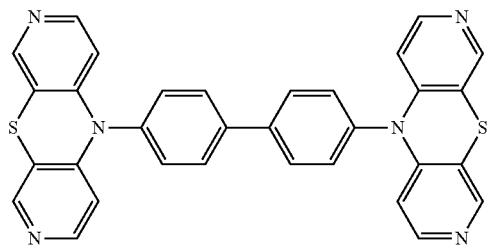 [SMILES: c1cc2c(cn1)Sc1cnccc1N2c1ccc(-c2ccc(N3c4ccncc4Sc4cnccc43)cc2)cc1] | |
| 64 | 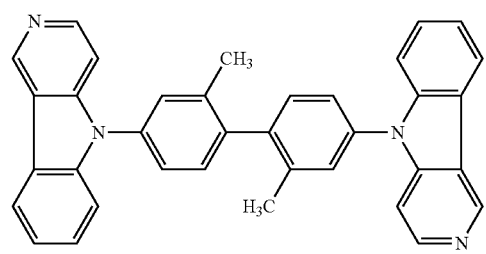 [SMILES: Cc1cc(-n2c3ccccc3c3cnccc32)ccc1-c1ccc(-n2c3ccccc3c3cnccc32)cc1C] | |
| 65 | 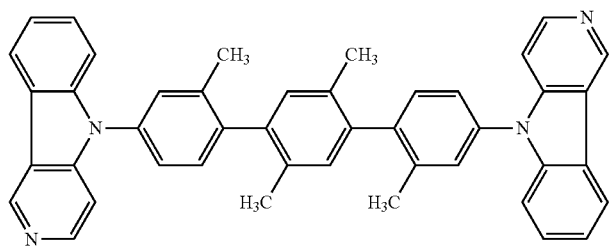 [SMILES: Cc1cc(-n2c3ccccc3c3cnccc32)ccc1-c1cc(C)c(-c2ccc(-n3c4ccccc4c4cnccc43)cc2C)cc1C] | |
| 66 | 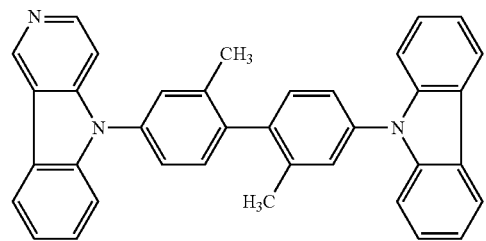 [SMILES: Cc1cc(-n2c3ccccc3c3ccccc32)ccc1-c1ccc(-n2c3ccccc3c3cnccc32)cc1C] | |
| 67 | 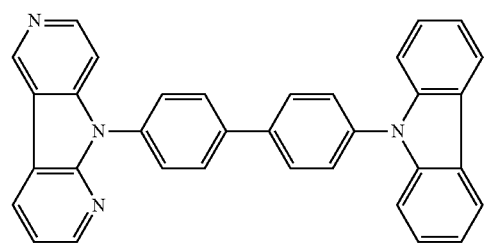 [SMILES: c1ccc2c(c1)c1ccccc1n2-c1ccc(-c2ccc(-n3c4ccncc4c4cccnc43)cc2)cc1] | |

-continued
| Compound | Central skeleton | A |
|---|---|---|
| 68 | 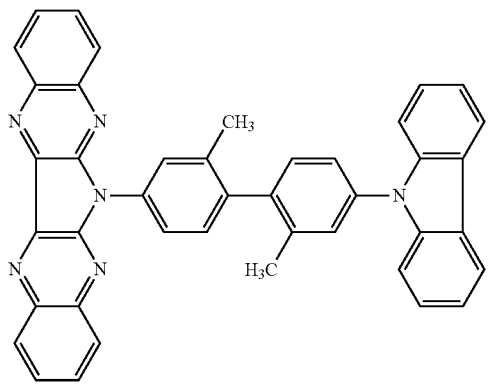 [SMILES: Cc1cc(-n2c3ccccc3c3ccccc32)ccc1-c1ccc(-n2c3nc4ccccc4nc3c3nc4ccccc4nc32)cc1C] | |
| 69 | 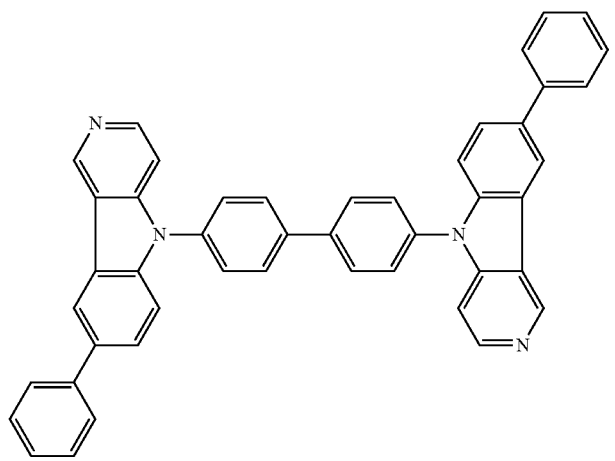 [SMILES: c1ccc(-c2ccc3c(c2)c2cnccc2n3-c2ccc(-c3ccc(-n4c5ccncc5c5cc(-c6ccccc6)ccc54)cc3)cc2)cc1] | |
| 70 | 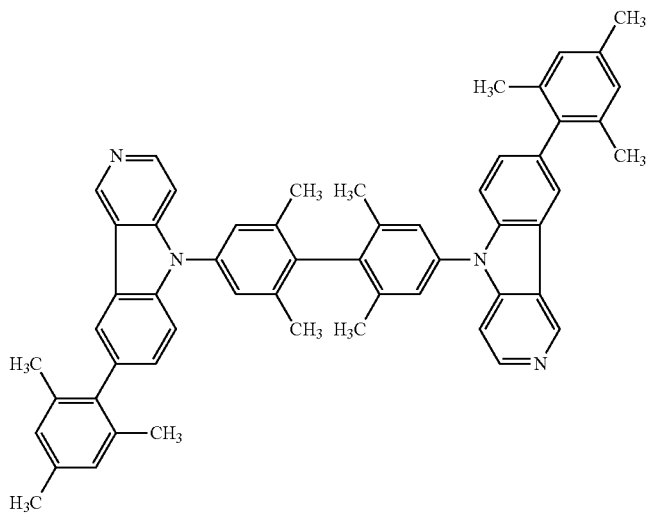 [SMILES: Cc1cc(C)c(-c2ccc3c(c2)c2cnccc2n3-c2cc(C)c(-c3c(C)cc(-n4c5ccncc5c5cc(-c6c(C)cc(C)cc6C)ccc54)cc3C)c(C)c2)c(C)c1] | |

-continued
| Compound | Central skeleton | A |
|---|---|---|
| 71 | 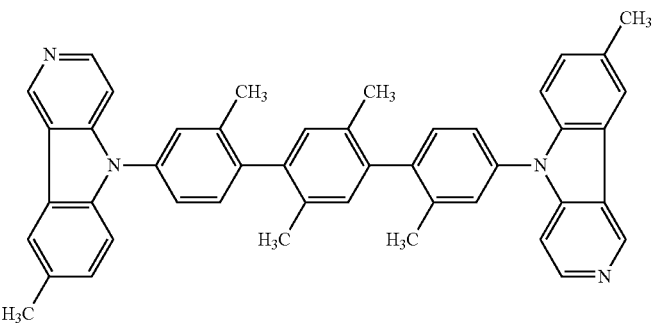 [SMILES: Cc1ccc2c(c1)c1cnccc1n2-c1ccc(-c2cc(C)c(-c3ccc(-n4c5ccncc5c5cc(C)ccc54)cc3C)cc2C)c(C)c1] | |
| 72 | 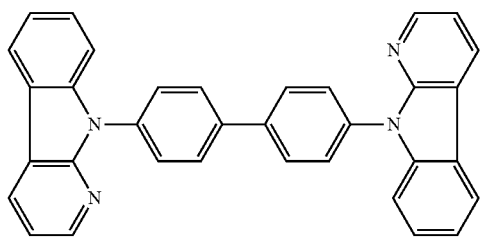 [SMILES: c1ccc2c(c1)c1cccnc1n2-c1ccc(-c2ccc(-n3c4ccccc4c4cccnc43)cc2)cc1] | |
| 73 | 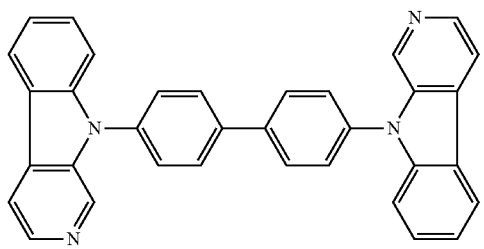 [SMILES: c1ccc2c(c1)c1ccncc1n2-c1ccc(-c2ccc(-n3c4ccccc4c4ccncc43)cc2)cc1] | |
| 74 | 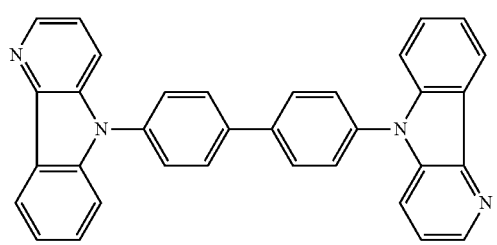 [SMILES: c1ccc2c(c1)c1ncccc1n2-c1ccc(-c2ccc(-n3c4ccccc4c4ncccc43)cc2)cc1] | |
| 75 | 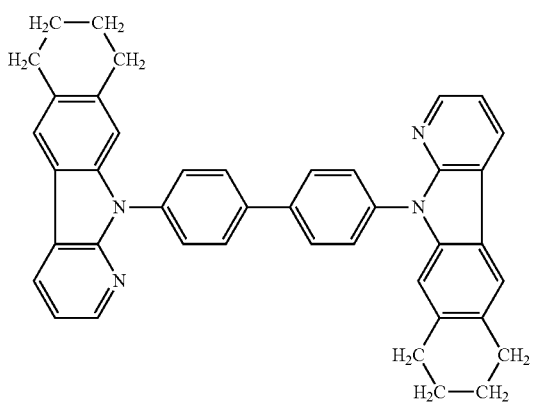 [SMILES: c1cnc2c(c1)c1cc3c(cc1n2-c1ccc(-c2ccc(-n4c5cc6c(cc5c5cccnc54)CCCC6)cc2)cc1)CCCC3] | |

| Compound | Central skeleton | A |
|---|---|---|
| 76 | 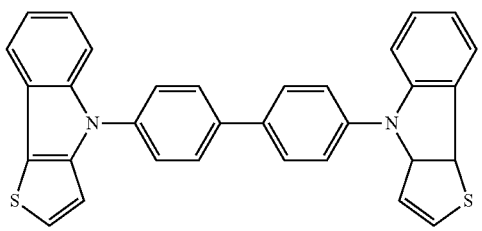 [SMILES: C1=CC2C(S1)c1ccccc1N2c1ccc(-c2ccc(-n3c4ccccc4c4sccc43)cc2)cc1] | |
| 77 | 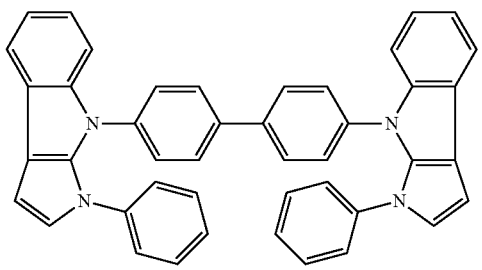 [SMILES: c1ccc(-n2ccc3c4ccccc4n(-c4ccc(-c5ccc(-n6c7ccccc7c7ccn(-c8ccccc8)c76)cc5)cc4)c32)cc1] | |
| 78 | 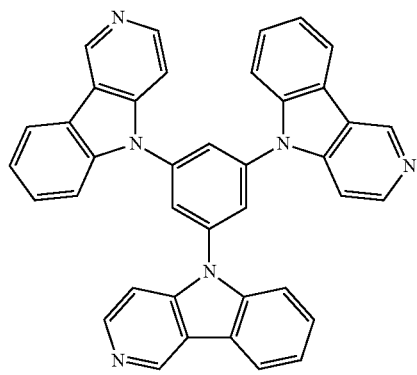 [SMILES: c1ccc2c(c1)c1cnccc1n2-c1cc(-n2c3ccccc3c3cnccc32)cc(-n2c3ccccc3c3cnccc32)c1] | |
| 79 | 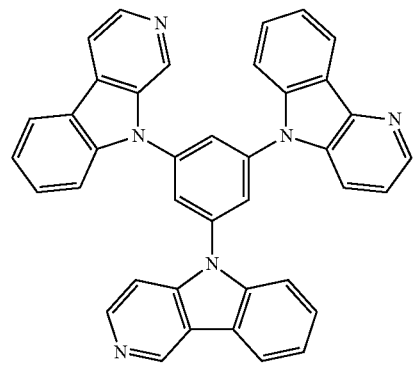 [SMILES: c1ccc2c(c1)c1cnccc1n2-c1cc(-n2c3ccccc3c3ccncc32)cc(-n2c3ccccc3c3ncccc32)c1] | |

| Compound | Central skeleton | A |
|---|---|---|
| 80 | 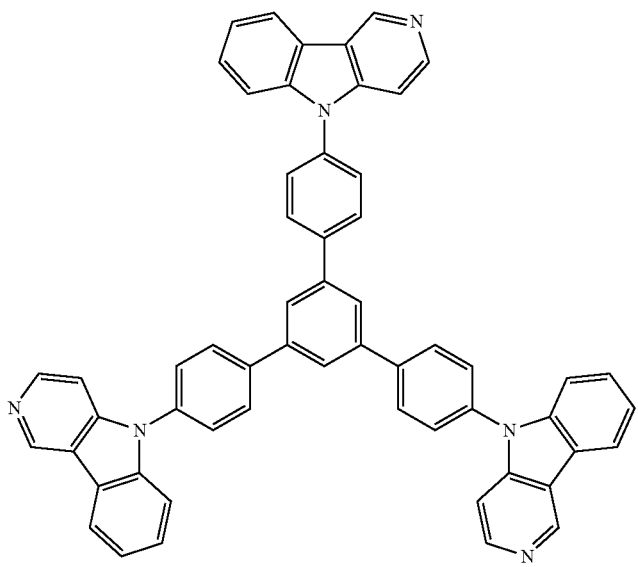 [SMILES: c1ccc2c(c1)c1cnccc1n2-c1ccc(-c2cc(-c3ccc(-n4c5ccccc5c5cnccc54)cc3)cc(-c3ccc(-n4c5ccccc5c5cnccc54)cc3)c2)cc1] | |
| 81 | 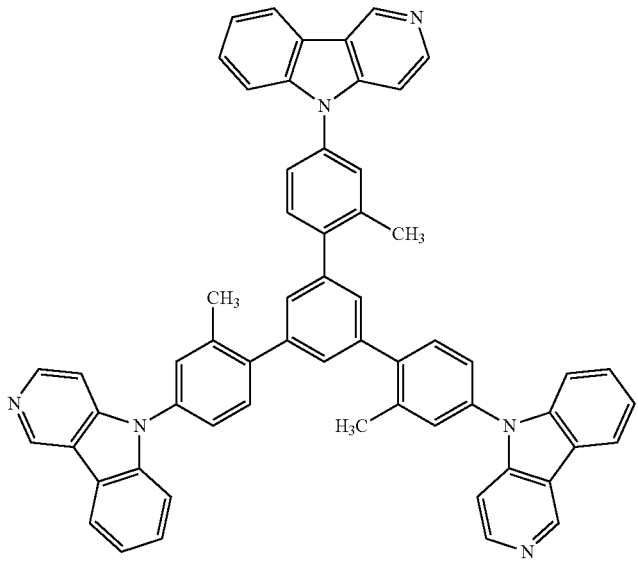 [SMILES: Cc1cc(-n2c3ccccc3c3cnccc32)ccc1-c1cc(-c2ccc(-n3c4ccccc4c4cnccc43)cc2C)cc(-c2ccc(-n3c4ccccc4c4cnccc43)cc2C)c1] | |

| Compound | Central skeleton | A |
|---|---|---|
| 82 | 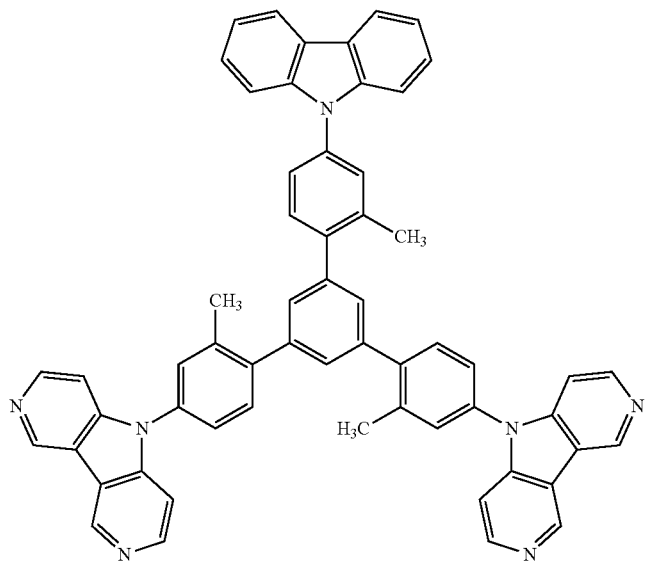 [SMILES: Cc1cc(-n2c3ccccc3c3ccccc32)ccc1-c1cc(-c2ccc(-n3c4ccncc4c4cnccc43)cc2C)cc(-c2ccc(-n3c4ccncc4c4cnccc43)cc2C)c1] | |
| 83 | 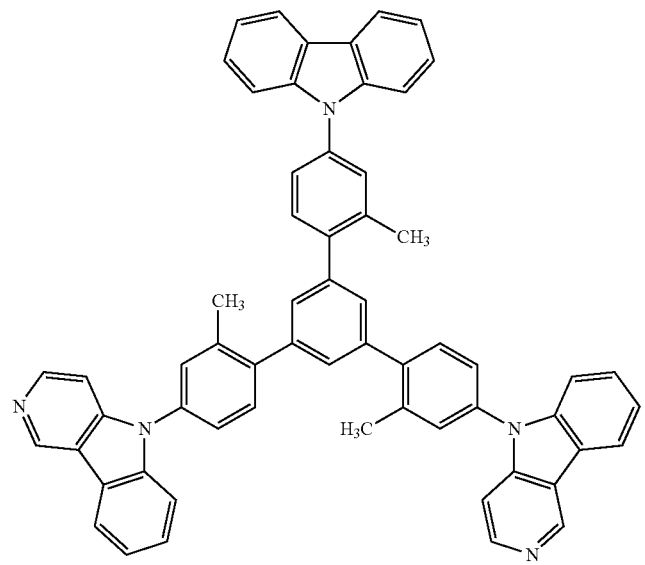 | |
| 84 | 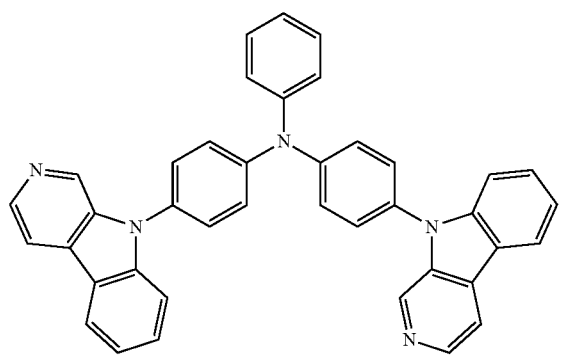 [SMILES: c1ccc(N(c2ccc(-n3c4ccccc4c4ccncc43)cc2)c2ccc(-n3c4ccccc4c4ccncc43)cc2)cc1] | |

-continued

| Compound | Central skeleton | A |
|---|---|---|
| 85 | | |
| 86 | | |
| 87 | | |

-continued

| Compound | Central skeleton | A |
|---|---|---|
| 88 | | |
| 89 | | |
| 90 | | |
| 91 | | |

| Compound | Central skeleton | A |
|---|---|---|
| 92 | 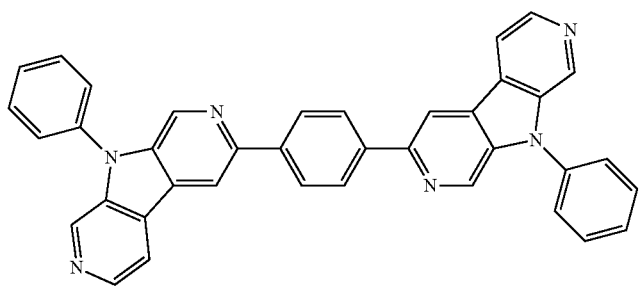 [SMILES: c1ccc(-n2c3cnccc3c3cc(-c4ccc(-c5cc6c7ccncc7n(-c7ccccc7)c6cn5)cc4)ncc32)cc1] | |
| 93 | 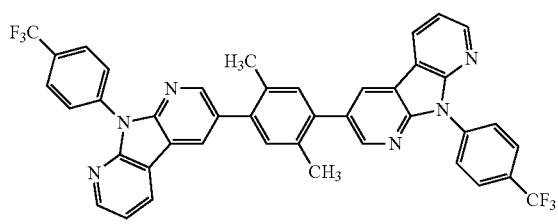 [SMILES: Cc1cc(-c2cnc3c(c2)c2cccnc2n3-c2ccc(C(F)(F)F)cc2)c(C)cc1-c1cnc2c(c1)c1cccnc1n2-c1ccc(C(F)(F)F)cc1] | |
| 94 | 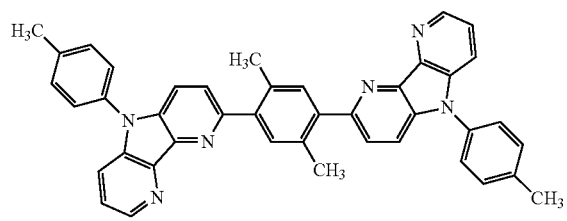 | |
| 95 | 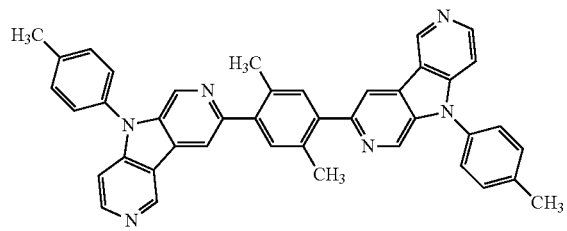 | |
| 96 | 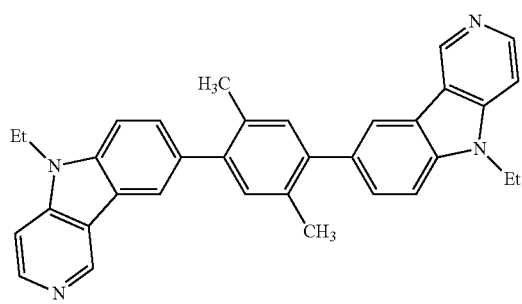 [SMILES: CCn1c2ccncc2c2cc(-c3cc(C)c(-c4ccc5c(c4)c4cnccc4n5CC)cc3C)ccc21] | |

| Compound | Central skeleton | A |
|---|---|---|
| 97 | 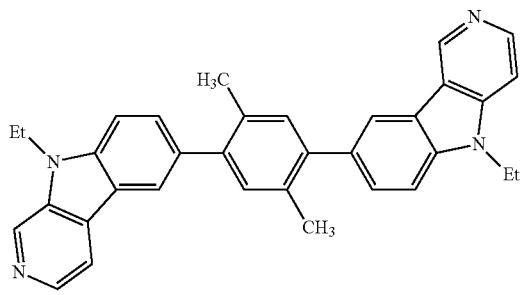 [SMILES: CCn1c2ccncc2c2cc(-c3cc(C)c(-c4ccc5c(c4)c4ccncc4n5CC)cc3C)ccc21] | |
| 98 | 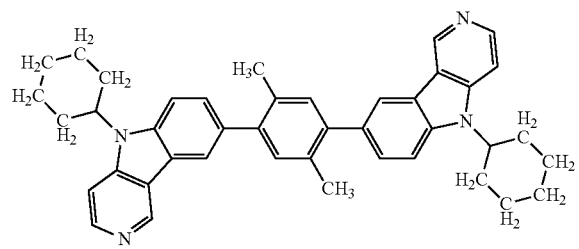 [SMILES: Cc1cc(-c2ccc3c(c2)c2cnccc2n3C2CCCCC2)c(C)cc1-c1ccc2c(c1)c1cnccc1n2C1CCCCC1] | |
| 99 | 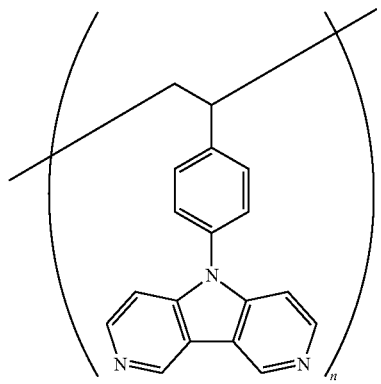 | |
| 100 | 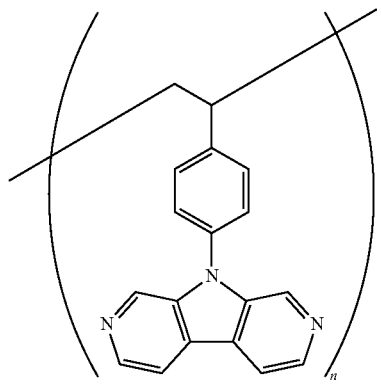 | |

-continued

| Compound | Central skeleton | A |
|---|---|---|
| 101 | | |
| 102 | | |
| 103 | | |
| 104 | | |
| 105 | | |

-continued

| Compound | Central skeleton | A |
|---|---|---|
| 106 | | |
| 107 | | |
| 108 | | |
| 109 | | |
| 110 | | |
| 111 | | |
| 112 | | |

-continued

| Compound | Central skeleton | A |
|---|---|---|
| 113 | | |
| 114 | | |
| 115 | | |
| 116 | | |
| 117 | | |
| 118 | | |
| 119 | | |
| 120 | | |

| Compound | Central skeleton | A |
|---|---|---|
| 121 | 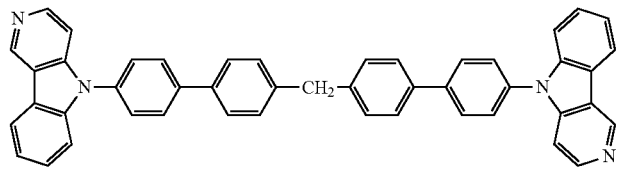 [SMILES: c1ccc2c(c1)c1cnccc1n2-c1ccc(-c2ccc(Cc3ccc(-c4ccc(-n5c6ccccc6c6cnccc65)cc4)cc3)cc2)cc1] | |
| 122 | 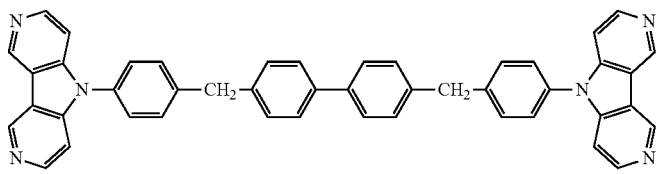 [SMILES: c1cc2c(cn1)c1cnccc1n2-c1ccc(Cc2ccc(-c3ccc(Cc4ccc(-n5c6ccncc6c6cnccc65)cc4)cc3)cc2)cc1] | |
| 123 | 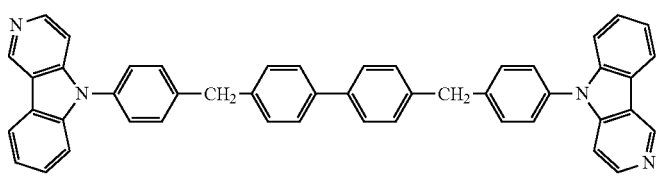 [SMILES: c1ccc2c(c1)c1cnccc1n2-c1ccc(Cc2ccc(-c3ccc(Cc4ccc(-n5c6ccccc6c6cnccc65)cc4)cc3)cc2)cc1] | |
| 124 | 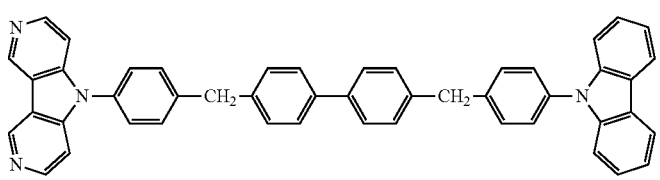 [SMILES: c1ccc2c(c1)c1ccccc1n2-c1ccc(Cc2ccc(-c3ccc(Cc4ccc(-n5c6ccncc6c6cnccc65)cc4)cc3)cc2)cc1] | |
| 125 | 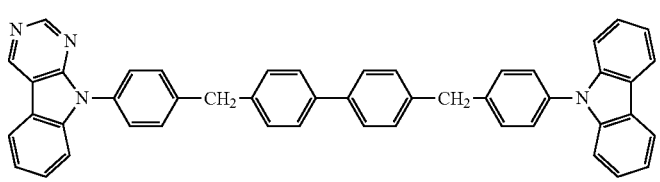 [SMILES: c1ccc2c(c1)c1ccccc1n2-c1ccc(Cc2ccc(-c3ccc(Cc4ccc(-n5c6ccccc6c6cncnc65)cc4)cc3)cc2)cc1] | |
| 126 | 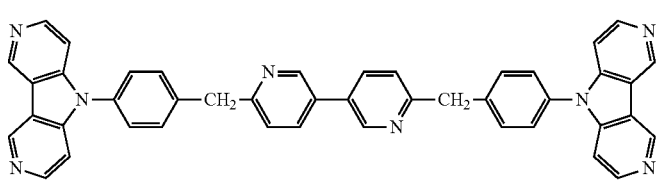 [SMILES: c1cc2c(cn1)c1cnccc1n2-c1ccc(Cc2ccc(-c3ccc(Cc4ccc(-n5c6ccncc6c6cnccc65)cc4)nc3)cn2)cc1] | |
| 127 | 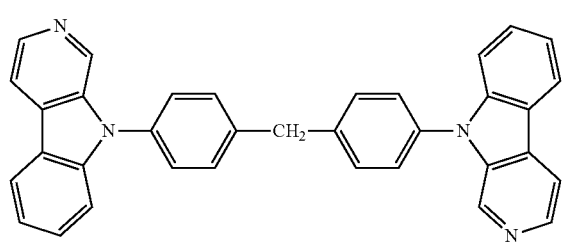 [SMILES: c1ccc2c(c1)c1ccncc1n2-c1ccc(Cc2ccc(-n3c4ccccc4c4ccncc43)cc2)cc1] | |
| 128 | 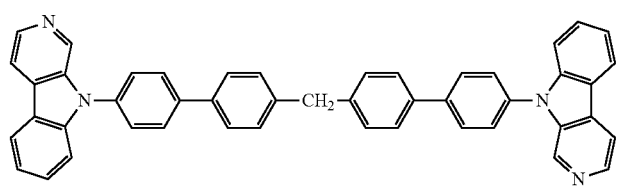 [SMILES: c1ccc2c(c1)c1ccncc1n2-c1ccc(-c2ccc(Cc3ccc(-c4ccc(-n5c6ccccc6c6ccncc65)cc4)cc3)cc2)cc1] | |

| Compound | Central skeleton | A |
|---|---|---|
| 129 | | |
| 130 | | |
| 131 | | |
| 132 | | |
| 133 | | |
| 134 | | |
| 135 | | |
| 136 | | |

-continued
| Compound | Central skeleton | A |
|---|---|---|
| 137 | 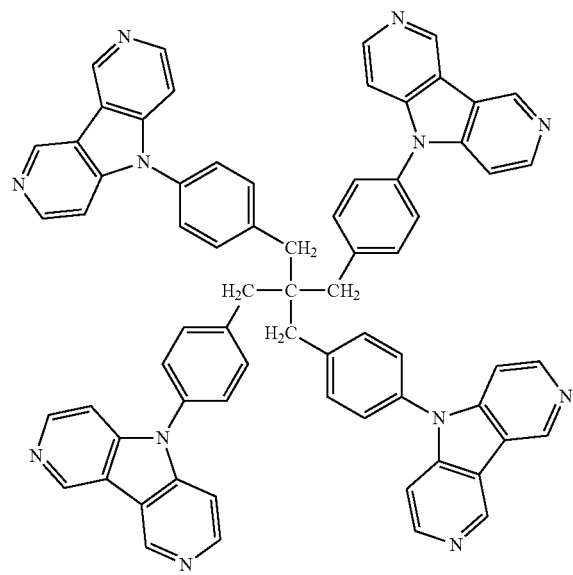 [SMILES: c1cc2c(cn1)c1cnccc1n2-c1ccc(CC(Cc2ccc(-n3c4ccncc4c4cnccc43)cc2)(Cc2ccc(-n3c4ccncc4c4cnccc43)cc2)Cc2ccc(-n3c4ccncc4c4cnccc43)cc2)cc1] | |
| 138 | 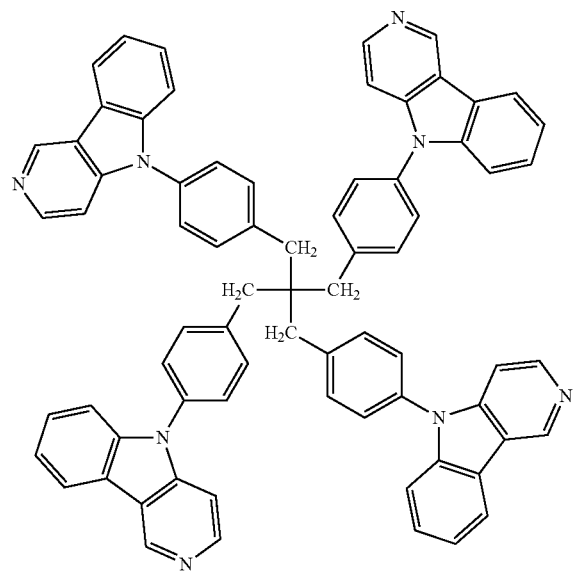 [SMILES: c1ccc2c(c1)c1cnccc1n2-c1ccc(CC(Cc2ccc(-n3c4ccccc4c4cnccc43)cc2)(Cc2ccc(-n3c4ccccc4c4cnccc43)cc2)Cc2ccc(-n3c4ccccc4c4cnccc43)cc2)cc1] | |

-continued
| Compound | Central skeleton | A |
|---|---|---|
| 139 | 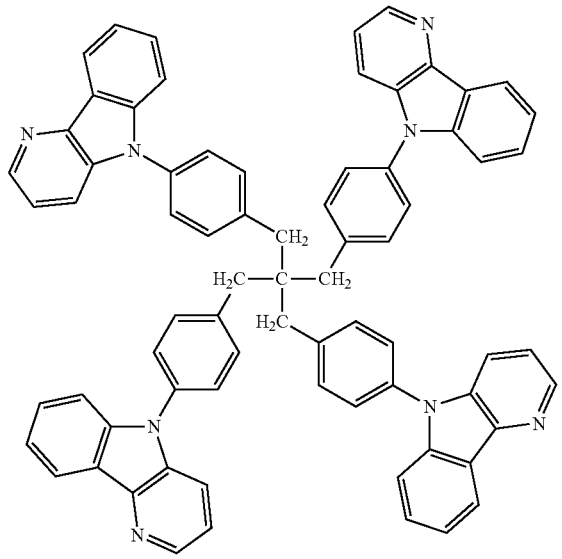 [SMILES: c1ccc2c(c1)c1ncccc1n2-c1ccc(CC(Cc2ccc(-n3c4ccccc4c4ncccc43)cc2)(Cc2ccc(-n3c4ccccc4c4ncccc43)cc2)Cc2ccc(-n3c4ccccc4c4ncccc43)cc2)cc1] | |
| 140 | 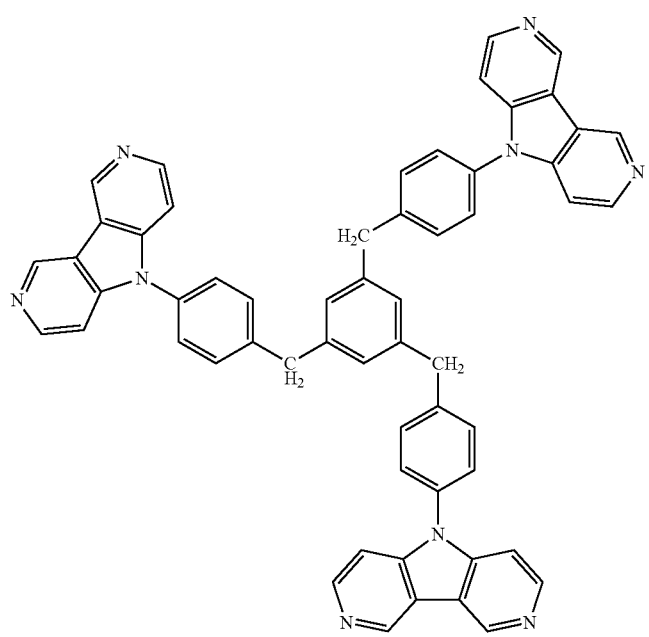 [SMILES: c1cc2c(cn1)c1cnccc1n2-c1ccc(Cc2cc(Cc3ccc(-n4c5ccncc5c5cnccc54)cc3)cc(Cc3ccc(-n4c5ccncc5c5cnccc54)cc3)c2)cc1] | |

-continued
| Compound | Central skeleton | A |
|---|---|---|
| 141 | 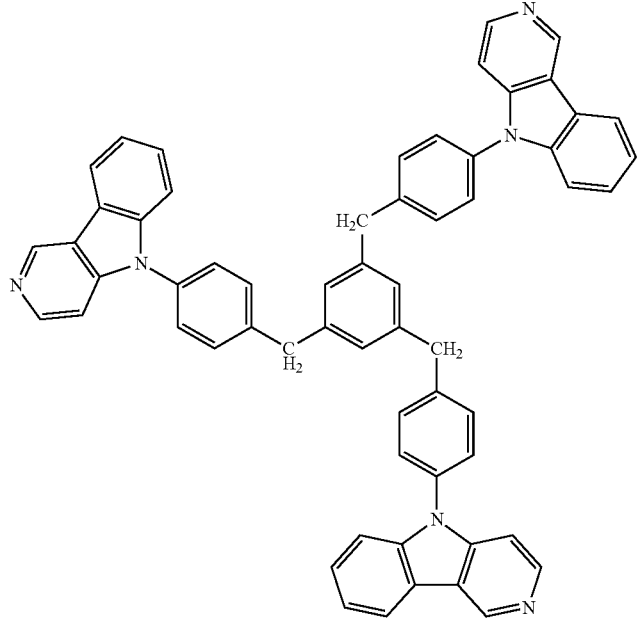 [SMILES: c1ccc2c(c1)c1cnccc1n2-c1ccc(Cc2cc(Cc3ccc(-n4c5ccccc5c5cnccc54)cc3)cc(Cc3ccc(-n4c5ccccc5c5cnccc54)cc3)c2)cc1] | |
| 142 | 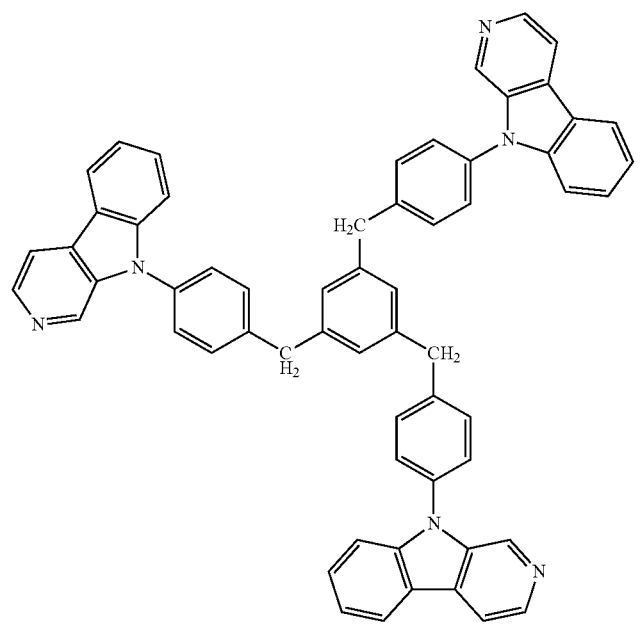 [SMILES: c1ccc2c(c1)c1ccncc1n2-c1ccc(Cc2cc(Cc3ccc(-n4c5ccccc5c5ccncc54)cc3)cc(Cc3ccc(-n4c5ccccc5c5ccncc54)cc3)c2)cc1] | |
| 143 | 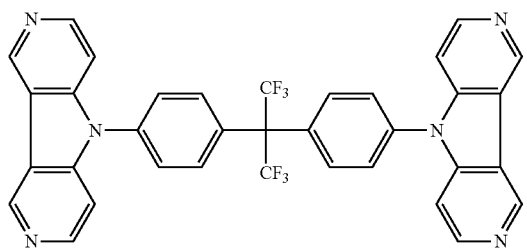 [SMILES: FC(F)(F)C(c1ccc(-n2c3ccncc3c3cnccc32)cc1)(c1ccc(-n2c3ccncc3c3cnccc32)cc1)C(F)(F)F] | |

-continued
| Compound | Central skeleton | A |
|---|---|---|
| 144 | 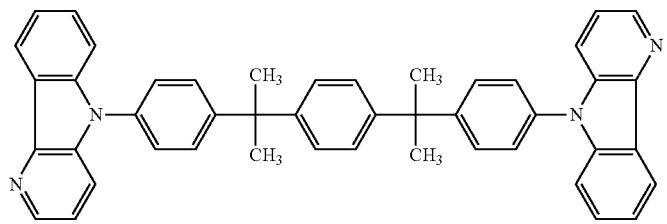 [SMILES: CC(C)(c1ccc(-n2c3ccccc3c3ncccc32)cc1)c1ccc(C(C)(C)c2ccc(-n3c4ccccc4c4ncccc43)cc2)cc1] | |
| 145 | 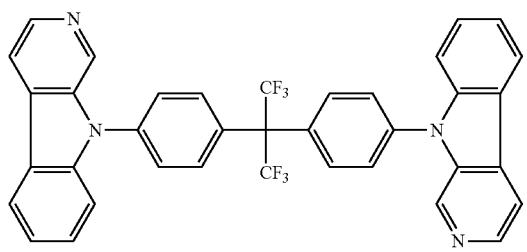 [SMILES: FC(F)(F)C(c1ccc(-n2c3ccccc3c3ccncc32)cc1)(c1ccc(-n2c3ccccc3c3ccncc32)cc1)C(F)(F)F] | |
| 146 | 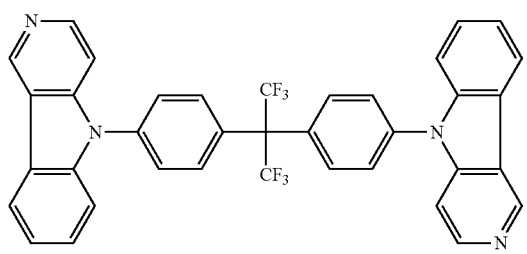 [SMILES: FC(F)(F)C(c1ccc(-n2c3ccccc3c3cnccc32)cc1)(c1ccc(-n2c3ccccc3c3cnccc32)cc1)C(F)(F)F] | |
| 147 | 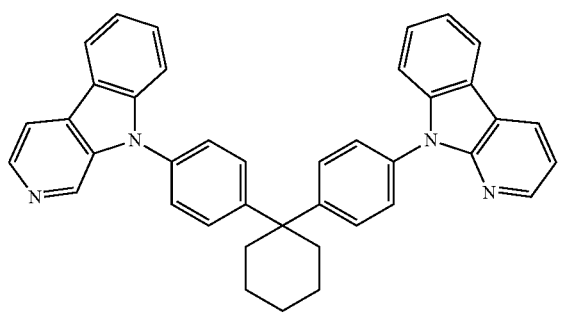 [SMILES: c1ccc2c(c1)c1ccncc1n2-c1ccc(C2(c3ccc(-n4c5ccccc5c5cccnc54)cc3)CCCCC2)cc1] | |
| 148 | 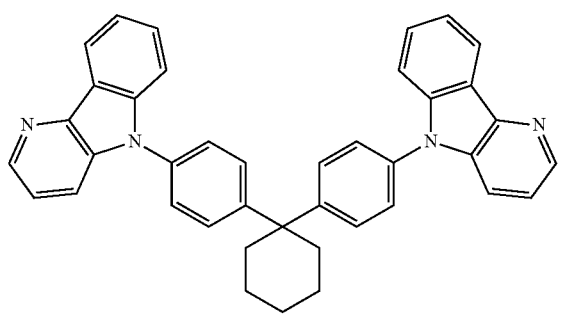 [SMILES: c1ccc2c(c1)c1ncccc1n2-c1ccc(C2(c3ccc(-n4c5ccccc5c5ncccc54)cc3)CCCCC2)cc1] | |

-continued
| Compound | Central skeleton | A |
|---|---|---|
| 149 | 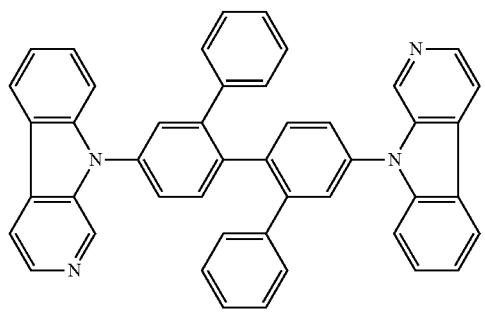 [SMILES: c1ccc(-c2cc(-n3c4ccccc4c4ccncc43)ccc2-c2ccc(-n3c4ccccc4c4ccncc43)cc2-c2ccccc2)cc1] | |
| 150 | 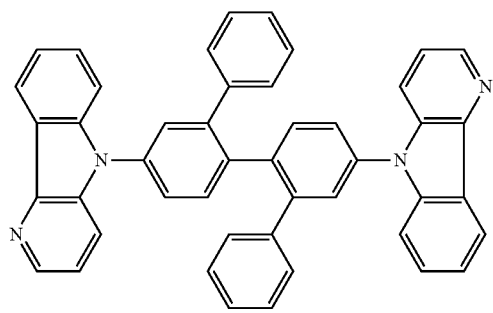 [SMILES: c1ccc(-c2cc(-n3c4ccccc4c4ncccc43)ccc2-c2ccc(-n3c4ccccc4c4ncccc43)cc2-c2ccccc2)cc1] | |
| 151 | 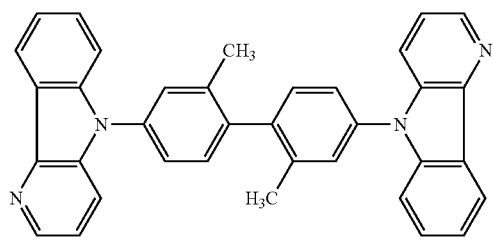 [SMILES: Cc1cc(-n2c3ccccc3c3ncccc32)ccc1-c1ccc(-n2c3ccccc3c3ncccc32)cc1C] | |
| 152 | 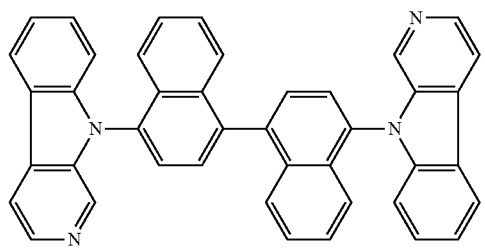 [SMILES: c1ccc2c(-n3c4ccccc4c4ccncc43)ccc(-c3ccc(-n4c5ccccc5c5ccncc54)c4ccccc34)c2c1] | |
| 153 | 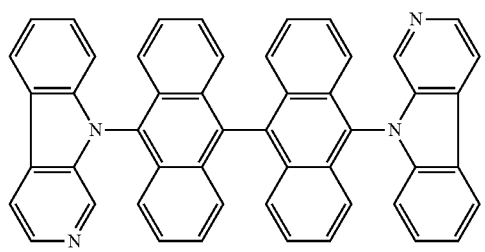 [SMILES: c1ccc2c(-n3c4ccccc4c4ccncc43)c3ccccc3c(-c3c4ccccc4c(-n4c5ccccc5c5ccncc54)c4ccccc34)c2c1] | |

-continued
| Compound | Central skeleton | A |
|---|---|---|
| 154 | 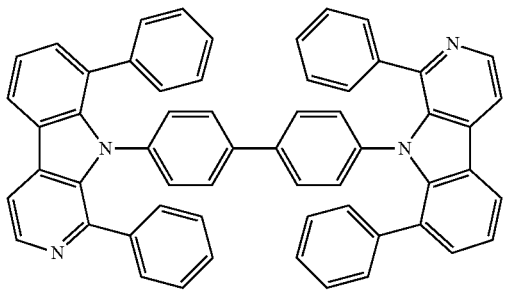 [SMILES: c1ccc(-c2cccc3c4ccnc(-c5ccccc5)c4n(-c4ccc(-c5ccc(-n6c7c(-c8ccccc8)cccc7c7ccnc(-c8ccccc8)c76)cc5)cc4)c23)cc1] | |
| 155 | 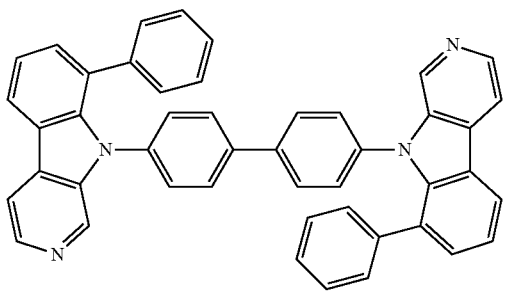 [SMILES: c1ccc(-c2cccc3c4ccncc4n(-c4ccc(-c5ccc(-n6c7cnccc7c7cccc(-c8ccccc8)c76)cc5)cc4)c23)cc1] | |
| 156 | 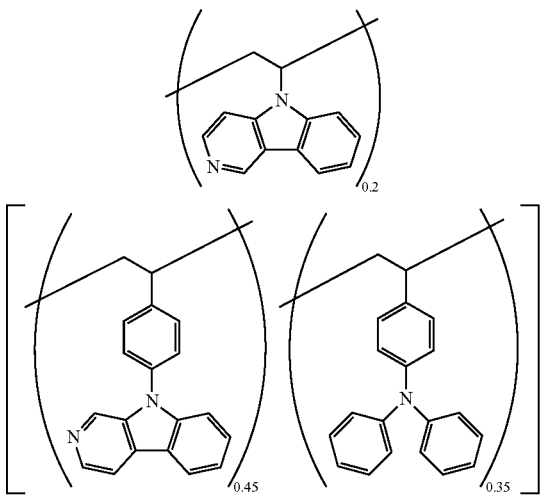 | |
| 157 | 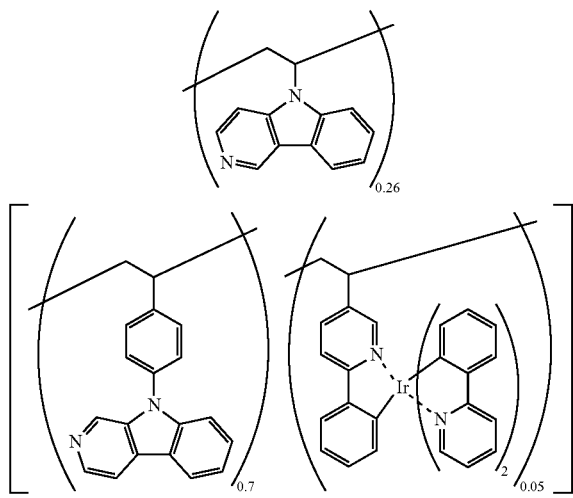 | |

| Compound | Central skeleton | A |
|---|---|---|
| 158 | 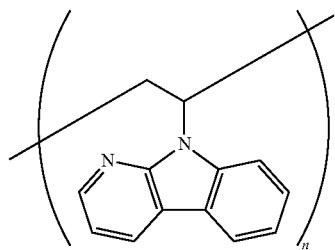 | |
| 159 | 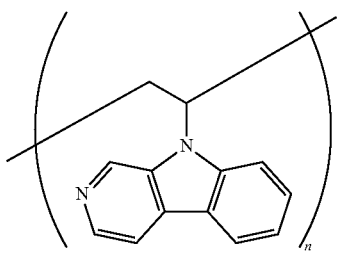 | |
| 160 | 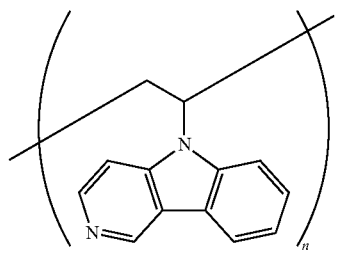 | |
| 161 | 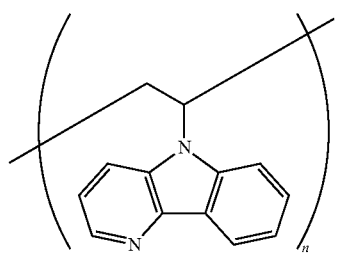 | |
| 162 | 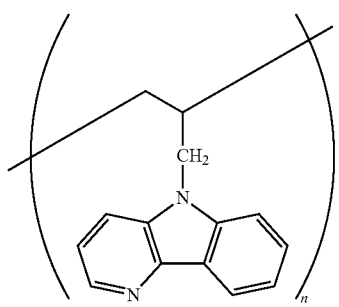 | |

-continued
| Compound | Central skeleton | A |
|---|---|---|
| 163 | 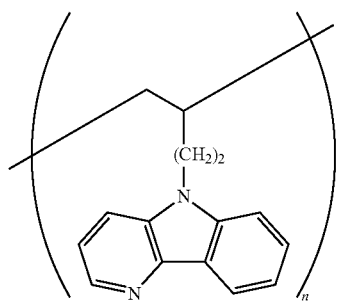 | |
| 164 | 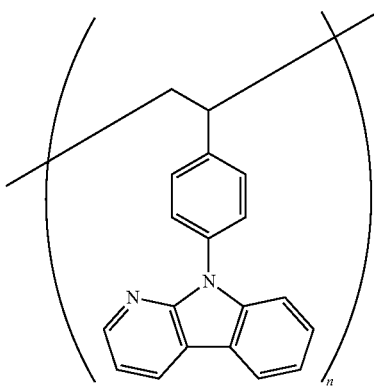 | |
| 165 | 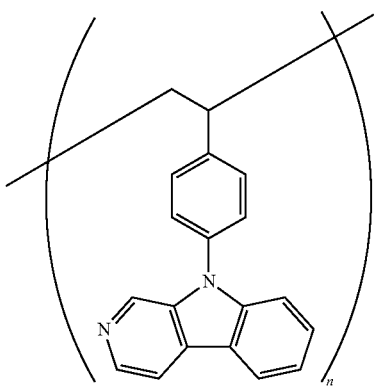 | |
| 166 | 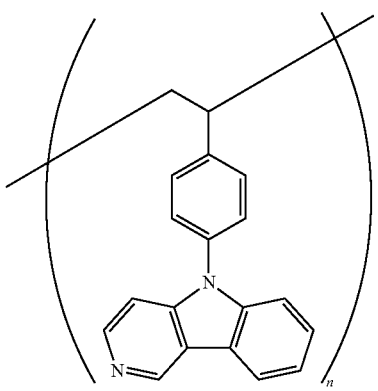 | |

-continued
| Compound | Central skeleton | A |
|---|---|---|
| 167 | 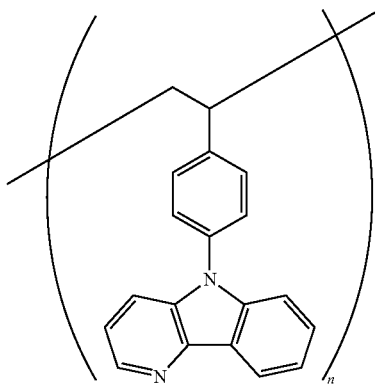 | |
| 168 | 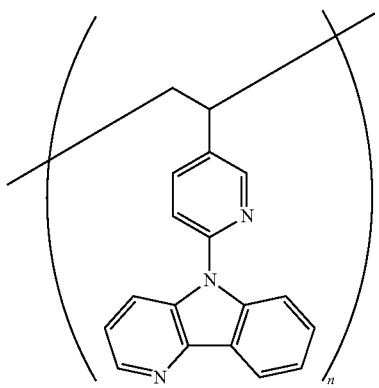 | |
| 169 | 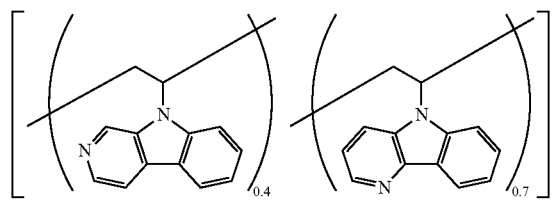 | |
| 170 | 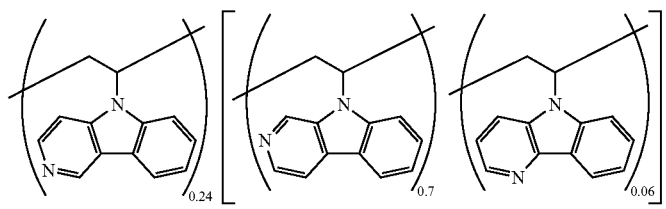 | |
| 171 | 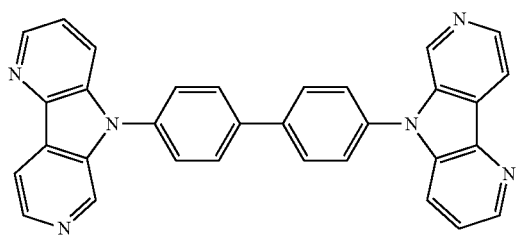 [SMILES: c1cnc2c3ccncc3n(-c3ccc(-c4ccc(-n5c6cnccc6c6ncccc65)cc4)cc3)c2c1] | |

-continued
| Compound | Central skeleton | A |
|---|---|---|
| 172 | 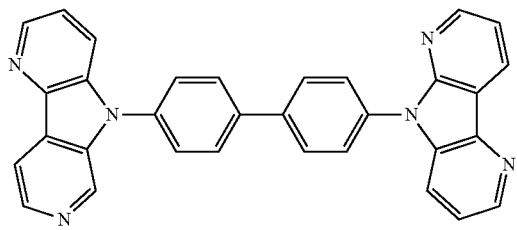 [SMILES: c1cnc2c(c1)c1ncccc1n2-c1ccc(-c2ccc(-n3c4cnccc4c4ncccc43)cc2)cc1] | |
| 173 | 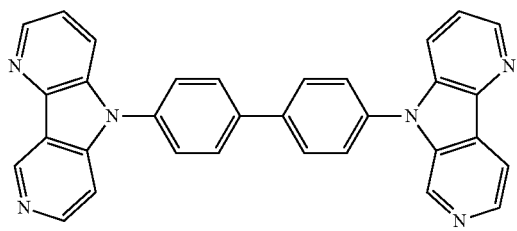 [SMILES: c1cnc2c3cnccc3n(-c3ccc(-c4ccc(-n5c6cnccc6c6ncccc65)cc4)cc3)c2c1] | |
| 174 | 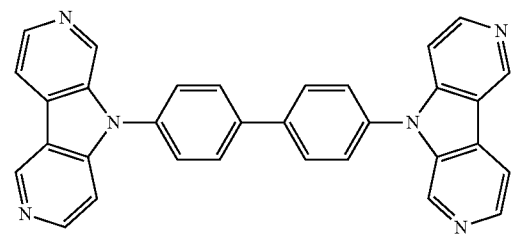 [SMILES: c1cc2c(cn1)c1ccncc1n2-c1ccc(-c2ccc(-n3c4ccncc4c4ccncc43)cc2)cc1] | |
| 175 | 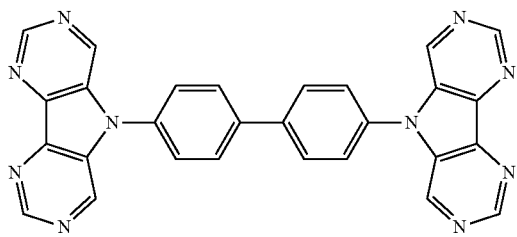 [SMILES: c1ncc2c(n1)c1ncncc1n2-c1ccc(-c2ccc(-n3c4cncnc4c4ncncc43)cc2)cc1] | |
| 176 | 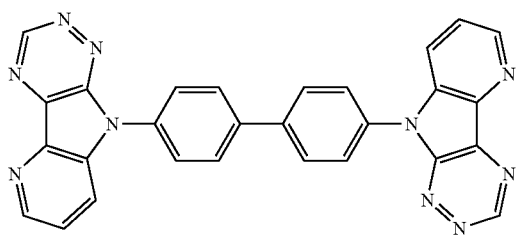 [SMILES: c1cnc2c3ncnnc3n(-c3ccc(-c4ccc(-n5c6cccnc6c6ncnnc65)cc4)cc3)c2c1] | |
| 177 | 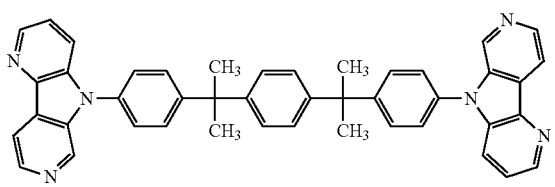 [SMILES: CC(C)(c1ccc(-n2c3cnccc3c3ncccc32)cc1)c1ccc(C(C)(C)c2ccc(-n3c4cnccc4c4ncccc43)cc2)cc1] | |
| 178 | 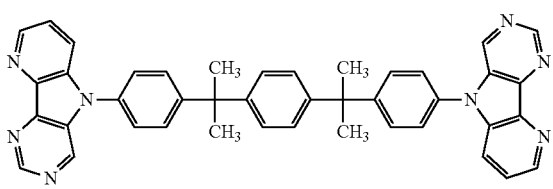 [SMILES: CC(C)(c1ccc(-n2c3cccnc3c3ncncc32)cc1)c1ccc(C(C)(C)c2ccc(-n3c4cccnc4c4ncncc43)cc2)cc1] | |

-continued
| Compound | Central skeleton | A |
|---|---|---|
| 179 | 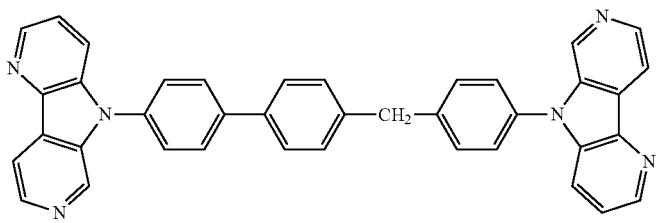 [SMILES: c1cnc2c3ccncc3n(-c3ccc(Cc4ccc(-c5ccc(-n6c7cnccc7c7ncccc76)cc5)cc4)cc3)c2c1] | |
| 180 | 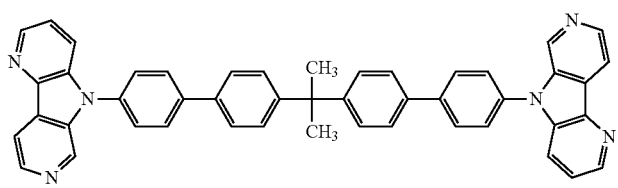 [SMILES: CC(C)(c1ccc(-c2ccc(-n3c4cnccc4c4ncccc43)cc2)cc1)c1ccc(-c2ccc(-n3c4cnccc4c4ncccc43)cc2)cc1] | |
| 181 | 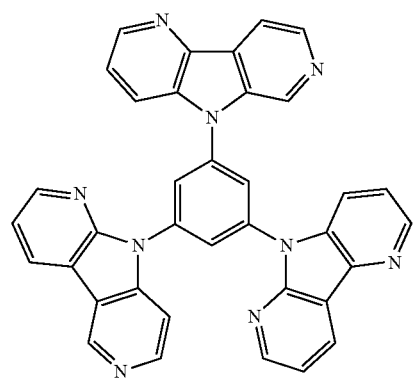 [SMILES: c1cnc2c(c1)c1cnccc1n2-c1cc(-n2c3cnccc3c3ncccc32)cc(-n2c3cccnc3c3cccnc32)c1] | |
| 182 | 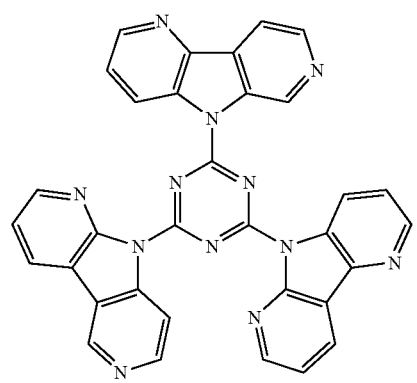 [SMILES: c1cnc2c(c1)c1cnccc1n2-c1nc(-n2c3cnccc3c3ncccc32)nc(-n2c3cccnc3c3cccnc32)n1] | |
| 183 | 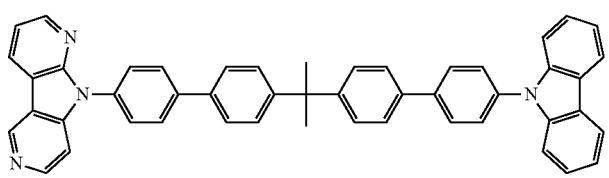 [SMILES: CC(C)(c1ccc(-c2ccc(-n3c4ccccc4c4ccccc43)cc2)cc1)c1ccc(-c2ccc(-n3c4ccncc4c4cccnc43)cc2)cc1] | |
| 184 | 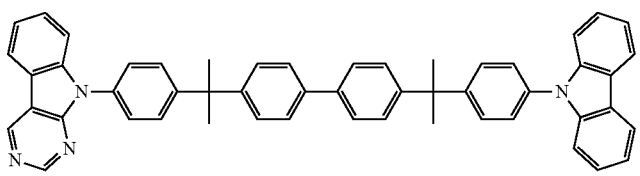 [SMILES: CC(C)(c1ccc(-c2ccc(C(C)(C)c3ccc(-n4c5ccccc5c5cncnc54)cc3)cc2)cc1)c1ccc(-n2c3ccccc3c3ccccc32)cc1] | |

| Compound | Central skeleton | A |
|---|---|---|
| 185 | | |
| 186 | | |
| 187 | | |
| 188 | | |

The emission layer of the present invention can be formed by using a film-forming method known in the art, for example, a vacuum deposition method, a spin coat method, a cast method and an LB method. The thickness of the emission layer is not specifically limited, however, ordinarily selected in the range of 5 nm-5 μm. The emission layer may be formed of one layer containing one kind or two or more kinds of emission materials, or may be formed of plural layers each of which may have the same composition or may have a different composition from each other.

The emission layer may be formed by dissolving the above-mentioned emission material in a solvent together with a binder such as a resin, followed by making into a film by, for example, a spin coat method, as disclosed in, for example, JP-A No. 57-51781. The thickness of the emission layer is not specifically limited and can be arbitrarily selected, however, usually it is in the range of 5 nm-5 μm.

<<Blocking Layer (Electron Blocking Layer, Hole Blocking Layer>>

The blocking layer (for example, an electron blocking layer and a hole blocking layer) of the present invention will now be explained. The thickness of the blocking layer of the present invention is preferably 3 nm-100 nm, and more preferably 5 nm-30 nm.

<<Hole Blocking Layer>>

The hole blocking layer has a function of an electron transport layer in a broad sense and contains a material having an ability of transporting electrons, however, an extremely poor ability of transporting holes, which can increase a recombination probability of electrons and holes by transporting electrons while blocking holes.

In the present invention, the material of this invention for the organic EL element can be preferably used in a layer adjacent to the emission layer, for example, a hole blocking layer or an electron blocking layer.

The hole blocking layer, for example, disclosed in JP-A Nos. 11-204258 and 11-204359, and the hole blocking layer described in page 237 of "Organic EL element and its frontier of industrialization" (published by NTS Corporation, Nov. 30, 1998), can be used as the hole blocking layer of the present invention.

The hole blocking layer of the present invention preferably contains a boron derivative, and more preferably contains a born derivative represented by the afore mentioned Formula (1).

<<Electron Blocking Layer>>

The electron blocking layer has a function of an hole transport layer in a broad sense and contains a material having an ability of transporting holes, however, an extremely poor ability of transporting electrons, which can increase a recombination probability of electrons and holes by transporting holes while blocking electrons. Further, the construction of a hole transport layer which will be described later can be used as an electron blocking layer if necesssary.

In the present invention, the material of this invention for the organic EL element can be preferably used in a layer adjacent to the emission layer, namely, in a hole blocking layer or in an electron blocking layer, and specifically preferably used in a hole blocking layer.

<<Hole Transport Layer>>

The hole transport layer contains a hole transport material having a hole transport ability. A hole injection layer and an electron blocking layer are included in a hole transport layer in a broad sense. The hole transport layer may either be a single layer or a lamination layer containing a plurality of layers.

The hole transport material is not specifically limited, and can be arbitrarily selected from commonly used hole injection-transport materials in a photo conduction material or from the materials known in the art in a hole injection layer or in a hole transport layer of an organic EL element.

A hole transport material means a compound having a hole injection ability, a hole transport ability or an electron blocking ability, and it may be an organic substance or an inorganic substance. Examples of a hole transport material include: a triazole derivative, an oxadiazole derivative, an imidazole derivative, a polyarylalkane derivative, a pyrazoline derivative, a pyrazolone derivative, a phenylenediamine derivative, an arylamine derivative, an amino substituted chalcone derivative, an oxazole derivative, a styrylanthracene derivative, a fluorenone derivative, a hydrazone derivative, a stilbene derivative, a silazane derivative, an aniline-containing copolymer, and an electroconductive oligomer, specifically, a thiophene oligomer.

As the hole transport material, those described above are used, however, a porphyrin compound, an aromatic tertiary amine compound, and a styrylamine compound are preferable, and, specifically, an aromatic tertiary amine compound is preferable.

Typical examples of the aromatic tertiary amine compound and styrylamine compound include: N,N,N',N'-tetraphenyl-4,4'-diaminophenyl, N,N'-diphenyl-N,N'-bis(3-methylphenyl)-[1,1'-biphenyl]-4,4'-diamine (TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl) phenylmethane, bis(4-di-p-tolylaminophenyl) phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino) quadriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostylbene, N-phenylcarbazole, compounds described in U.S. Pat. No. 5,061,569 which have two condensed aromatic rings in the molecule thereof such as 4,4'-bis[N-(1-naphthyl)-N-phenylamino]biphenyl (NPD), and compounds described in JP-A No. 4-308688 such as 4,4',4"-tris[N-(3-methylphenyl)-N-phenylamino]-triphenylamine (MTDATA) in which three triphenylamine units are bonded in a starburst form.

A polymer in which the material mentioned above is introduced in the polymer chain or a polymer having the above mentioned material as the polymer main chain can also be used. As a hole injecting material or a hole transport material, inorganic compounds such as p-Si and p-SiC are usable. The hole transport material in the hole transport layer of the present invention preferably has a fluorescent maximum wavelength of 415 nm or less, and more preferable to have a phosphorescent O—O band of 450 nm or less. Further, the hole transport material preferably has a high Tg.

The hole transport layer can be formed by preparing a thin layer of the above-mentioned hole transport material using a known method such as a vacuum deposition method, a spin coat method, a cast method, an inkjet method, or an LB method. The thickness of the hole transport layer is not specifically limited, however, if is ordinarily from 5 nm to 5000 nm. The hole transport layer may be composed of a single layer structure containing one or more of the materials mentioned above.

<<Electron Transport Layer>>

The electron transport layer contains a material having an electron transport ability, and in a broad sense an electron injection layer or a hole blocking layer are included in an electron transport layer. The electron transport layer can be provided as a single layer or as a plurality of layers composed of the above mentioned material.

The following materials have been known as an electron transporting material, (which serves also as a hole blocking material) used in a single electron transport layer or in the electron transport layer closest to the cathode when plural electron transport layers are employed. The electron transport layer has a function of transporting electrons injected from a cathode to an emission layer, and the material used in the electron transport layer can be optionally selected from the compounds known in the art.

Examples of the material used in the electron transport layer (hereafter, referred to as the electron transport material) include: a nitro-substituted fluorene derivative, a diphenylquinone derivative, a thiopyran diozide derivative, a heterocyclic tetracarboxylic acid anhydride such as naphthaleneperylene, a carbodiimide, a fluolenylidenemethane derivative, an anthraquinodimethane derivative, an anthrone derivative, and an oxadiazole derivative. Moreover, a thiadiazole derivative which is formed by substituting the oxygen atom in the oxadiazole ring of the foregoing oxadiazole derivative with a sulfur atom, and a quinoxaline derivative having a quinoxaline ring known as an electron withdrawing group are usable as the electron transporting material.

A polymer in which the material mentioned above is introduced in the polymer chain or a polymer having the material as the polymer main chain can be also used.

A metal complex of an 8-quinolynol derivative such as aluminum tris(8-quinolynol) (Alq), aluminum tris(5,7-dichloro-8-quinolynol), aluminum tris(5,7-dibromo-8-quinolynol), aluminum tris(2-methyl-8-quinolynol), aluminum tris(5-methyl-8-quinolynol), or zinc bis(8-quinolynol) (Znq), and a metal complex formed by replacing the central metal of the foregoing complexes with another metal atom such as In, Mg, Cu, Ca, Sn, Ga or Pb, can be used as the electron transport material. Furthermore, a metal free or metal-containing phthalocyanine, and a derivative thereof, in which the molecular terminal is replaced by a substituent such as an alkyl group or a sulfonic acid group, are also preferably used as the electron transport material. The distyrylpyrazine derivative exemplified as a material for the emission layer may preferably be employed as the electron transport material. An inorganic semiconductor such as n-Si and n-SiC may also be used as the electron transport material in a similar way as in the hole injection layer and the hole transport layer.

The electron transport layer can be formed employing the above described electron transport materials and by forming into a film using a known method such as a vacuum deposition method, a spin coat method, a cast method, an inkjet method or an LB method. The thickness of electron transport layer is not specifically limited, however, is ordinarily from 5 to 5,000 nm. The electron transport layer may be composed of a single layer containing one kind or two or more kinds of the above-mentioned materials.

Next, the injection layer used as one of the constituting layers of the organic EL element of the present invention will be described.

<Injection Layer>: Electron Injection Layer, Hole Injection Layer

The injection layer is optionally provided, for example, an electron injection layer or a hole injection layer, and may be provided between the anode and the emission layer or the hole transport layer, and between the cathode and the emission layer or the electron transport layer as described above.

The injection layer herein referred to is a layer provided between the electrode and an organic layer in order to reduce the driving voltage or to improve of light emission efficiency. As the injection layer, there are a hole injection layer (an anode buffer layer) and an electron injection layer (a cathode buffer layer), which are described in "Electrode Material" pages 123-166, Div. 2 Chapter 2 of "Organic EL element and its frontier of industrialization" (published by NTS Corporation, Nov. 30, 1998) in detail.

The anode buffer layer (a hole injection layer) is described in, for example, JP-A Nos. 9-45479, 9-260062, and 8-288069 in detail, and its examples include a phthalocyanine buffer layer represented by a copper phthalocyanine layer, an oxide buffer layer represented by a vanadium oxide layer, an amorphous carbon buffer layer, and a polymer buffer layer employing an electroconductive polymer such as polyaniline (emeraldine) or polythiophene.

The cathode buffer layer (an electron injection layer) is described in, for example, JP-A Nos. 6-325871, 9-17574, and 10-74586, in detail, and its examples include a metal buffer layer represented by a strontium or aluminum layer, an alkali metal compound buffer layer represented by a lithium fluoride layer, an alkali earth metal compound buffer layer represented by a magnesium fluoride layer, and an oxide buffer layer represented by an aluminum oxide.

The buffer layer (an injection layer) is preferably very thin and has a thickness of preferably from 0.1 to 100 nm depending on the kind of the material used.

The injection layer can be formed by preparing a thin layer of the above-mentioned injection material using a known method such as a vacuum deposition method, a spin coat method, a cast method, an inkjet method, or an LB method. The thickness of the injection layer is not specifically limited, however, it is ordinarily from 5 nm to 5,000 nm. The injection layer may be composed or a single layer structure containing one kind or two or more kinds of the materials mentioned above.

<<Anode>>

For the anode of the organic EL element, a metal, an alloy, or an electroconductive compound each having a high working function (not less than 4 eV), and mixture thereof are preferably used as the electrode material. Specific examples of such an electrode material include a metal such as Au, and a transparent electroconductive material such as CuI, indium tin oxide (ITO), $SnO_2$, or ZnO. A material capable of forming an amorphous and transparent conductive layer such as IDIXO ($In_2O_3$—ZnO) may also be used. The anode may be prepared by forming a thin layer of the electrode material according to a depositing or sputtering method, and, by forming the layer into a desired pattern according to a photolithographic method. When required precision of the pattern is not so high (not less than 100 μm), the pattern may be formed by depositing or sputtering of the electrode material through a mask having a desired form. When light is emitted through the anode, the transmittance of the anode is preferably 10% or more, and the sheet resistance of the anode is preferably not more than several hundred ohm/sq. The thickness of the layer is ordinarily within the range of from 10-1,000 nm, and preferably from 10-200 nm, although it may vary due to kinds of materials used.

<<Cathode>>

On the other hand, for the cathode, a metal (referred to as an electron injecting metal), an alloy, and an electroconductive compound each having a low working function (not more than 4 eV), and a mixture thereof are used as the electrode material. Specific examples of such an electrode material include sodium, sodium-potassium alloy, magnesium, lithium, a magnesium/copper mixture, a magnesium/silver mixture, a magnesium/aluminum mixture, magnesium/indium mixture, an aluminum/aluminum oxide ($Al_2O_3$) mixture, indium, a lithium/aluminum mixture, and a rare-earth metal. Among them, a mixture of an electron injecting metal and a metal having higher working function than that of the electron injecting metal, such as the magnesium/silver mixture, magnesium/aluminum mixture, magnesium/indium mixture, aluminum/aluminum oxide ($Al_2O_3$) mixture, lithium/aluminum mixture, or aluminum is suitable from the view point of the electron injecting ability and resistance to oxidation. The cathode can be prepared forming a thin layer of such an electrode material by a method such as a deposition or spattering method. The sheet resistance as the cathode is preferably not more than several hundred ohm/sq, and the thickness of the layer is ordinarily in the range of 10 nm-1,000 nm, and preferably 50 nm-200 nm. It is preferable in increasing the light emission efficiency that either the anode or the cathode of the organic EL element is transparent or semi-transparent.

<<Substrate (Also Referred to as Base Plate, Base or Support)>>

The substrate employed for the organic EL element of the present invention is not restricted to specific kinds of materials such as glass and plastic, as far as it is transparent. Examples of the substrate preferably used include glass, quartz and light transmissible plastic film. Specifically preferred one is a resin film capable of providing flexibility to the organic EL element.

Examples of the resin film include films of polyethylene terephthalate (PET), polyethylene naphthalate (PEN), polyethersulfone (PES), polyetherimide, polyetheretherketone, polyphenylene sulfide, polyarylate, polyimide, polycarbonate (PC), cellulose triacetate (TAC) and cellulose acetate propionate (CAP).

The surface of the resin film may have a layer of an inorganic or organic compound or a hybrid layer of both compounds which is preferably a high barrier film having a moisture permeability of not more than $0.01$ g/m$^2$·day·atm.

The external efficiency of the light emission of the organic electroluminescence element of the present invention is preferably not less than 1%, and more preferably not less than 2% at room temperature. Herein, external quantum efficiency (%) is represented by the following formula:

External quantum efficiency (%)=((the number of photons emitted to the exterior of the organic EL element)/(the number of electrons supplied to the organic EL element))×100

A hue improving filter such as a color filter may be used in combination.

When used as an illuminator, a film being subjected to a surface roughening treatment (for example, an antiglare film) may be used together, in order to reduce the emission irregularity.

When used as a multicolored display device, at least two organic EL elements having different emission maximum wavelengths are used. A preferable example of preparing an organic EL element will now be explained.

<<Preparation Method of Organic EL Element>>

For one example, the preparation of the organic EL element will be described, the EL element being composed of: Anode/Hole injection layer/Hole transport layer/Emission layer/Electron transport layer/Cathode buffer layer/Cathode.

A thin layer of a desired material for an electrode such as a material for the anode is formed on a suitable substrate by a vacuum deposition or sputtering method to prepare the anode so that the thickness of the layer is not more than 1 μm and preferably within the range of from 10 to 200 nm. Then organic compound containing thin layers including the hole injection layer, the hole transport layer, the emission layer, the hole blocking layer and the electron transport layer are formed on the resulting anode.

As methods for formation of the thin layers, as the same as described above, there are a spin coating method, a cast method, an inkjet method, vapor deposition method and a printing method, however, a vacuum deposition method, a spin coating method, an inkjet method and a printing method are preferably used, since a uniform layer without a pinhole can be formed. Different methods may be used for formation of different layers. When the vapor deposition method is used for the thin layer formation method, although conditions of the vacuum deposition differs due to kinds of materials used, vacuum deposition is carried out to form a layer by selecting suitable conditions, in the range of, at a boat temperature from 50-450° C., at a degree of vacuum $10^{-6}$ to $10^{-2}$ Pa, at a deposition speed of 0.01-50 nm/second, and at a substrate temperature of −50-300° C., and a thickness of 0.1 nm-5 μm.

After these layers have been formed, a thin layer of a material for a cathode is formed thereon to prepare a cathode, employing, for example, a vacuum deposition method or sputtering method to give a thickness of not more than 1 μm, and preferably 50-200 nm. Thus, a desired organic EL element is obtained. It is preferred that the layers from the hole injection layer to the cathode are continuously formed under one time of vacuuming to obtain an organic EL element. However, on the way of the layer formation under vacuum, a different layer formation method by taking the layer out of the vacuum chamber may be inserted. When the different method is used, the process is required to be carried out under a dry inert gas atmosphere.

<<Display Device>>

The display device of the present invention will now be described.

In the present invention, the display device may be single color or may be multicolor, however, a multicolor display device will now be described. In the multicolor display, the emission layer only is formed using a shadow mask, and the other layers can be formed all over the substrate employing a vapor deposition method, a cast method, a spin coat method an inkjet method or a printing method.

When the emission layer only is formed by patterning, the layer formation is, although not specifically limited, carried out preferably according to a vapor deposition method, an inkjet method or a printing method. When a vapor deposition method is used as the layer formation method, patterning of the layer is preferably carried out employing a shadow mask.

Further, the organic EL element can be prepared in the reverse order, in which the cathode, the electron transport layer, the hole blocking layer, the emission layer, the hole transport layer, and the anode are formed in that order.

When a direct current voltage, a voltage of 2 to 40 V is applied to thus obtained multicolor display, setting the anode as a "+" polarity and the cathode as a "−" polarity, light emission as observed. When a voltage with the reverse polarity is applied, no current flows and no light emission is observed. When an alternating current is applied, light emission is observed only when "+" is applied to the anode and "−" is applied to the cathode. Arbitrary wave shape of alternating current may be used.

The multicolor display device can be used as a display device, a display, or various light emission sources. The display device or the display can present a full color image by employing three kinds of organic EL elements emitting a blue light, a red light and a green light.

Examples of the display device or the display include a television, a personal computer, a mobile device or an AV device, a display for text broadcasting, and an information display used in a car. The display device may be used as specifically a display for reproducing a still image or a moving image. When the display device is used as a display for reproducing a moving image, the driving method may be either a simple matrix (passive matrix) method or an active matrix method.

Examples of an lighting device include a home lamp, a room lamp in a car, a backlight for a watch or a liquid crystal, a light source for boarding advertisement, a signal device, a light source for a photo memory medium, a light source for an electrophotographic copier, a light source for an optical communication instrument, and a light source for an optical sensor, however, are not limited thereto.

<<Lighting Device>>

The lighting device of the present invention will now be described.

The organic EL element of the present invention may be an organic EL element having a resonator structure. The organic EL element having a resonator structure is applied to a light source for a photo-memory medium, a light source for an electrophotographic copier, a light source for an optical communication instrument, or a light source for a photo-sensor, however, its application is not limited thereto. In the above application, a laser oscillation may be carried out.

The organic EL element of the present invention can be used as a lamp such as an illuminating lamp or a light source for exposure, as a projection device for projecting an image, or as a display for directly viewing a still image or a moving image. When the element is used in a display for reproducing a moving image, the driving method may be either a simple matrix (passive matrix) method or an active matrix method. The display can present a full color image by employing two or more kinds of organic EL elements each emitting light with a different color.

One of the examples of the display containing the organic EL element of the present invention will be explained below employing Figures.

FIG. 1 is a schematic drawing of one example of a display containing an organic EL element. It is a schematic view of display such as that of a cellular phone, displaying image information due to light emission from the organic EL.

Display 1 contains a display section A having plural pixels and a control section B carrying out image scanning based on image information to display an image in the display section A.

The control section B is electrically connected to the display section A, transmits a scanning signal and an image data signal to each of the plural pixels based on image information from the exterior, and conduces image scanning which emits light from each pixel due to the scanning signal according to the image data signal, whereby an image is displayed on the display section A.

Figure 2:
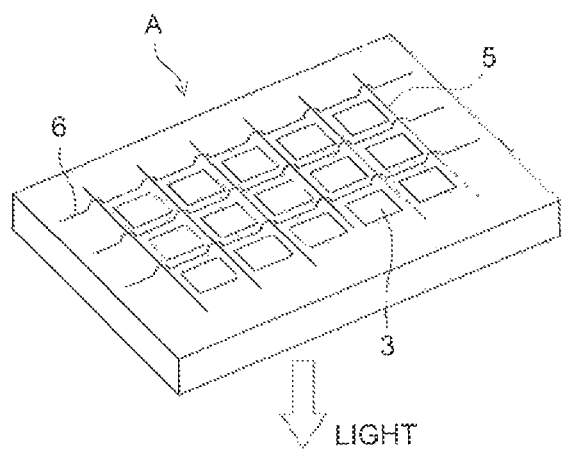
FIG. 2 is a schematic drawing of a displaying means A.

FIG. 2 is a schematic drawing of a display section A. The display section A contains a substrate, plural pixels 3, and a wiring section containing plural scanning lines 5 and plural data lines 6. The main members of the display section A will be explained below. In FIG. 2, light from pixels 3 is emitted in the direction of an arrow (downward).

The plural scanning lines 5 and plural data lines 6 of the wiring section 2 each are composed of an electroconductive material, the lines 5 and the lines 6 being crossed with each other at a right angle, and connected with the pixels 3 at the crossed points (not illustrated in detail).

The pixels 3, when the scanning signal is applied from the scanning lines 5, receive the data signal from the data lines 6, and emit light corresponding to the image data received. Provision of red light emitting pixels, green light emitting pixels, and blue light emitting pixels side by side on the same substrate can display a full color image.

Next, an emission process of pixels will be described.

Figure 3:
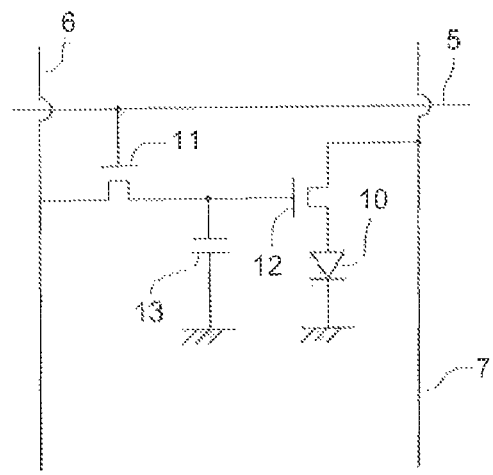
FIG. 3 is the equivalent drawing of a driving circuit for constituting a pixel

FIG. 3 is a schematic drawing of a pixel.

The pixel contains an organic EL element 10, a switching transistor 11, a driving transistor 12, and a capacitor 13. When a pixel with a red light emitting organic EL element, a pixel with a green light emitting organic EL element, and a pixel with a blue light emitting organic EL element are provided side by side on the same substrate, a full color image can be displayed.

In FIG. 3, an image data signal is applied through the data lines 6 from the control section B to a drain of the switching transistor 11, and when a scanning signal is applied to a gate of the switching transistor 11 through the scanning lines 5 from the control section B (shown in FIG. 1), the switching transistor 11 is switched on, and the image signal data applied to the drain is transmitted to the capacitor 13 and the gate of the driving transistor 12.

The capacitor 13 is charged according to the electric potential of the image data signal transmitted, and the driving transistor 12 is switched on. In the driving transistor 12, the drain is connected to an electric source line 7, and the source to an organic EL element 10. Current is supplied from the electric source line 7 to the organic EL element 10 according to the electric potential of the image data signal applied to the gate.

The scanning signal is transmitted to the next scanning line 5 according to the successive scanning of the control section B, the switching transistor 11 is switched off. Even if the switching transistor 11 is switched off, the driving transistor 12 is turned on since the capacitor 13 maintains a charged potential of image data signal, and light emission from the organic EL element 10 continues until the next scanning signal is applied. When the next scanning signal is applied according to the successive scanning, the driving transistor 12 works according to an electric potential of the next image data signal synchronized with the scanning signal, and light is emitted from the organic EL element 10.

That is, light is emitted from the organic EL element 10 in each of the plural pixels 3 due to the switching transistor 11 as an active element and the driving transistor 12 each being provided in the organic EL element 10 of each of the plural pixels 3. This emission process is called an active matrix process.

Herein, light emission from the organic EL element 10 may be emission with plural gradations according to image signal data of multiple value having plural gradation potentials, or emission due to on-off according to a binary value of the image data signals.

The electric potential of the capacitor 13 may maintain till the next application of the scanning signal, or may be discharged immediately before the next scanning signal is applied.

In the present invention, light emission may be carried out employing a passive matrix method as well as the active matrix method as described above. The passive matrix method is one in which light is emitted from the organic EL element according to the data signal only when the scanning signals are scanned.

Figure 4:
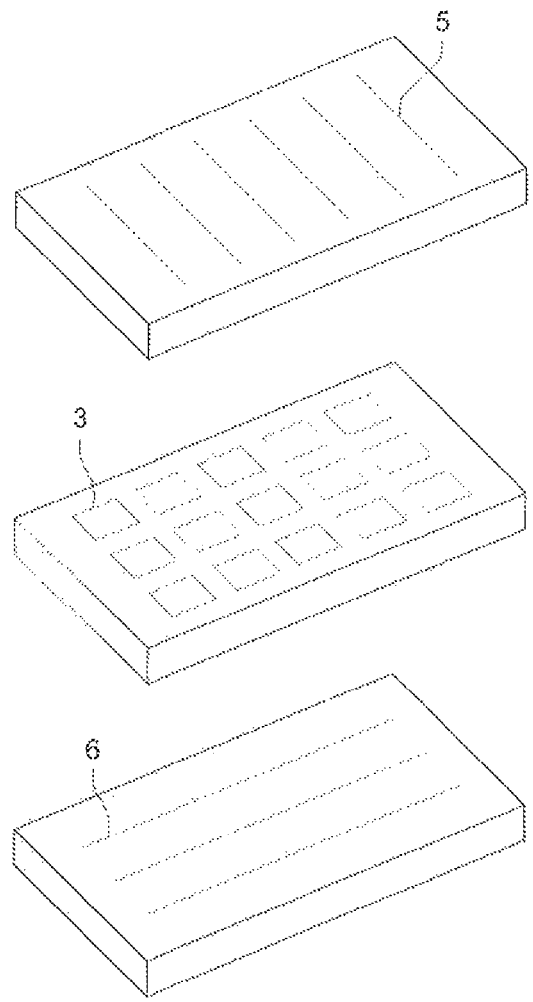
FIG. 4 is a schematic drawing of a displaying device by passive matrix system.

FIG. 4 is a schematic drawing of a display employing a passive matrix method. In FIG. 4, pixels 3 are provided between the scanning lines 5 and the data lines 6, crossing with each other.

When scanning signal is applied to scanning line 5 according to successive scanning, pixel 3 connecting the scanning line 5 emits according to the image data signal. The passive matrix method has no active element in the pixel 3, which reduces manufacturing cost of a display.

The organic EL material of the invention can be applied for an organic EL element emitting substantial white light for the lighting device. White light is obtained by mixing plural color light simultaneously emitted from plural light emitting materials. As the combination of plural colors of light, one containing three color light each having the maximum intensity wavelength of blue, green and red of three primary colors, respectively, and one containing two complementary colors such as blue and yellow or bluish green and orange, are either applicable.

The combination of light emission materials for obtaining the plural color light may be either a combination of plural materials (light emission dopants) each emitting phosphorescent or fluorescent light or a combination of the light emission material emitting fluorescent light or phosphorescent light and a dye capable of emitting light when excited by the light emitted from the light emission material. In the white light emission organic EL element relating to the invention, the combination of plural light emission dopants is preferable.

As the layer constitution of the organic EL element for obtaining plural colors of light, one in which plural light emission dopants are contained in one light emission layer, one in which the element has plural light emission layers and dopants each emitting different color light from each other are contained each of the layers, respectively, and one in which fine pixels each emitting different color light are formed in a matrix state are applicable.

In the white organic EL element of the invention, patterning may be provided on the occasion of layer formation according to necessity by metal masking or ink-jet printing. When the patterning is provided, any of the patterning of electrodes, that of electrodes and light emission layer, and that of whole element may be applied.

The light emission material to be used in the light emission layer is not specifically limited. In a case of backlight of liquid crystal display, for example, white light can be formed by suitably selecting material from the platinum complexes of the invention and known light emission materials so as to suite the wavelength range corresponding to the property of color filter CF.

As above-described, the white light emission organic EL elements are usefully applied as various light sources, for example, lighting devices for domestic lighting and car room lighting, one kind of lamp for exposing light source, and displaying device such as backlight of liquid crystal displays additionally to the foregoing indication devices and displays.

Figure 5:
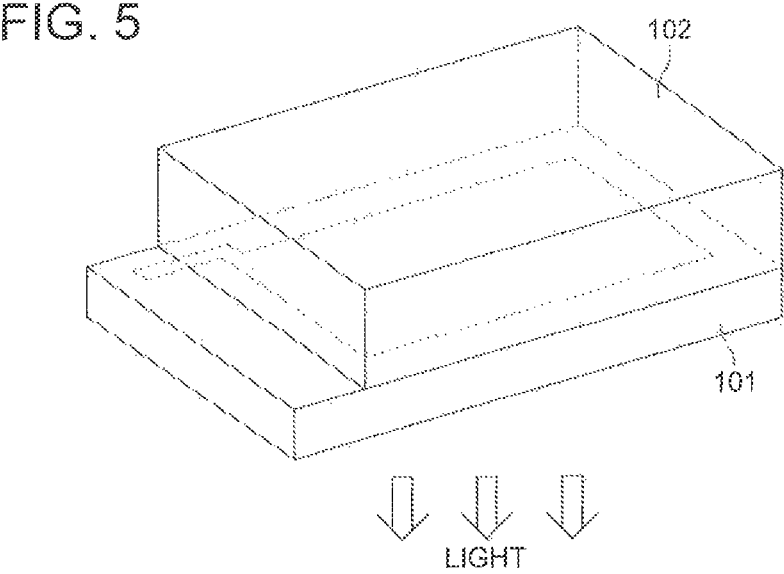
FIG. 5 is a schematic drawing of a lighting device

FIG. 5 is a schematic drawing of a lighting device, comprising a transparent substrate 101 and a glass cover 102.

Other than the above, the element is used in wide field such as backlight of watch, an advertisement signboard, a signal, a light source of light memorizing medium, a light source of electrophotographic copier, a light source of light communication processor, a light source of photo-sensor, and domestic electric appliances requiring a displaying device.

EXAMPLES

The invention is described below referring examples, but the invention is not limited to the examples.

Example 1

<<Preparation of Organic EL Element OLED 1-1>>

An anode was patterned on a substrate, NA-45 manufactured by NH Techno Glass Co., Ltd., composed of a glass plate on which an ITO layer of 150 nm. The transparent substrate having the ITO transparent electrode was washed by ultrasonic wave washing treatment using iso-propyl alcohol and dried by dried nitrogen gas, and then subjected to UV ozone cleaning for 5 minutes. The transparent substrate was fixed on a substrate holder of a vacuum vapor deposition apparatus available on the market, and α-NPD, CBP, Pt-2, BCP and Alq$_3$ were separately charged in five tantalum resistive heating boats, respectively, and set in the first vacuum chamber of the vacuum vapor deposition apparatus.

Besides, lithium fluoride and aluminum were each charged into a tantalum resistive heating boat and a tungsten resistive heating boat, respectively, and the boats were set in the second vacuum chamber.

The internal pressure of the first vacuum chamber was reduced by $4 \times 10^{-4}$ Pa, and then the heating boat containing α-NPD was heated by applying electric current so that α-NPD was deposited on the transparent substrate at a depositing rate of from 0.1 nm/sec to 0.2 nm/sec to form a hole injection/transfer layer having a thickness of 25 nm.

Next, the boat containing CBP and that containing Pt-2 were independently heated by applying electric current so as to make the ratio of depositing rate of CBP as the light emission host and that of Pt-2 as the light emission dopant to 100:7 and a layer of 30 nm was deposited to provide an emission layer.

After that, the heating boat containing BCP was heated by applying electric current to provide a hole blocking layer of 10 nm at a depositing rate of from 0.1 to 0.2 nm/sec. Furthermore, the heating boat containing Alq$_3$ was heated by applying electric current to form an electron transfer layer of 40 nm at a deposition rate of from 0.1 to 0.2 nm/sec.

The element on which the above layers were provided was transferred into the second vacuum chamber, while holding vacuum and then a stainless steel mask having a rectangular hole was stet by remote controlling from outside of the vacuum chamber so that the mask was positioned on the electron transfer layer.

The internal pressured of the second vacuum chamber was reduced by $2 \times 10^{-4}$ Pa and then the boat containing lithium fluoride was heated by applying electric current to form a cathode buffer layer of 0.5 nm at a deposition rate of from 0.01 to 0.02 nm/sec and then the boat containing aluminum was heated by applying electric current to form a cathode of 150 nm at a deposition rate of from 1 to 2 nm/sec. The resultant organic EL element was transferred into a glove box in which the atmosphere was replaced by highly purified nitrogen gas having a purity of not less than 99.999%, without contact with air and sealed so that the interior of the element was replaced by nitrogen gas. Thus Organic EL Element OLED 1-1 was prepared.

<<Preparation of Organic EL Elements OLED 1-2 to 1-16>>

Organic EL elements OLED 1-2 to 1-16 were prepared in the same manner as in the above Organic EL Element OLED 1-1 except that the light emission dopant and hole blocking material were respectively changed as shown in Table 1.

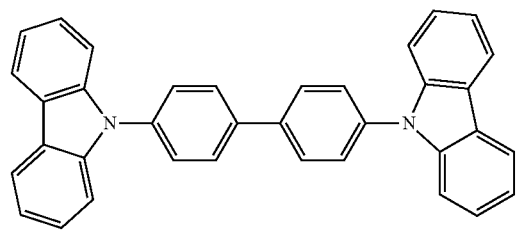

CBP

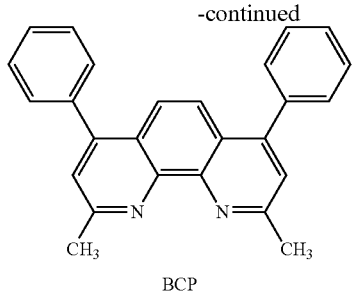

BCP

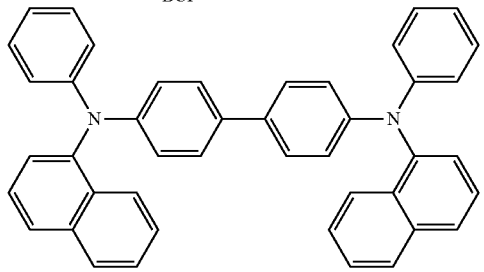

α-NPD

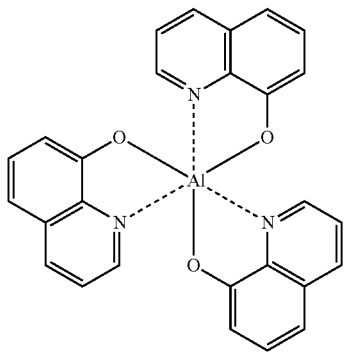

Alq₃

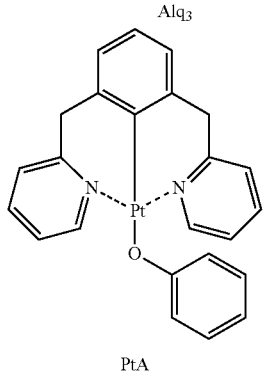

PtA

Thus obtained Organic EL Elements OLED 1-1 to 1-16 were subjected to the following evaluations.

<<External Quantum Efficiency>>

Each of Organic EL Elements OLED 1-1 to 1-16 was made to light by applying a constant electric current of 2.5 mA/cm² at room temperature (about 23 to 25° C.) and external quantum efficiency η was calculated by measuring luminance of L in cd/m² just after the lighting by CS-1000 manufactured by Konica Minolta Co., Ltd. The external quantum efficiency was expressed by a relative value when that of Organic EL Element 1-1 was set at 100.

<<Color Difference>>

Each of Organic EL Elements OLED 1-1 to 1-16 was turned on line by applying a constant electric current of 2.5 mA/cm² at room temperature (about 23 to 25° C.) and CIE chromaticity ((x, y)=(a, b)) of the color of emitted light just after the turning on light was measured and the difference Δ between blue of NTSC (modern) ((z, y)=(0.155, 0.07)) was calculated.

The Δ was calculated by the following expression and the measurement of the CIE chromaticity was carried out by CS-1000 manufactured by Konica Minolta Co., Ltd.

$$\Delta = (|0.155-a|^2 + |0.07-b|^2)^{1/2}$$

The results of the evaluations are listed in Table 1.

TABLE 1

| Element No. | Light emission dopant | Hole blocking material | External quantum efficiency | Chromaticity difference | Remarks |
|---|---|---|---|---|---|
| OLED1-1 | Pt-2 | BCP | 100 | 0.32 | Comp. |
| OLED1-2 | PtA | BCP | 90 | 0.29 | Comp. |
| OLED1-3 | 1-2 | BCP | 113 | 0.20 | Inv. |
| OLED1-4 | 1-6 | BCP | 121 | 0.15 | Inv. |
| OLED1-5 | 1-12 | BCP | 116 | 0.16 | Inv. |
| OLED1-6 | 1-15 | BCP | 109 | 0.20 | Inv. |
| OLED1-7 | 1-16 | BCP | 117 | 0.17 | Inv. |
| OLED1-8 | 1-20 | BCP | 120 | 0.18 | Inv. |
| OLED1-9 | 1-23 | BCP | 112 | 0.19 | Inv. |
| OLED1-10 | 1-2 | Compound 74 | 115 | 0.20 | Inv. |
| OLED1-11 | 1-6 | Compound 74 | 123 | 0.15 | Inv. |
| OLED1-12 | 1-12 | Compound 73 | 119 | 0.16 | Inv. |
| OLED1-13 | 1-15 | Compound 74 | 111 | 0.20 | Inv. |
| OLED1-14 | 1-16 | Compound 73 | 119 | 0.17 | Inv. |
| OLED1-15 | 1-20 | Compound 74 | 124 | 0.18 | Inv. |
| OLED1-16 | 1-23 | Compound 73 | 114 | 0.19 | Inv. |

Comp.: Comparative, Inv.: Inventive

It is cleared from Table 1 that the organic EL elements prepared by using the platinum complexes according to the invention in the light emission layer can attain higher light emission efficiency and higher color purity compared to the comparative organic EL elements. Moreover, the effects of the invention are enhanced by the use of the compounds represented by Formula I of the invention in the hole blocking layer.

Example 2

<<Preparation of Organic EL Element OLED 2-1>>

An anode was patterned on a substrate, NA-45 manufactured by NH Techno Glass Co., Ltd., composed of a glass plate on which an ITO layer of 150 nm. The transparent substrate having the ITO transparent electrode was washed by ultrasonic wave washing treatment using iso-propyl alcohol and dried by dried nitrogen gas, and then subjected to UV ozone cleaning for 5 minutes.

The transparent substrate was fixed on a substrate holder of a vacuum vapor deposition apparatus available on the market, and α-NPD, CBP, Ir-13, BCP and Alq₃ were separately charged in five tantalum resistive heating boats and set in the first vacuum chamber of the vacuum vapor deposition apparatus.

Besides, lithium fluoride and aluminum were each charged a tantalum resistive heating boat and a tungsten resistive heating boat, respectively, and the boats were set in the second vacuum chamber.

The internal pressure of the first vacuum chamber was reduced by $4 \times 10^{-4}$ Pa, and then the heating boat containing α-NPD was heated by applying electric current so that α-NPD was deposited on the transparent substrate at a depositing rate of from 0.1 nm/sec to 0.2 nm/sec to form a hole injection/transfer layer having a thickness of 30 nm.

Next, the boat containing CBP and that containing Ir-13 were independently heated by applying electric current so as to make the ratio of depositing rate of CBP as the light emission host and that of Pt-2 as the light emission dopant to 100:7 and a layer of 30 nm was deposited to provide an emission layer.

After that, the heating boat containing BCP was heated by applying electric current to provide a hole blocking layer of 10 nm at a depositing rate of from 0.1 to 0.2 nm/sec. Furthermore, the heating boat containing Alq₃ was heated by applying electric current to form an electron transfer layer of 30 nm at a deposition rate of from 0.1 to 0.2 nm/sec.

The element on which the above layers were provided was transferred into the second vacuum chamber while holding vacuum and then a stainless steel mask having a rectangular hole was stet by remote controlling from outside of the vacuum chamber so that the mask was positioned on the electron transfer layer.

The internal pressured of the second vacuum chamber was reduced by $2 \times 10^{-4}$ Pa and then the boat containing lithium fluoride was heated by applying electric current to form a cathode buffer layer of 0.5 nm at a deposition rate of from 0.01 to 0.02 nm/sec and then the boat containing aluminum was heated by applying electric current to form a cathode of 150 nm at a deposition rate of from 1 to 2 nm/sec. The resultant organic EL element was transferred into a glove box in which the atmosphere was replaced by highly purified nitrogen gas having a purity of not less than 99.999%, without contact with air and shield so that the interior of the element was replaced by nitrogen gas. Thus Organic EL Element OLED 2-1 was prepared.

<<Preparation of Organic EL Elements OLED 5-2 to 2-13>>

Organic EL Elements OLED 2-2 to 2-13 were prepared in the same manner as in Organic EL Element OLED 2-1 except that the light emission dopant was changed as described in Table 2.

Thus obtained Organic EL Elements OLED 2-1 to 2-13 were evaluation as to the external quantum efficiency and the chromaticity difference in the same manner as in Example 1.

Thus obtained results are listed in Table 2.

TABLE 2

| Element No. | Light emission dopant | Hole blocking material | External quantum efficiency | Chromaticity difference | Remarks |
|---|---|---|---|---|---|
| OLED2-1 | Ir-13 | BCP | 100 | 0.26 | Comp. |
| OLED2-2 | 2-4 | BCP | 115 | 0.19 | Inv. |
| OLED2-3 | 2-6 | BCP | 118 | 0.20 | Inv. |
| OLED2-4 | 2-19 | BCP | 125 | 0.14 | Inv. |
| OLED2-5 | 2-23 | BCP | 127 | 0.15 | Inv. |
| OLED2-6 | 2-27 | BCP | 121 | 0.17 | Inv. |
| OLED2-7 | 2-34 | BCP | 112 | 0.20 | Inv. |
| OLED2-8 | 2-4 | Compound 73 | 117 | 0.19 | Inv. |
| OLED2-9 | 2-6 | Compound 73 | 121 | 0.20 | Inv. |
| OLED2-10 | 2-19 | Compound 74 | 129 | 0.14 | Inv. |
| OLED2-11 | 2-23 | Compound 74 | 130 | 0.15 | Inv. |
| OLED2-12 | 2-27 | Compound 73 | 125 | 0.17 | Inv. |
| OLED2-13 | 2-34 | Compound 74 | 114 | 0.20 | Inv. |

Comp.: Comparative, Inv.: Inventive

It is cleared from Table 2 that the organic EL elements prepared by using the iridium complexes according to the invention in the light emission layer can attain higher light emission efficiency and higher color purity compared to the comparative organic EL elements. Moreover, the effects of the invention are enhanced by the use of the compounds represented by Formula I of the invention in the hole blocking layer.

Example 3

<<Preparation of Full Color Displaying Device>>
(Preparation of Blue Light Emission Element)
Organic EL Element 1-4 prepared in Example 1 was used as a blue light emission element.
(Preparation of Green Light Emission Element)
A green light emission element was prepared in the same manner as in Organic EL Element 2-1 except that Ir-13 was replaced by Ir-1.
(Preparation of Red Light Emission Element)
A red light emission element was prepared in the same manner as in Organic EL Element 2-1 except that Ir-13 was replaced by Ir-9.

An active matrix type full color displaying apparatus was prepared by orienting the above prepared red, green and blue light emission organic EL elements as shown in FIG. 1. In FIG. 2, a schematic drawing of the displaying portion A of the displaying device is only displayed. In the displaying device, plural scanning lines 5, wiring containing data lines 6 and oriented plural pixels 3 (pixels each emitting red, green and red light) on a same substrate, and the scanning lines 5 and the data lines 6 are each composed of an electroconductive material and the scanning line 5 and the data line 6 are crossed at an right angle in a grid state and connected to the pixel 3 at the crossing point (detail of the structure is not shown in the drawing). The plural pixels 3 were driven by an active matrix system composed of the organic EL elements each corresponding to individual color, a switching transistor as the active element and a driving transistor. When a scanning signal was applied from the scanning line 5, the organic EL element received image signals from the data lines 6 and emitted light corresponding to the image data. A full color displaying device was prepared by suitably orienting the red, green and blue pixels as above described.

It was confirmed that full color moving images with high luminance, durability and sharpness can be displayed by driving the above prepared full color displaying device.

Example 4

<<Preparation of White Light Emission Device and White Light Lighting Device>>

On the transparent substrate similar to that in Example 2, an electrode of 20 mm×20 mm was patterned and a layer of α-NPD of 25 nm was provided on the electrode as a hole injection/transfer layer. After that, electric current was individually applied to each of the heating boat containing Compound 74, that containing Compound 1-6 and that containing Ir-9 while controlling the current so that the ratio of the deposition rate of Compound 74 as the light emission host and Compound 1-6 and Ir-9 was made to 100:6:0.5 to provide a light emission layer of 30 nm.

After that, a hole blocking layer having a thickness of 10 nm was made by deposition of BCP. Moreover, a layer of Alq$_3$ of 40 nm was formed to form an electron transfer layer.

A mask having a hole having a shape of similar to the transparent electrode was set and a layer of lithium fluoride of 0.5 nm as a cathode buffer layer and an aluminum layer of 150 nm were provided.

Figure 6:
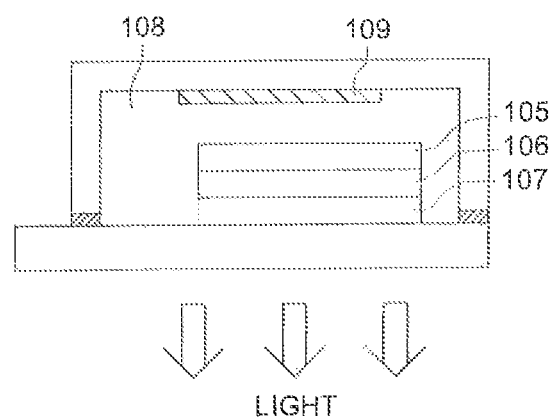
FIG. 6 is a cross section of a lighting device

The element was sealed in the same structural can in the same manner as in Example 2 to prepare a flat-shaped lamp. The schematic drawings are shown in FIGS. 5 and 6. The schematic drawing and the cross section are each shown in FIGS. 5 and 6, respectively. It was confirmed that approximately white light can be obtained by applying electric power and the device can be used as a lighting device.

Example 5

An anode of indium tin oxide (ITO) having a thickness of 200 nm was formed on a glass substrate of 25 mm×15 mm×0.5 mm by a spattering method applying direct electric current. The mole ratio of indium to tin in the ITO layer was 95:5, and the surface resistivity of the anode was 10 Ω/sq. A dichloroethane solution of polyvinylcarbazole (a positive hole transfer binder polymer), Ir-13 (a blue light emission orthometallated complex) and 2-(4-biphenylyl)-5-(4-t-butylphenyl)-1,3,4-oxadiazole (an electron transfer material) in a weight ratio of 200:2:50 was coated On the anode by a spin coater to form a light emission layer of 100 nm. A mask was patterned on thus obtained organic compound layer so as to provide a mask for making a light emission area of 5 mm×5 mm, and then a lithium fluoride layer of 0.5 nm as a cathode buffer layer and an aluminum layer of 150 nm as a cathode were deposited in a vacuum deposition apparatus. After that, aluminum leads were each provided to the anode and cathode to prepare a light emission element. The resultant element was set in a globe box filled by nitrogen gas and sealed into a glass sealing container using a UV curable adhesive XNR 5493 manufactured by Nagase Ciba Co., Ltd. Thus blue light emission Organic EL Element OLED 5-1 according to the invention was prepared. Blue light emission Organic EL Elements 5-2 to 5-6 were prepared in the same manner as in Organic EL Element OLED 5-1 except that Ir-13 was changed by the compounds listed in Table 3.

These blue light emission organic EL elements were each subjected to evaluation according to the following method. Direct count voltage was applied to the element for emitting light by a source measure unit 2004, manufactured by Toyo Technica Co., Ltd., and the luminance (cd/m$^2$) when a DC voltage of 10 V was applied and the light emission efficiency (lm/W) when an electric current of 2.5 mA/cm$^2$ was applied. Evaluation results are shown in Table 3.

TABLE 3

| Element No. | Light emission dopant | Luminance of emitted light (cd/m$^2$) | Light emission efficiency (lm/W) | |
|---|---|---|---|---|
| OLED5-1 | Ir-13 | 100 | 100 | Comparative |
| OLED5-2 | 1-46 | 121 | 139 | Inventive |

TABLE 3-continued

| Element No. | Light emission dopant | Luminance of emitted light (cd/m$^2$) | Light emission efficiency (lm/W) | |
|---|---|---|---|---|
| OLED5-3 | 1-44 | 118 | 130 | Inventive |
| OLED5-4 | 1-40 | 117 | 125 | Inventive |
| OLED5-5 | 2-38 | 115 | 128 | Inventive |

It is clear in Table 3 that the blue light emission organic EL elements are superior to the comparative sample.

What is claimed is:

1. An organic electroluminescence element comprising:
a light emission layer wherein the light emission layer comprises metal complex represented by the following Formula 4 or Formula 5, or an isomer thereof as a part of the structure thereof;

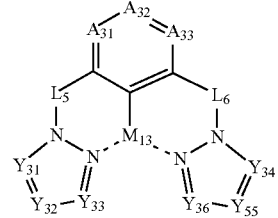

Formula 4 in the above formula, $A_{31}$, $A_{32}$, $A_{33}$, $Y_{31}$, $Y_{32}$, $Y_{33}$, $Y_{34}$, $Y_{35}$ and $Y_{36}$ are each a carbon atom or a nitrogen atom; $m_{13}$ is iridium; and $L_5$ and $L_6$ are each an alkylene group,

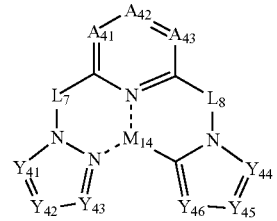

Formula 5 in the above formula, $A_{41}$, $A_{42}$, $A_{43}$, $Y_{41}$, $Y_{42}$, $Y_{43}$, $Y_{44}$, $Y_{45}$ and $Y_{46}$ are each a carbon atom or a nitrogen atom; $M_{14}$ is Ir; and $L_7$ and $L_8$, are each an alkylene group.

2. An organic electroluminescence element comprising:
a light emission layer wherein the light emission layer comprises a metal complex represented by the following Formula 6 or an isomer thereof as a part of the structure thereof;

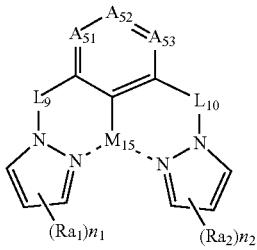

Formula 6 in the above formula, $A_{51}$, $A_{52}$ and $A_{53}$ are each a carbon atom or a nitrogen atom; $M_{15}$ is iridium; $L_9$ and $L_{10}$ are each an alkylene group.

3. An organic electroluminescence element comprising:
a light emission layer wherein the light emission layer comprises a metal complex represented by the follow Formula 7 or an isomer thereof as part of the structure thereof;

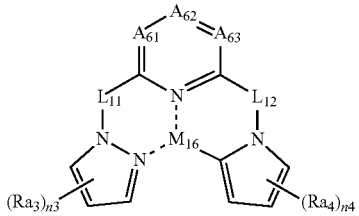

Formula 7 in the above formula, $A_{61}$, $A_{62}$ and $A_{63}$ are each a carbon atom or a nitrogen atom; $M^{16}$ is iridium; $L_{11}$ and $L_{12}$ are each an alkylene group.

4. The organic electroluminescence element of claim 1, comprising a plurality of layers, and wherein at least one of the layers contains a carbazole compound or a compound represented by the following Formula I;

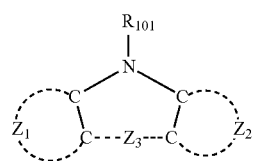

Formula I in the above formula, $Z_1$ is a group of atoms forming an aromatic heterocyclic ring, $Z_2$ is a group of atoms forming an aromatic heterocyclic ring or an aromatic hydrocarbon ring, $Z_3$ is a divalent bonding group or a simple bond, and $R_{101}$ is a hydrogen atom or a substituent.

5. A displaying device having the organic electrolaminescence element of claim 1.

6. A lighting device having the organic electroluminescence element of claim 1.

* * * * *